United States Patent
Devarakonda et al.

(10) Patent No.: US 9,539,328 B2
(45) Date of Patent: *Jan. 10, 2017

(54) TAMPER RESISTANT COMPOSITION COMPRISING HYDROCODONE AND ACETAMINOPHEN FOR RAPID ONSET AND EXTENDED DURATION OF ANALGESIA

(71) Applicant: MALLINCKRODT LLC, Hazelwood, MO (US)

(72) Inventors: Krishna Devarakonda, St. Louis, MO (US); Michael J. Giuliani, Creve Coeur, MO (US); Vishal K. Gupta, Hillsborough, NJ (US); Ralph A. Heasley, Webster Groves, MO (US); Susan Shelby, Town and Country, MO (US)

(73) Assignee: MALLINCKRODT LLC, Hazelwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/479,129

(22) Filed: Sep. 5, 2014

(65) Prior Publication Data

US 2014/0378498 A1    Dec. 25, 2014

Related U.S. Application Data

(63) Continuation of application No. 13/473,578, filed on May 16, 2012.

(Continued)

(51) Int. Cl.
*A61K 9/20* (2006.01)
*A61K 47/10* (2006.01)
(Continued)

(52) U.S. Cl.
CPC ............... *A61K 47/10* (2013.01); *A61K 9/209* (2013.01); *A61K 9/2031* (2013.01);
(Continued)

(58) Field of Classification Search
CPC ........................................................ A61K 9/20
See application file for complete search history.

(56) References Cited

U.S. PATENT DOCUMENTS 4,713,243 A    12/1987  Schiraldi et al.
4,851,226 A     7/1989  Julian et al.
(Continued)

FOREIGN PATENT DOCUMENTS

EP          0159852 A2    10/1985
EP          1140026 B1    10/2001
(Continued)

OTHER PUBLICATIONS

*Mallinckrodt LLC, et al. v. Watson Laboratories, Inc.*, Case No. 2:15v3800 (New Jersey)—Complaint dated Jun. 5, 2015 [D.I. 1] (Separated into two parts).
(Continued)

*Primary Examiner* — Benjamin Packard
(74) *Attorney, Agent, or Firm* — Mayer Brown LLP

(57) ABSTRACT

The present disclosure provides an extended release pharmaceutical composition comprising hydrocodone and acetaminophen that provides a rapid onset of analgesia, and reduced levels of acetaminophen near the end of the dosing interval. Also provided are methods for reducing the risk of acetaminophen-induced hepatic damage in a subject being treated with an acetaminophen containing composition, as well as methods for treating pain in a subject in need thereof.

27 Claims, 22 Drawing Sheets

Related U.S. Application Data

(60) Provisional application No. 61/487,047, filed on May 17, 2011, provisional application No. 61/537,527, filed on Sep. 21, 2011, provisional application No. 61/606,850, filed on Mar. 5, 2012, provisional application No. 61/537,533, filed on Sep. 21, 2011, provisional application No. 61/606,896, filed on Mar. 5, 2012.

(51) Int. Cl.
    *A61K 51/12* (2006.01)
    *A61K 9/24* (2006.01)
    *A61K 31/167* (2006.01)
    *A61K 31/485* (2006.01)

(52) U.S. Cl.
    CPC .......... *A61K 31/167* (2013.01); *A61K 31/485* (2013.01); *A61K 51/1258* (2013.01)

(56) References Cited

U.S. PATENT DOCUMENTS

| | | |
|---|---|---|
| 4,894,236 A | 1/1990 | Jang |
| 4,996,058 A | 2/1991 | Sinnreich |
| 5,075,114 A | 12/1991 | Roche |
| 5,266,331 A | 11/1993 | Oshlack et al. |
| 5,273,758 A | 12/1993 | Royce |
| 5,336,691 A | 8/1994 | Raffa et al. |
| 5,443,843 A | 8/1995 | Curatolo et al. |
| 5,478,577 A | 12/1995 | Sackler et al. |
| 5,508,042 A | 4/1996 | Oshlack et al. |
| 5,549,912 A | 8/1996 | Oshlack et al. |
| 5,582,837 A | 12/1996 | Shell |
| 5,626,874 A | 5/1997 | Conte et al. |
| 5,651,985 A | 7/1997 | Penners et al. |
| 5,656,295 A | 8/1997 | Oshlack et al. |
| 5,672,360 A | 9/1997 | Sackler et al. |
| 5,783,212 A | 7/1998 | Fassihi et al. |
| 5,866,161 A | 2/1999 | Childers et al. |
| 5,876,759 A | 3/1999 | Gowan, Jr. |
| 5,891,471 A | 4/1999 | Miller et al. |
| 5,945,123 A | 8/1999 | Hermelin |
| 5,945,125 A | 8/1999 | Kim |
| 5,958,459 A | 9/1999 | Chasin et al. |
| 5,965,161 A | 10/1999 | Oshlack et al. |
| 5,965,163 A | 10/1999 | Miller et al. |
| 5,965,167 A | 10/1999 | Sanghvi et al. |
| 5,968,551 A | 10/1999 | Oshlack et al. |
| 5,972,389 A | 10/1999 | Shell et al. |
| 5,980,882 A | 11/1999 | Eichman |
| 6,024,982 A | 2/2000 | Oshlack et al. |
| 6,068,855 A | 5/2000 | Leslie et al. |
| 6,071,208 A | 6/2000 | Koivunen |
| 6,103,219 A | 8/2000 | Sherwood et al. |
| 6,103,261 A | 8/2000 | Chasin et al. |
| 6,120,803 A | 9/2000 | Wong et al. |
| 6,126,969 A | 10/2000 | Shah et al. |
| 6,143,322 A | 11/2000 | Sackler et al. |
| 6,210,714 B1 | 4/2001 | Oshlack et al. |
| 6,245,357 B1 | 6/2001 | Edgren et al. |
| 6,251,430 B1 | 6/2001 | Zhang et al. |
| 6,254,887 B1 | 7/2001 | Miller et al. |
| 6,340,475 B2 | 1/2002 | Shell et al. |
| 6,372,254 B1 | 4/2002 | Ting et al. |
| 6,375,957 B1 | 4/2002 | Kaiko et al. |
| 6,387,404 B2 | 5/2002 | Oshlack et al. |
| 6,488,962 B1 | 12/2002 | Berner et al. |
| 6,488,963 B1 | 12/2002 | McGinity et al. |
| 6,500,459 B1 | 12/2002 | Chhabra et al. |
| 6,599,529 B1 | 7/2003 | Skinhøj et al. |
| 6,635,280 B2 | 10/2003 | Shell et al. |
| 6,667,060 B1 | 12/2003 | Vandecruys et al. |
| 6,682,759 B2 | 1/2004 | Lim et al. |
| 6,696,066 B2 | 2/2004 | Kaiko et al. |
| 6,706,281 B2 | 3/2004 | Oshlack et al. |
| 6,723,340 B2 | 4/2004 | Gusler et al. |
| 6,730,321 B2 | 5/2004 | Ting et al. |
| 6,733,783 B2 | 5/2004 | Oshlack et al. |
| 6,797,283 B1 | 9/2004 | Edgren et al. |
| 6,852,336 B2 | 2/2005 | Hunter et al. |
| 6,902,742 B2 | 6/2005 | Devane et al. |
| 7,074,430 B2 | 7/2006 | Miller et al. |
| 7,144,587 B2 | 12/2006 | Oshlack et al. |
| 7,201,920 B2 | 4/2007 | Kumar et al. |
| 7,374,781 B2 | 5/2008 | Zhang et al. |
| 7,405,238 B2 | 7/2008 | Markey et al. |
| 7,413,751 B2 | 8/2008 | Devane et al. |
| 7,438,927 B2 | 10/2008 | Berner et al. |
| 7,514,100 B2 | 4/2009 | Oshlack et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,691,873 B2 | 4/2010 | Duncalf et al. |
| 7,776,314 B2 | 8/2010 | Bartholomaus et al. |
| 7,846,476 B2 | 12/2010 | Oshlack et al. |
| 7,897,172 B2 | 3/2011 | Qasem et al. |
| 7,939,543 B2 | 5/2011 | Kupper |
| 7,943,170 B2 | 5/2011 | Chan et al. |
| 7,976,870 B2 | 7/2011 | Berner et al. |
| 8,075,872 B2 | 12/2011 | Arkenau-Maric et al. |
| 8,309,060 B2 | 11/2012 | Bartholomaus et al. |
| 8,337,888 B2 | 12/2012 | Wright et al. |
| 8,394,408 B2 | 3/2013 | Han et al. |
| 8,409,616 B2 | 4/2013 | Kumar et al. |
| 8,465,776 B2 | 6/2013 | Hoarau |
| 8,597,681 B2 | 12/2013 | Park et al. |
| 8,658,631 B1 | 2/2014 | Devarakonda et al. |
| 8,741,885 B1 | 6/2014 | Devarakonda et al. |
| 8,790,694 B2 | 7/2014 | Devarakonda et al. |
| 8,858,963 B1 | 10/2014 | Devarakonda et al. |
| 8,980,319 B2 | 3/2015 | Park et al. |
| 8,992,975 B2 | 3/2015 | Devarakonda et al. |
| 9,050,335 B1 | 6/2015 | Devarakonda et al. |
| 2001/0008639 A1 | 7/2001 | Oshlack et al. |
| 2001/0031278 A1 | 10/2001 | Oshlack |
| 2002/0018810 A1 | 2/2002 | Oshlack et al. |
| 2002/0058050 A1 | 5/2002 | Sackler et al. |
| 2002/0192277 A1 | 12/2002 | Oshlack et al. |
| 2003/0035837 A1 | 2/2003 | Sackler et al. |
| 2003/0044466 A1 | 3/2003 | Markey et al. |
| 2003/0064099 A1 | 4/2003 | Oshlack |
| 2003/0068371 A1 | 4/2003 | Oshlack |
| 2003/0091635 A1 | 5/2003 | Baichwal et al. |
| 2003/0092724 A1 | 5/2003 | Kao et al. |
| 2003/0099704 A1 | 5/2003 | Oshlack et al. |
| 2003/0104062 A1 | 6/2003 | Berner et al. |
| 2003/0125347 A1 | 7/2003 | Anderson et al. |
| 2004/0096500 A1 | 5/2004 | Oshlack et al. |
| 2004/0105887 A1 | 6/2004 | Oshlack et al. |
| 2004/0131671 A1 | 7/2004 | Zhang et al. |
| 2004/0156899 A1 | 8/2004 | Louie-Helm et al. |
| 2005/0013863 A1 | 1/2005 | Lim et al. |
| 2005/0020613 A1 | 1/2005 | Boehm et al. |
| 2005/0031546 A1 | 2/2005 | Bartholomaus et al. |
| 2005/0089570 A1 | 4/2005 | Cruz et al. |
| 2005/0106249 A1 | 5/2005 | Hwang et al. |
| 2005/0112195 A1 | 5/2005 | Cruz et al. |
| 2005/0158382 A1 | 7/2005 | Cruz et al. |
| 2005/0165038 A1 | 7/2005 | Gordon |
| 2005/0232987 A1 | 10/2005 | Srinivasan et al. |
| 2005/0266032 A1 | 12/2005 | Srinivasan et al. |
| 2005/0267189 A1 | 12/2005 | Gao et al. |
| 2006/0002860 A1 | 1/2006 | Bartholomaus et al. |
| 2006/0057210 A1 | 3/2006 | Oshlack et al. |
| 2006/0099255 A1 | 5/2006 | Oshlack et al. |
| 2006/0165791 A1 | 7/2006 | Oshlack et al. |
| 2006/0193782 A1 | 8/2006 | Bartholomaus et al. |
| 2006/0205752 A1 | 9/2006 | Whitehead |
| 2006/0240105 A1 | 10/2006 | Devane et al. |
| 2006/0251721 A1 | 11/2006 | Cruz et al. |
| 2006/0263436 A1 | 11/2006 | Baert et al. |
| 2006/0269604 A1 | 11/2006 | Sackler et al. |
| 2006/0292214 A1 | 12/2006 | Jenkins et al. |
| 2007/0020335 A1 | 1/2007 | Chen et al. |

(56) References Cited

U.S. PATENT DOCUMENTS

| | | |
|---|---|---|
| 2007/0048228 A1 | 3/2007 | Arkenau-Maric et al. |
| 2007/0059359 A1 | 3/2007 | Backensfeld et al. |
| 2007/0128279 A1 | 6/2007 | Edgren et al. |
| 2007/0183980 A1 | 8/2007 | Arkenau-Maric et al. |
| 2007/0184112 A1 | 8/2007 | Wong et al. |
| 2007/0190142 A1 | 8/2007 | Breitenbach et al. |
| 2007/0207200 A1 | 9/2007 | Plachetka et al. |
| 2007/0237833 A1 | 10/2007 | Sackler et al. |
| 2007/0259033 A1 | 11/2007 | Cruz |
| 2007/0259045 A1 | 11/2007 | Mannion et al. |
| 2007/0275065 A1 | 11/2007 | Oshlack et al. |
| 2007/0281018 A1 | 12/2007 | Qiu et al. |
| 2008/0020039 A1 | 1/2008 | Parikh et al. |
| 2008/0031901 A1 | 2/2008 | Qiu et al. |
| 2008/0031963 A1 | 2/2008 | Sackler et al. |
| 2008/0044482 A1 | 2/2008 | Oshlack et al. |
| 2008/0057122 A1* | 3/2008 | Toney-Parker et al. ...... 424/468 |
| 2008/0113025 A1 | 5/2008 | Devane et al. |
| 2008/0132532 A1 | 6/2008 | Wright et al. |
| 2008/0138422 A1 | 6/2008 | Staniforth |
| 2008/0220062 A1 | 9/2008 | Ashton |
| 2009/0022798 A1 | 1/2009 | Rosenberg et al. |
| 2009/0028941 A1 | 1/2009 | Cowles et al. |
| 2009/0068269 A1 | 3/2009 | Oshlack et al. |
| 2009/0081290 A1 | 3/2009 | McKenna et al. |
| 2009/0149479 A1 | 6/2009 | Jenkins et al. |
| 2009/0155357 A1 | 6/2009 | Muhuri |
| 2009/0175937 A1 | 7/2009 | Rahmouni et al. |
| 2009/0202629 A1 | 8/2009 | Oshlack et al. |
| 2009/0304793 A1 | 12/2009 | Boehm |
| 2009/0306119 A1 | 12/2009 | Keane |
| 2009/0311320 A1 | 12/2009 | Oury et al. |
| 2009/0317355 A1 | 12/2009 | Roth et al. |
| 2009/0324714 A1 | 12/2009 | Liu et al. |
| 2010/0010030 A1 | 1/2010 | Jain et al. |
| 2010/0015222 A1 | 1/2010 | Han et al. |
| 2010/0034876 A1 | 2/2010 | Oshlack et al. |
| 2010/0040681 A1 | 2/2010 | Park et al. |
| 2010/0092570 A1 | 4/2010 | Oshlack et al. |
| 2010/0168148 A1 | 7/2010 | Wright et al. |
| 2010/0172974 A1 | 7/2010 | Oshlack et al. |
| 2010/0172989 A1 | 7/2010 | Roth et al. |
| 2010/0196425 A1 | 8/2010 | Cruz et al. |
| 2010/0196471 A1 | 8/2010 | Jain et al. |
| 2010/0196474 A1 | 8/2010 | Han et al. |
| 2010/0216829 A2 | 8/2010 | Kumar et al. |
| 2010/0221293 A1 | 9/2010 | Cruz et al. |
| 2010/0239662 A1 | 9/2010 | Rahmouni et al. |
| 2010/0260833 A1 | 10/2010 | Bartholomaus et al. |
| 2011/0020451 A1 | 1/2011 | Bartholomaus et al. |
| 2011/0038927 A1 | 2/2011 | Oshlack et al. |
| 2011/0038930 A1 | 2/2011 | Barnscheid et al. |
| 2011/0052685 A1 | 3/2011 | Hou et al. |
| 2011/0077238 A1 | 3/2011 | Leech et al. |
| 2011/0117196 A1 | 5/2011 | Gordon |
| 2011/0118189 A1 | 5/2011 | Farr et al. |
| 2011/0129507 A1 | 6/2011 | Cruz |
| 2011/0150969 A1 | 6/2011 | Shah et al. |
| 2011/0150970 A1 | 6/2011 | Shah et al. |
| 2011/0150971 A1 | 6/2011 | Shah et al. |
| 2011/0150989 A1 | 6/2011 | Park et al. |
| 2011/0150990 A1 | 6/2011 | Shah et al. |
| 2011/0150991 A1 | 6/2011 | Shah et al. |
| 2011/0159046 A1 | 6/2011 | Cruz |
| 2011/0166171 A1 | 7/2011 | Qiu et al. |
| 2011/0177168 A1 | 7/2011 | Chan et al. |
| 2011/0195116 A1 | 8/2011 | Hobbs et al. |
| 2011/0195989 A1 | 8/2011 | Rudnic et al. |
| 2011/0207762 A1 | 8/2011 | Chapman et al. |
| 2011/0212173 A1 | 9/2011 | Young et al. |
| 2011/0229526 A1 | 9/2011 | Rosenberg et al. |
| 2011/0229533 A1 | 9/2011 | Edgren et al. |
| 2011/0262532 A1 | 10/2011 | Oshlack et al. |
| 2011/0287095 A1 | 11/2011 | Park et al. |
| 2011/0301129 A1 | 12/2011 | Berner et al. |
| 2011/0318392 A1 | 12/2011 | Cruz et al. |
| 2012/0321713 A1 | 12/2012 | Han et al. |
| 2013/0273153 A1 | 10/2013 | Park et al. |
| 2014/0170217 A1 | 6/2014 | Devarakonda et al. |
| 2014/0275143 A1 | 9/2014 | Devarakonda et al. |
| 2014/0288113 A1 | 9/2014 | Devarakonda et al. |
| 2014/0294956 A1 | 10/2014 | Devarakonda et al. |
| 2016/0184299 A1 | 6/2016 | Devarakonda et al. |

FOREIGN PATENT DOCUMENTS

| | | |
|---|---|---|
| WO | 97/18814 A1 | 5/1997 |
| WO | 9747285 A1 | 12/1997 |
| WO | 98/55107 A1 | 12/1998 |
| WO | 9856360 A2 | 12/1998 |
| WO | 9947128 A1 | 9/1999 |
| WO | 03/024426 A1 | 3/2003 |
| WO | 2005013863 A2 | 2/2005 |
| WO | 2005030182 A1 | 4/2005 |
| WO | 2006022759 A1 | 3/2006 |
| WO | 2006071208 A1 | 7/2006 |
| WO | 2008015220 A1 | 2/2008 |
| WO | 2008015221 A2 | 2/2008 |
| WO | 2009049405 A1 | 4/2009 |
| WO | 2009076764 A1 | 6/2009 |
| WO | 2009114648 A1 | 9/2009 |
| WO | 2009135846 A1 | 11/2009 |
| WO | 2010032128 A1 | 3/2010 |
| WO | 2010069050 A1 | 6/2010 |
| WO | 2010078486 A2 | 7/2010 |
| WO | 2010141505 A1 | 12/2010 |
| WO | 2011009603 A1 | 1/2011 |
| WO | 2011009604 A1 | 1/2011 |
| WO | 2011068723 A1 | 6/2011 |
| WO | 2011077451 A2 | 6/2011 |
| WO | 2011/087765 A2 | 7/2011 |
| WO | 2011106416 A2 | 9/2011 |
| WO | 2012007159 A2 | 1/2012 |
| WO | 2012/087377 A1 | 6/2012 |
| WO | 2014/149397 A1 | 9/2014 |

OTHER PUBLICATIONS

*Mallinckrodt LLC, et al.* v. *Watson Laboratories, Inc.,* Case No. 2:15v3800 (New Jersey)—Answer to Complaint dated Sep. 11, 2015 [D.I. 14].
*Mallinckrodt LLC, et al.* v. *Watson Laboratories, Inc.,* Case No. 2:15v3800 (New Jersey)—Actavis and Watson's Motion to Dismiss dated Sep. 11, 2015 [D.I. 16].
*Mallinckrodt LLC, et al.* v. *Watson Laboratories, Inc.,* Case No. 2:15v3800 (New Jersey)—US District Court Civil Docket dated Jun. 16, 2016 (12 pages).
*Mallinckrodt LLC, et al.* v. *Watson Laboratories, Inc.,* Case No. 2:15v3800 (New Jersey)—Redaction to Actavis and Watson's Memorandum in Support of Motion to Dismiss dated Sep. 11, 2015 [D.I. 18].
*Mallinckrodt LLC, et al.* v. *Watson Laboratories, Inc.,* Case No. 2:15v3800 (New Jersey)—Order Adjourning Actavis and Watson' Motion to Dismiss dated Sep. 29, 2015 [D.I. 27].
*Mallinckrodt LLC, et al.* v. *Watson Laboratories, Inc.,* Case No. 2:15v3800 (New Jersey)—Order re Schedule as to Motion to Dismiss dated Oct. 7, 2015 [D.I. 29].
*Mallinckrodt LLC, et al.* v. *Watson Laboratories, Inc.,* Case No. 2:15v3800 (New Jersey)—Stipulation and Order Directing Plaintiffs to File Their Amended Complaint by Nov. 2, 2015 dated Oct. 30, 2015 [D.I. 36].
*Mallinckrodt LLC, et al.* v. *Watson Laboratories, Inc.,* Case No. 2:15v3800 (New Jersey)—Mallinckrodt's Amended Complaint dated Nov. 2, 2015 [D.I. 37].
*Mallinckrodt LLC, et al.* v. *Watson Laboratories, Inc.,* Case No. 2:15v3800 (New Jersey)—Actavis' Amended Answer to Amended Complaint dated Nov. 17, 2015 [D.I. 39].
*Mallinckrodt LLC, et al.* v. *Watson Laboratories, Inc.,* Case No. 2:15v3800 (New Jersey)—Mallinckrodt's Answer to Counterclaim dated Dec. 2, 2015 [D.I. 43].

(56) References Cited

OTHER PUBLICATIONS

*Mallinckrodt LLC, et al.* v. *Watson Laboratories, Inc.,* Case No. 2:15v3800 (New Jersey)—Discovery Confidentiality Order dated Jan. 4, 2016 [D.I. 46].
*Mallinckrodt LLC, et al.* v. *Par Pharmaceuticals Inc.,* Case No. 2:15v7694 (New Jersey)—Complaint dated Oct. 23, 2015 [D.I. 1] (Separated into three parts).
*Mallinckrodt LLC, et al.* v. *Par Pharmaceuticals Inc.,* Case No. 2:15v7694 (New Jersey)—US District Court Civil Docket dated Jun. 16, 2016 (3 pages).
Moroni, et al., Application of Poly(oxyethylene) Homopolymers in Sustained Release Solid Formulations, Drug Development and Industrial Pharmacy, 21(12):1411-1428 (1995).
Maggi, "Dissolution Behavior of Hydrophilic Matrix Tablets Containing Two Different Polyethylene Oxides (PEOs) for the Controlled Release of a Water-Soluble Drug Dimensionality Study," Biomaterials, 23:1113-1119 (2002).
Apicella, et al., "Poly(ethylene oxide) (PEO) and different molecular weight PEO blends monolithic devices for drug release, Biomaterials," 14:83-90 (1993).
Gatti, A., et al., "Oxycodone/Paracetamol: A Low Dose Synergic Combination Useful in Different Types of Pain," Clin. Drug Investig. 2010, 30 Suppl. 2:3-14.
Siewert, M., "FIP Guidelines for Dissolution Testing of Solid Oral Products," Pharm. Ind. 57:362-369 (1995).
Turnbull, K., et al., "Stability of Oxycodone Hydrochloride for Injection in Dextrose and Saline Solutions," Can. J. Hosp. Pharm. (55), 2002: 272-77.
*Mallinckrodt LLC, et al.* v. *Watson Laboratories, Inc.,* Case No. 2:15v3800 (New Jersey)—Joint Claim Construction and Prehearing Statement dated May 16, 2016 [D.I. 64].
*Mallinckrodt LLC, et al.* v. *Watson Laboratories, Inc.,* Case No. 2:15v3800 (New Jersey)—Stipulation of Voluntary Dismissal of Claims and Counterclaims Pertaining to U.S. Pat. No. 8,597,681; 8,980,319; 7,976,870; 8,668,929; 3,372,432; 8,377,453; and 8,394,408 dated May 25, 2016 [D.I. 66].
*Mallinckrodt LLC, et al.* v. *Par Pharmaceuticals Inc.,* Case No. 2:15v7694 (New Jersey)—Notice of Dismissal of Action dated Apr. 15, 2016 [D.I. 19].
Final Office Action dated Jan. 14, 2016 and received in U.S. Appl. No. 14/187,939 (20 pages).
Final Office Action dated Jan. 14, 2016 and received in U.S. Appl. No. 14/188,582 (22 pages).
Non-Final Office Action dated Jun. 12, 2015 and received in U.S. Appl. No. 14/187,939 (35 pages).
Non-Final Office Action dated Jun. 12, 2015 and received in U.S. Appl. No. 14/188,582 (63 pages).
Non-Final Office Action dated May 21, 2015 and received in U.S. Appl. No. 14/301,658 (10 pages).
Non-Final Office Action dated Jul. 20, 2015 and received in U.S. Appl. No. 14/627,879 (6 pages).
Non-Final Office Action dated Apr. 22, 2016 and received in U.S. Appl. No. 14/659,819 (10 pages).
Unpublished U.S. Appl. No. 15/147,621 filed on May 5, 2016.
Waterman K. C.; "A Critical Review of Gastric Retentive Controlled Drug Delivery;" Pharmaceutical Development and Technology; (2007); 12; pp. 1-10.
Arora et al.; "Floating Drug Delivery Systems: A Review;" AAPS PharmSciTech; (2005); 6(3); Article 47 E372-390.
Klausner et al.; "Novel Gastroretentive Dosage Forms: Evaluation of Gastroretentivity and Its Effect on Levodopa Absorption in Humans;" Pharmaceutical Research; ( 2003); vol. 20; No. 9; pp. 1466-1473.
Klausner et al.; "Novel Levodopa Gastroretentive Dosage Form: in-Vivo Evaluation in Dogs;" Journal of Controlled Release; (2003); 88; pp. 117-126.
Aulton M. E.; "Aulton's Pharmaceutics: The Design And Manufacture of Medicines;" Elsevier Limited; Oxford; Third Edition; (2007); pp. 270-278.
Prinderre et al.; "Advances in Gastro Retentive Drug-Delivery Systems;" Expert Opin. Drug. Deliv.; (2011); 8(9); pp. 1189-1203.
Berner et al.; "Case Studies in Swelling Polymeric Gastric Retentive Tablets;" Expert Opin. Drug. Deliv.; (2006); 3(4), pp. 541-548.
Ward et al.; "Modeling the Economic and Health Consequences of Managing Chronic Osteoarthritis Pain with Opioids in Germany: Comparison of Extended Release Oxycodone and OROS Hydromorphone;" Current Medical Research and Opinion; (2007); vol. 23; No. 10; pp. 2333-2345.
Koizumi et al.; "Efficacy and Tolerability of Cancer Pain Management with Controlled-Release Oxycodone Tablets in Opioid-Naive Cancer Pain Patients, Starting with 5 mg Tablets;" Jpn J Clin Oncol; (2004); 34(10); pp. 608-614.
Gammaitoni et al.; "Effectiveness and Safety of New Oxycodone/Acetaminophen Formulations With Reduced Acetaminophen for the Treatment of Low Back Pain;" Pain Medicine; (2003); vol. 4; No. 1; pp. 21-30.
U.S. Appl. No. 14/627,879, filed Feb. 20, 2015; not yet published.
XARTEMIS™ XR Prescribing Information, revised Mar. 2014 (28 pages).
Requirement for Restriction/Election received in U.S. Appl. No. 13/166,770 and dated Jun. 22, 2012 (6 pages).
Non-Final Office Action received in U.S. Appl. No. 13/166,770 and dated Nov. 26, 2012 (14 pages).
Non-Final Office Action received in U.S. Appl. No. 14/092,375 and dated Feb. 24, 2014 (11 pages).
Requirement for Restriction/Election received in U.S. Appl. No. 13/473,563 and dated Sep. 11, 2012 (5 pages).
Non-Final Office Action received in U.S. Appl. No. 13/473,563 and dated May 6, 2013 (20 pages).
Non-Final Office Action received in U.S. Appl. No. 14/109,052 and dated Apr. 25, 2014 (6 pages).
Final Office Action received in U.S. Appl. No. 14/109,052 and dated Aug. 11, 2014 (7 pages).
Requirement for Restriction/Election received in U.S. Appl. No. 13/473,586 and dated Mar. 28, 2013 (6 pages).
Non-Final Office Action received in U.S. Appl. No. 13/473,586 and dated Aug. 2, 2013 (9 pages).
Non-Final Office Action received in U.S. Appl. No. 13/473,586 and dated Jun. 19, 2014 (7 pages).
Non-Final Office Action received in U.S. Appl. No. 13/473,571 and dated Aug. 31, 2012 (11 pages).
Final Office Action received in U.S. Appl. No. 13/473,571 and dated May 15, 2013 (16 pages).
Requirement for Restriction/Election received in U.S. Appl. No. 13/473,584 and dated Jun. 18, 2013 (15 pages).
Non-Final Office Action received in U.S. Appl. No. 13/473,584 and dated Oct. 24, 2013 (14 pages).
Final Office Action received in U.S. Appl. No. 13/473,584 and dated Aug. 20, 2014 (14 pages).
Non-Final Office Action received in U.S. Appl. No. 13/473,578 and dated Mar. 26, 2013 (11 pages).
Final Office Action received in U.S. Appl. No. 13/473,578 and dated Dec. 17, 2013 (7 pages).
Requirement for Restriction/Election received in U.S. Appl. No. 14/187,939 and dated Jan. 23, 2015 (7 pages).
Requirement for Restriction/Election received in U.S. Appl. No. 14/188,582 and dated Jan. 29, 2015 (7 pages).
Non-Final Office Action received in U.S. Appl. No. 12/973,962 and dated Feb. 24, 2012 (13 pages).
Final Office Action received in U.S. Appl. No. 12/973,962 and dated Sep. 21, 2012 (15 pages).
Advisory Action received in U.S. Appl. No. 12/973,962 and dated Dec. 5, 2012 (3 pages).
Non-Final Office Action received in U.S. Appl. No. 12/973,962 and dated Jun. 19, 2014 (17 pages).
Requirement for Restriction/Election received in U.S. Appl. No. 13/995,810 and dated Dec. 22, 2014 (10 pages).
Final Office Action received in U.S. Appl. No. 12/973,962 and dated Apr. 20, 2015 (20 pages).
Banfai et al.; "Content Uniformity and Assay Requirements in Current Regulations;" J. Chromatogr. A.; (2007); 1156; pp. 206-212.

(56) References Cited

OTHER PUBLICATIONS

Zhu et al.; "Solid-State Plasticization of an Acrylic Polymer with Chlorpheniramine Maleate and Triethyl Citrate;" International Journal of Pharmaceutics; (2002); 241; pp. 301-310.
Nimmo, et al.; "Inhibition of Gastric Emptying and Drug Absorption by Narcotic Analgesics;" Br. J. Clin. Pharmac.; (1975); 2; pp. 509-513.
Altaf et al.; "Bead Compacts II. Evaluation of Rapidly Disintegrating Nonsegregating Compressed Bead Formulations;" Drug Development and Industrial Pharmacy; (1999); 25(5); pp. 635-642.
International Search Report from Application No. PCT/US2010/061400 with a mailing date of Nov. 25, 2011 (4 pages).
U.S. Department of Health & Human Services; "FDA Drugs Safety Communication: Prescription Acetaminophen Products to be Limited to 325mg per Dosage Unit; Boxed Warning Will Highlight Potential for Severe Liver Failure;" (5 pages); Downloaded on Feb. 9, 2012 from: http://www.fda.gov/Drugs/DrugSafetv/ucm239821.htm.
"Tylenol Professional Product Information;" (2010); McNeil Consumer Healthcare (62 pages).
Oxycontin; Description and Patient Information; (2010); Purdue Pharma L.P. (32 pages).
Khosla et al.; "The Effect of Tablet Size on the Gastric Emptying of Non-Disintegrating Tablets;" International Journal of Pharmaceutics; (1990); 62; R9-R11.
Khosla et al.; "Gastrointestinal Transit of Non-Disintegrating Tablets in Fed Subjects;" International Journal of Pharmaceutics; (1989); 53; pp. 107-117.
Davis et al.; "The Gastrointestinal Transit of a Controlled Release Formulation of Indomethacin;" International Journal of Pharmaceutics; (1990); 60; pp. 191-196.
Brzeznicka et al.; "Dynamics of Glutathione Levels in Liver and Indicatory Enzymes in Serum in Acetaminophen Intoxication in Mice;" Polish Journal of Occupational Medicine; (1989); vol. 2; No. 1; pp. 15-22.
Gammaitoni et al.; "Randomized, Double-Blind, Placebo-Controlled Comparison of the Analgesic Efficacy of Oxycodone 10 mg/Acetaminophen 325 mg versus Controlled-Release Oxycodone 20 mg in Postsurgical Pain;" J. Clin. Pharmacol; (2003); 43; pp. 296-304.
Moller et al.; "Time to Onset of Analgesia and Analgesic Efficacy of Effervescent Acetaminophen 1000 mg Compared to Tablet Acetaminophen 1000 mg in Postperative Dental Pain: A Single-Dose, Double-Blind, Randomized, Placebo-Controlled Study;" J. Clin. Pharmacol.; (2000); 40; pp. 370-378.
Nielsen et al; "Analgesic Efficacy of Immediate and Sustained Release Paracetamol and Plasma Concentration of Paracetamol. Double Blind Placebo-Controlled Evaluation Using Painful Laser Stimulation;" Eur. J. Clin Pharmacol; (1992); 42; pp. 261-264.
James et al; "Acetaminophen-Induced Hepatotoxicity;" Drug Metabolism and Disposition; (2003); vol. 31; No. 12; pp. 1499-1506.
Mirochnitchenko et al.; "Acetaminophen Toxicity: Opposite Effects of Two Forms of Glutathione Peroxidase;" The Journal of Biological Chemistry; (1999); vol. 274; No. 15; pp. 10349-10355.
Dart et al.; "Acetaminophen Poisoning: An Evidence-Based Consensus Guideline for Out-of-Hospital Management;" Clinical Toxicology; (2006); 44; pp. 1-18.
Bolesta et al.; "Hepatotoxicity Associated with Chronic Acetaminophen Administration in Patients without Risk Factors"; The Annals of Pharmacotherapy; (2002); vol. 36; pp. 331-333.
Rinaldi et al.; "Minireview: Reactive Intermediates and the Dynamics of Glutathione Transferases;" Drug Metabolism and Deposition; (2002); vol. 30; No. 10; pp. 1053-1058.
Barry H. Rumack; "Acetaminophen Hepatotoxicity: The First 35 Years;" Clinical Toxicology; (2002); 40(1); pp. 3-20.
Bartels et al.; "Are Recommended Doses of Acetaminophen Hepatotoxic for Recently Abstinent Alcoholics? A Randomized Trial"; (2008); Clinical Toxicology; 46; pp. 243-249.

Corcoran et al.; "Role of Glutathione in Prevention of Acetaminophen-Induced Hepatotoxicity by N-Acetyl-L-Cysteine in Vivo: Studies with N-Acetyl-D-Cysteine in Mice;" The Journal of Pharmacology and Experimental Therapeutics; (1986); vol. 238; No. 1; pp. 54-61.
Davis et al.; "Species Differences in Hepatic Glutathione Depletion, Covalent Binding and Hepatic Necrosis After Acetaminophen;" Life Sciences; vol. 14; pp. 2099-2109.
Mitchell et al.; "Acetaminophen-Induced Hepatic Necrosis. IV. Protective Role of Glutathione;" The Journal of Pharmacology and Experimental Therapeutics; (1973); vol. 187; No. 1; pp. 211-217.
Kaplowitz et al.; "Drug-Induced Liver Disease;" (2003); Marcel Dekker, Inc.; Chapters 13 and 15; pp. 287-325 and pp. 345-375.
Skoglund et al.; "Efficacy of Paracetamol-Esterified Methionine Versus Cysteine or Methionine on Paracetamol-Induced Hepatic GSH Depletion and Plasma ALAT Level in Mice;" Biochemical Pharmacology; (1986); vol. 35; No. 18; pp. 3071-3075.
Talukder et al; "Gastroretentive Delivery Systems: A Mini Review;" Drug Development and Industrial Pharmacy; (2004); vol. 30; No. 10; pp. 1019-1028.
Hou et al; "Gastric Retentive Dosage Forms: A Review"; Critical Reviews in Therapeutic Drug Carrier Systems; (2003); 20(6); pp. 461-497.
Streubel et al.; "Drug Delivery to the Upper Small Intestine Window Using Gastroretentive Technologies;" Current Opinion in Pharmacology; (2006); vol. 6; pp. 501-508.
Streubel et al. "Gastroretentive Drug Delivery Systems"; Expert Opin. Drug Deliv.; (2006); 3(2); pp. 217-233.
Moes, A. J.; "Gastroretentive Dosage Forms;" Critical Reviews in Therapeutic Drug Carrier Systems; (1993); 10(2); pp. 143-195.
Davis S. S.; "Formulation Strategies for Absorption Windows;" DDT; (2005); vol. 10, No. 4; pp. 249-257.
Bardonnet et al.; "Gastroretentive Dosage Forms: Overview and Special Case of Helicobacter Pylori;" Journal of Controlled Release; (2006); vol. 111; pp. 1-18.
U.S. Appl. No. 13/473,584, filed May 16, 2012; not yet published.
U.S. Appl. No. 13/473,586, filed May 16, 2012; not yet published.
"Foremost NF Fast Flo Lactose: Modified, Spray Dried, Product Code 316; A Spray-Dried Mixture of Crystalline and Amorphose Lactose;" Foremost Farms; USA; (1 page). Online Article downloaded from the site: http://www.foremostfarms.com/Commercial/pdfs/Specifications/TDS_NF_Lactose_316.pdf Document created on Jan. 28, 2010.
Freed et al.; "pH Control on Nucleophilic/Electrophilic Oxidation;" Int. J. Pharm.; (2008); vol. 357; pp. 180-188.
International Search Report for PCT Patent application No. PCT/US2009/036864 mailed on Aug. 31, 2009.
Lab Basics Technical Library; Particle Size Conversion Table; Sigma-Aldrich; 3 pages; online article downloaded from the site: http://www.sigmaaldrich.comichemistiy/stockroom-reagents/learning-center/technical-library/particle-size-conversion. printerview.html on Apr. 17, 2012.
Polyox Water-Soluble Resins, Technical Data, "Degradation of Water-Soluble Resins"; Form 326-00027-1002AMS (2002).
Polyox Water-Soluble Resins, Technical Data, "Water-Soluble Resin Storage Stability;" Form 326-00044-0704MAB (2004).
Waterman et al.; "Stabilization of Pharmaceuticals to Oxidative Degradation;" Pharmaceutical Development and Technology; (2002); vol. 7; No. 1; pp. 1-32.
Zhang et al.; "Effect of Processing Methods and Heat Treatment on the Formation of Wax Matrix Tablets for Sustained Drug Release;" Pharmaceutical Development and Technology; (2001); vol. 6; No. 2; pp. 131-144.
Meert et al.; A Preclinical Comparison Between Different Opioids: Antinociceptive Versus Adverse Effects; Pharmacology, Biochemistry and Behavior; (2005); 80; pp. 309-326.
Doteuchi et al.; "Pharmacological Studies of Oxycodone Hydrochloride: 1. Antinociceptive Effect and General Pharmacology"; Oyo Yakuri/Pharmacometrics; (1995); 49(3); pp. 257-273.
Miller et al.; "Physical and Chemical Characteristics of Some High Purity Magnesium Stearate and Palmitate Powders;" International Journal of Pharmaceutics; (1985); 23; pp. 55-67.

(56) References Cited

OTHER PUBLICATIONS

Kim, C.-J.; "Effects of Drug Solubility, Drug Loading, and Polymer Molecular Weight on Drug Release from Polyox Tablets;" Drug Development and Industrial Pharmacy; (1998); 24(7); pp. 645-651.

* cited by examiner

TAMPER RESISTANT COMPOSITION COMPRISING HYDROCODONE AND ACETAMINOPHEN FOR RAPID ONSET AND EXTENDED DURATION OF ANALGESIA

RELATED CASES

This application claims priority to U.S. patent application Ser. No. 13/473,578 filed on May 16, 2012 which claims priority to U.S. Provisional Application No. 61/487,047 filed on May 17, 2011, U.S. Provisional Application Nos. 61/537,533 and 61/537,527 filed on Sep. 21, 2011, and U.S. Provisional Application Nos. 61/606,896 and 61/606,850 filed on Mar. 5, 2012, which are incorporated herein by reference in their entirety to the full extent permitted by law.

FIELD OF THE INVENTION

The present disclosure relates to an extended release pharmaceutical composition comprising hydrocodone and acetaminophen that provides a rapid onset of analgesia, followed by an extended duration of analgesia of about 12 hours.

BACKGROUND OF THE INVENTION

Oral drug administration remains the route of choice for the majority of clinical applications. Modified release (MR) dosage forms that are administered once or twice daily offer advantages over their immediate release (IR) counterparts because they reduce the magnitude of peaks and troughs of drug plasma concentration, provide longer dosing intervals, sustained analgesic effect, and increased patient compliance. These modified release formulations may be referred to as controlled release (CR), sustained release (SR) and/or extended release (ER) etc. For certain types of patients, such as those suffering from pain, these MR products may permit the patient to sleep through the night without having to wake up during the night to take the next dose. Thus, it can significantly increase the quality of life for such patients. Both IR and MR products for pain are widely available in the market. Examples of IR products include those containing NSAIDs, opioids, profens, COX II inhibitors and aspirin (Tylenol, Advil, Celebrex, Vioxx, Aleve, Voltaren). Examples of MR products include those containing NSAIDs and opioids (Tylenol SR, Oxycontin).

Researchers have also combined various classes of pain drugs to provide better analgesia to patients. For example, a combination of acetaminophen-hydrocodone bitartrate is commercially available as Vicodin, and acetaminophen-oxycodone hydrochloride is commercially available as Percocet. In randomized controlled trials, it was shown that the combination product Percocet was statistically superior to MR hydrocodone in various outcome measures of pain relief. Other combination products such as acetaminophen-tramadol are either available or described in the literature. It is postulated that the combination of two analgesic drugs with complementary mechanisms of action results in enhanced analgesia due to an additive effect, an "opioid-sparing" effect, and an improved side effect and safety profile. The improved safety profile results from the use of reduced doses of two analgesics with different side-effects rather than an equieffective dose of a single agent.

Acetaminophen is absorbed from the small intestine and primarily metabolized by conjugation, like glucuronidation and sulfation, in the liver to nontoxic, water-soluble compounds that are eliminated in the urine. When the maximum daily dose is exceeded over a prolonged period, metabolism by conjugation becomes saturated, and excess acetaminophen is oxidatively metabolized by cytochrome P450 (CYP) enzymes (e.g., CYP2E1, 1A2, 2A6, 3A4) to a reactive metabolite, N-acetyl-p-benzoquinone-imine (NAPQI). NAPQI is a reactive free radical with an extremely short half-life that is rapidly inactivated by conjugation with glutathione, which is acting as a sulfhydryl donor. Once the pool of available glutathione is exhausted, the cysteines of cellular proteins become sulfhydryl donors to NAPQI, binding covalently and initiating a cascade of oxidative and cellular damage, resulting in necrosis and, ultimately, liver failure. Thus, avoiding excessive NAPQI formation is an important strategy when using acetaminophen, although to date acetaminophen-sparing has not been an approach any manufacturers have chosen to take. However, due to the prevalence of acetaminophen in many over-the-counter products, it is prudent to consider acetaminophen-sparing precautions when considering combination therapy lasting more than a few days to avoid an inadvertent reduction in glutathione stores.

Thus, various options for pain management are available that are both IR and MR, and contain either a single drug or a combination of analgesics. While these combination products provide the benefits associated with combining two analgesics as described above, both IR and MR, in itself, have a significant disadvantage. IR combination products lack the advantages of MR products described previously. MR combination products lack a significant benefit associated with IR products—rapid onset of analgesia—that is extremely desirable for pain management. Because MR products retard the rate of drug release to sustain the drug effect over prolonged period, release of drug is slow resulting in significant time before effective analgesic drug concentration is attained in the bloodstream. There exists a clinical need for pain management that combines the desirable features of IR and MR in combination pain products.

SUMMARY OF THE INVENTION

Among the various aspects of the present disclosure is a pharmaceutical composition for extended release of hydrocodone and acetaminophen comprising at least one extended release portion comprising hydrocodone, acetaminophen or a combination thereof, and at least one extended release component. The composition, when orally administered to a subject, maintains a therapeutic plasma concentration of hydrocodone of at least about 5 ng/mL from about 0.75 hour to about 10 hours after administration of the composition. Additionally, at least about 90% of the acetaminophen is released from the composition by about 8 hours after administration of the composition such that, by about 10 hours after administration of the composition, acetaminophen has a blood plasma concentration that is less than about 30% of acetaminophen's maximum plasma concentration.

A further aspect of the disclosure encompasses a pharmaceutical composition for extended release of hydrocodone and acetaminophen comprising (a) at least one immediate release portion comprising hydrocodone, acetaminophen or a combination thereof, and (b) at least one extended release portion comprising hydrocodone, acetaminophen or a combination thereof, and an extended release component, wherein about 30% of the hydrocodone in the pharmaceutical composition is released in about 15 minutes and at least about 90% of the acetaminophen in the pharmaceutical composition is released in about 8 hours when measured in 900 ml of 0.1N HCl using a USP type II apparatus at a paddle speed of about 150 rpm and a constant temperature of 37° C.

Yet another aspect of the disclosure is a pharmaceutical composition for extended release of hydrocodone and acetaminophen, comprising at least one extended release portion comprising hydrocodone or a pharmaceutically acceptable salt thereof, acetaminophen, and an extended release component; wherein upon administration to a subject in need thereof, the composition provides an $AUC_{0-1.27h}$ for acetaminophen of about 3 ng·h/mL/mg to about 13 ng·h/mL/mg; an $AUC_{1.27-36h}$ for acetaminophen of about 20 ng·h/mL/mg to about 75 ng·h/mL/mg; an $AUC_{0-2.4h}$ for hydrocodone or salt of about 0.5 ng·h/mL/mg to about 5 ng·h/mL/mg; and $AUC_{2.4-36h}$ for hydrocodone or salt of about 5 ng·h/mL/mg to about 25 ng·h/mL/mg.

A further aspect of the disclosure is a pharmaceutical composition for oral administration in the treatment of pain, comprising at least one extended release portion comprising hydrocodone or a pharmaceutically acceptable salt thereof, acetaminophen, and an extended release component, wherein when the composition is administered to a subject in need thereof, the subject attains therapeutic blood levels of both the hydrocodone and the acetaminophen within about one hour after administration of the composition and maintains analgesia for about 12 hours after administration of the composition. Further, upon placement of the composition in an in vitro dissolution test comprising USP Paddle Method at a paddle speed of about 100 rpm in 900 ml of 0.1 N HCl using a USP type II apparatus at a constant temperature of 37° C., no more than about 65%, by weight, of the total amount of the hydrocodone or salt is released and no more than about 80%, by weight, of the total amount of the acetaminophen is released by 2 hours; from about 65% to about 85%, by weight, of the total amount of the hydrocodone or salt is released and from about 65% to about 95%, by weight, of the total amount of the acetaminophen is released after 4 hours; from about 80% to about 100%, by weight, of the total amount of the hydrocodone or salt is released and from about 80% to about 100%, by weight, of the total amount of the acetaminophen is released after 8 hours; and about 85% to about 100%, by weight, of the total amount of the hydrocodone or salt is released and from about 85% to about 100%, by weight, of the total amount of the acetaminophen is released after 12 hours.

Still another aspect of the disclosure provides a dosage form comprising (a) an immediate release portion comprising acetaminophen and hydrocodone, wherein the immediate release portion comprises, by weight of the immediate release portion, from about 70% to about 80% of acetaminophen and from about 0.5% to about 1% of hydrocodone; and (b) an extended release portion comprising acetaminophen, hydrocodone, and an extended release polymer, wherein the extended release portion comprises, by weight of the extended release portion, from about 20% to about 40% of acetaminophen, from about 0.5% to about 2% of hydrocodone, and from about 30% to about 50% of the extended release polymer.

Another aspect provides a dosage form comprising from about 7.5 mg to about 30 mg of hydrocodone and from about 325 mg to about 650 mg of acetaminophen. The dosage form comprises (a) at least one immediate release portion comprising about 25% of the total amount of hydrocodone in the composition and about 50% of the total amount of acetaminophen in the composition; and (b) at least one extended release portion comprising about 75% of the total amount of hydrocodone in the composition, about 50% of the total amount of acetaminophen in the composition, and about 35% to about 45%, by weight of the at least one extended release portion, of an extended release polymer comprising a polyethylene oxide.

A further aspect of the disclosure provides a method for reducing the risk of acetaminophen-induced hepatic damage in a subject being treated for pain with a dosage regimen that comprises administering to the subject at least two consecutive doses of a pharmaceutical composition comprising hydrocodone and acetaminophen. The method comprises (a) administering a first dose of the pharmaceutical composition comprising at least one extended release portion comprising acetaminophen, hydrocodone or a combination thereof, and an extended release component to the subject, wherein the composition maintains a therapeutic blood plasma concentration of hydrocodone of at least 5 ng/mL from about 0.75 hours to about 10 hours after administration of the composition, and wherein at least about 90% of the acetaminophen is released from the composition by about 8 hours after administration of the composition such that, by about 10 hours after administration of the composition, acetaminophen has a blood plasma concentration that is less than about 30% of acetaminophen's maximum plasma concentration; and (b) administering a second dose of the pharmaceutical composition to the subject at about 12 hours after administration of the first dose.

Yet another aspect of the disclosure encompasses a method for treating pain in a subject in need thereof with a pharmaceutical composition that comprises hydrocodone and acetaminophen. The method comprises orally administering to the subject an effective amount of the pharmaceutical composition comprising at least one extended release portion comprising hydrocodone, acetaminophen or a combination thereof, and an extended release component, wherein the composition maintains a therapeutic plasma concentration of hydrocodone of at least about 5 ng/mL from about 0.75 hour to about 10 hours after administration of the composition, and wherein at least about 90% of the acetaminophen is released from the composition by about 8 hours after administration of the composition such that, by about 10 hours after administration of the composition, acetaminophen has a blood plasma concentration that is less than about 30% of acetaminophen's maximum plasma concentration.

Other features and aspects of the disclosure are described in detail below.

Treatment A (formulation A) was a single, two-tablet dose containing a total of 15 mg hydrocodone and 650 mg acetaminophen having slow release properties as compared to formulation B, administered orally under fasted conditions. Treatment B (formulation B) was a single, two-tablet dose containing a total of 15 mg hydrocodone and 650 mg acetaminophen having faster release properties as compared to formulation A, administered orally under fasted conditions. Treatment C (formulation B) was a single, two-tablet dose containing a total of 15 mg hydrocodone and 650 mg acetaminophen administered orally under fed conditions. Treatment D was one tablet of an immediate release 7.5 hydrocodone/325 acetaminophen tablet administered orally every 6 hours for 2 doses under fasted conditions.

Figure 1:
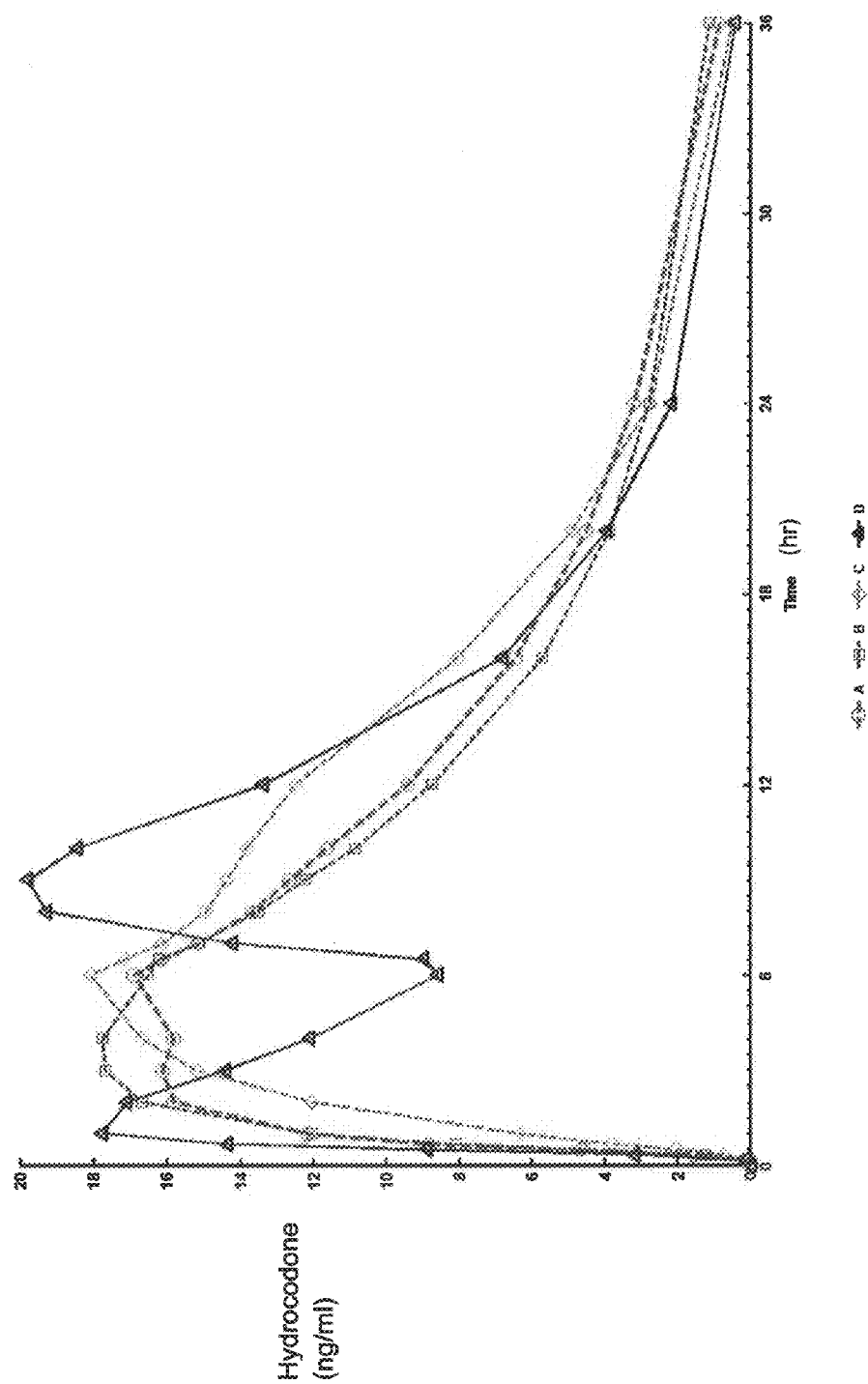
FIG. 1 presents the mean plasma concentrations of hydrocodone versus time by treatment for 0 to 36 hours. Treatment A (formulation A) was a single, two-tablet dose containing a total of 15 mg hydrocodone and 650 mg acetaminophen having slow release properties as compared to formulation B, administered orally under fasted conditions. Treatment B (formulation B) was a single, two-tablet dose containing a total of 15 mg hydrocodone and 650 mg acetaminophen having faster release properties as compared to formulation A, administered orally under fasted conditions. Treatment C (formulation B) was a single, two-tablet dose containing a total of 15 mg hydrocodone and 650 mg acetaminophen administered orally under fed conditions. Treatment D was one tablet of an immediate release 7.5 hydrocodone/325 acetaminophen tablet administered orally every 6 hours for 2 doses under fasted conditions.
Figure 3:
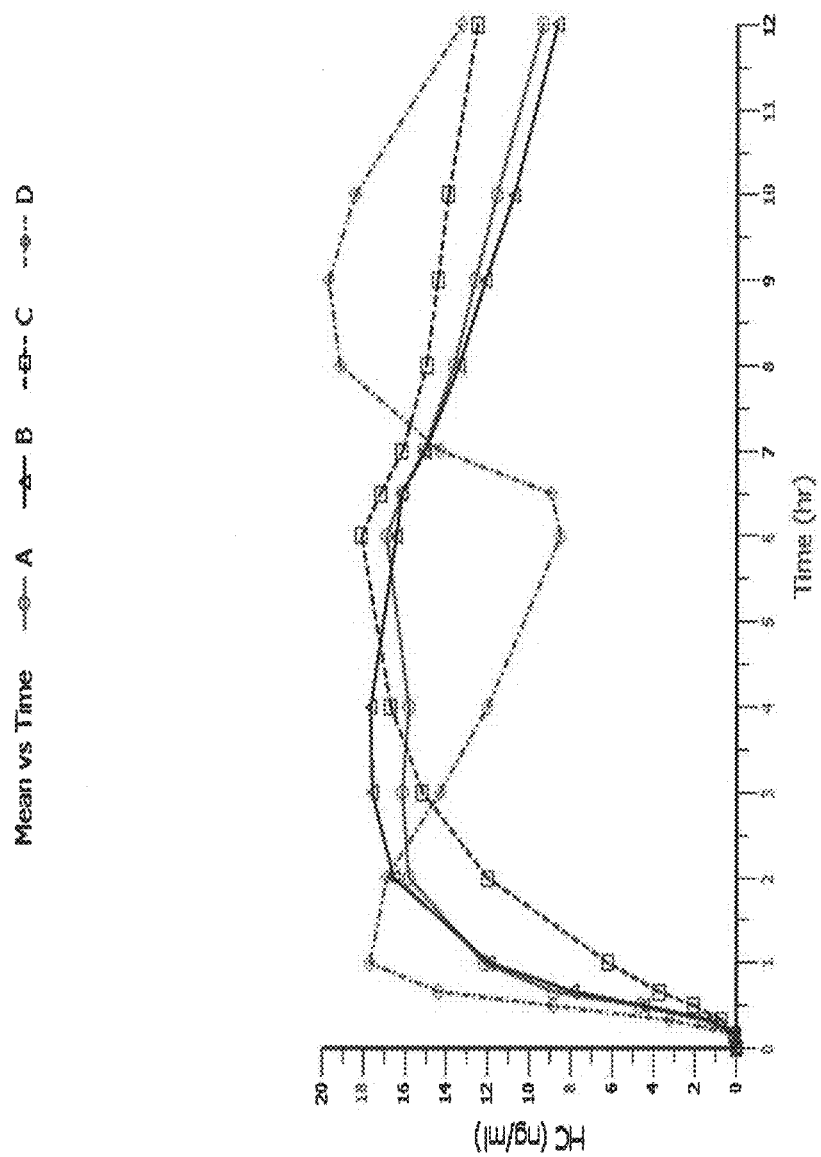

FIG. 3 presents the mean plasma concentrations of hydrocodone versus time by treatment as indicated in FIG. 1, but represented for 0 to 12 hours.

Figure 2:
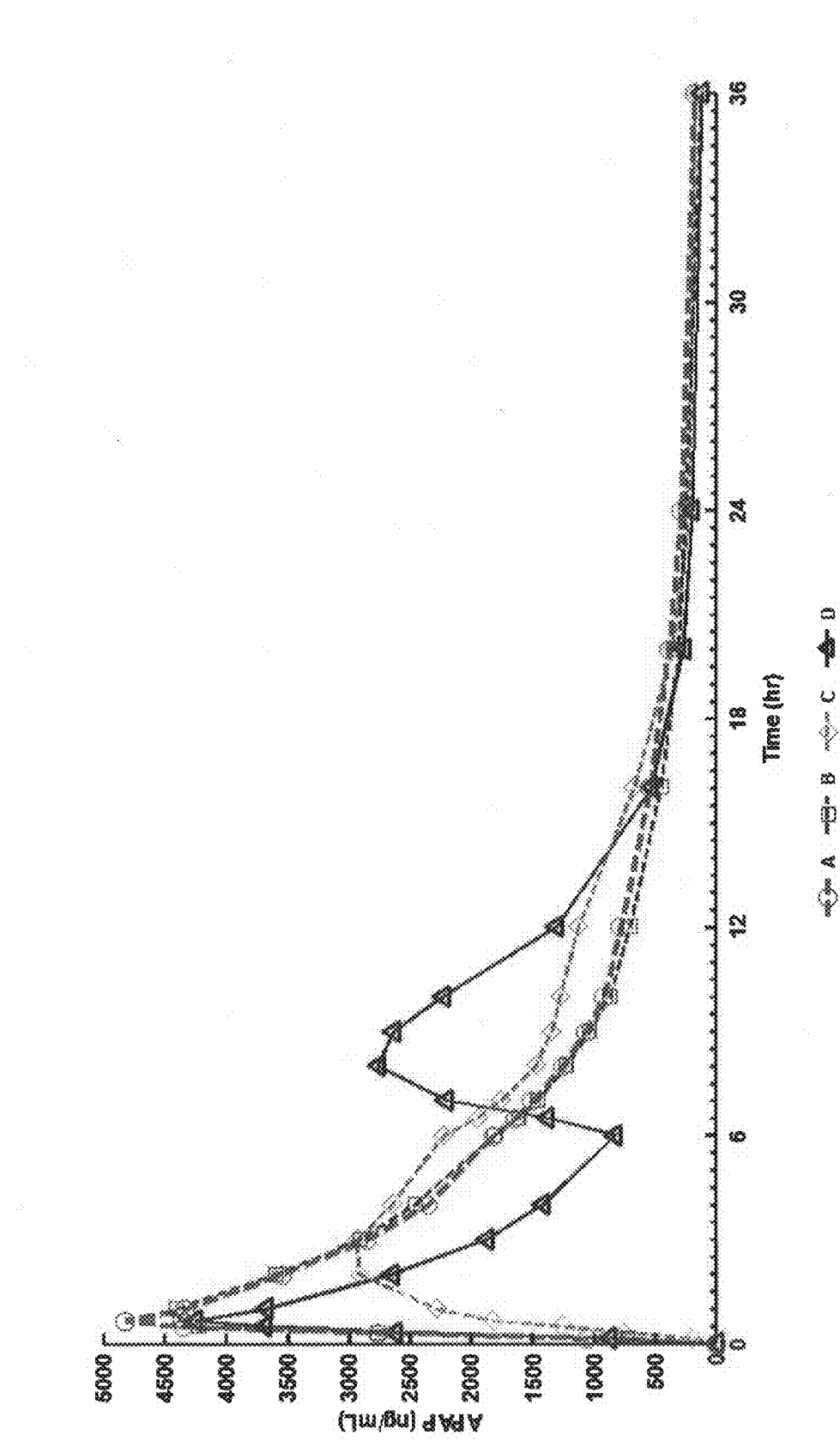
FIG. 2 presents the mean plasma concentrations of acetaminophen versus time by treatment for 0 to 36 hours.
Figure 4:
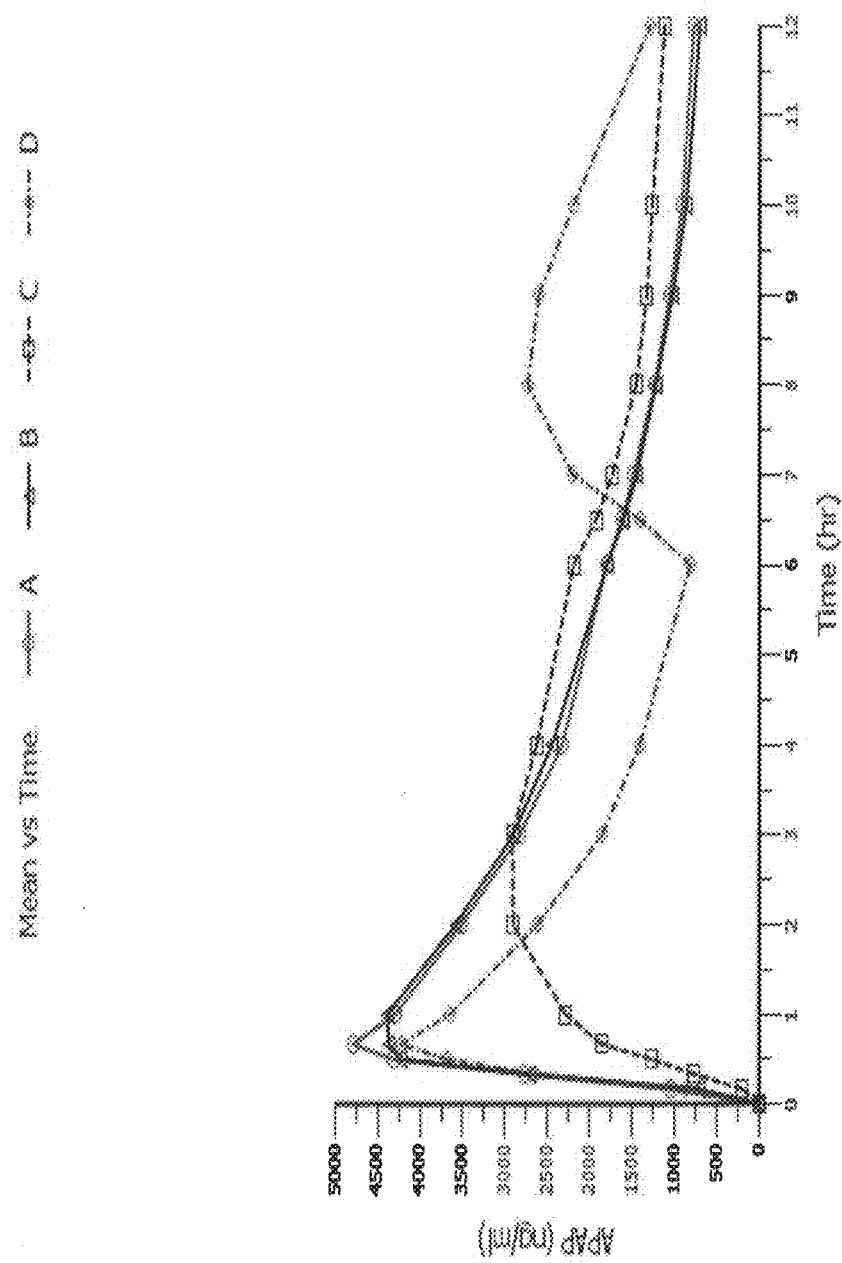

FIG. 4 presents the mean plasma concentrations of acetaminophen versus time by treatment as indicated in FIG. 2, but represented for 0 to 12 hours.

Figure 5:
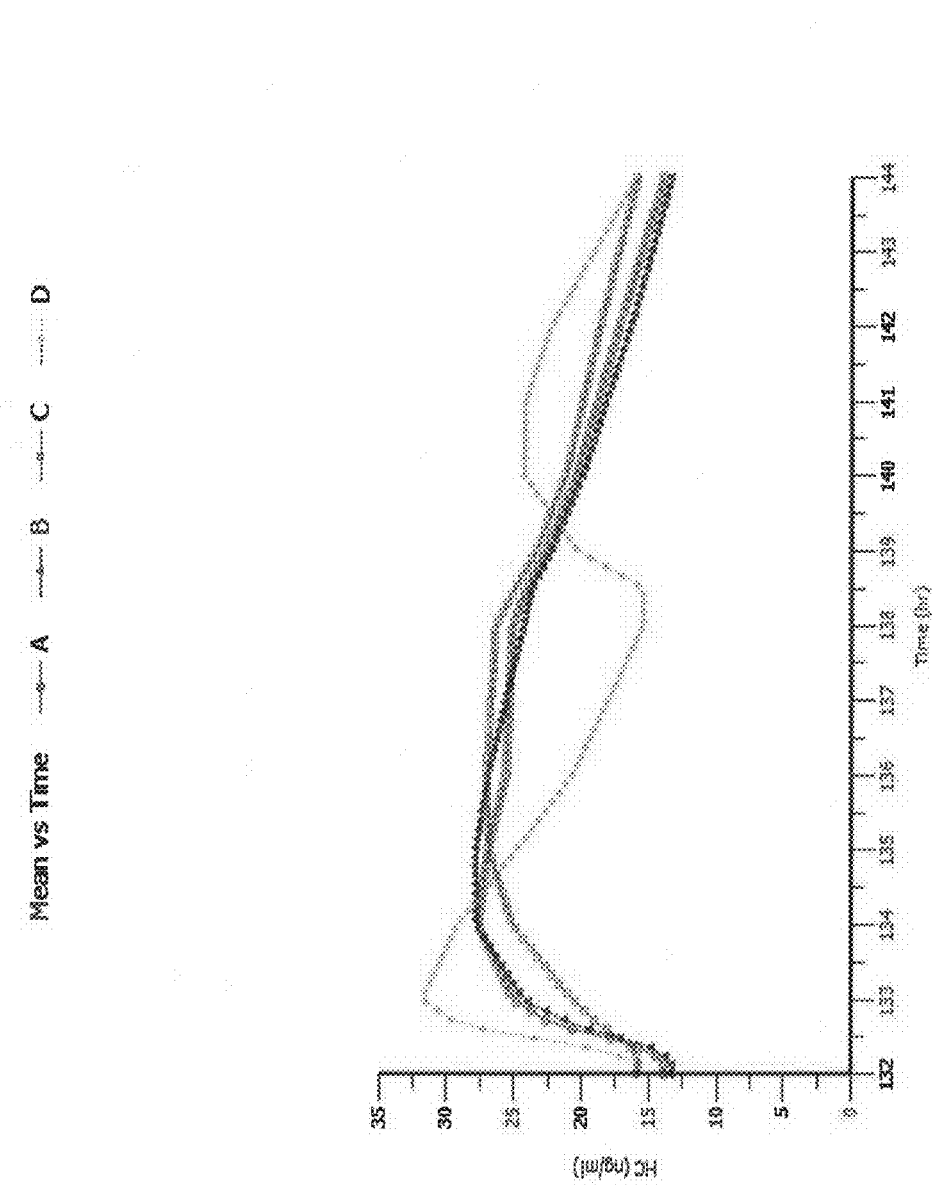

FIG. 5 presents simulated hydrocodone pharmacokinetic profiles at steady state versus time by treatment for 0 to 144 hours for Treatments A, B, C, and D of Example 1.

Figure 6:
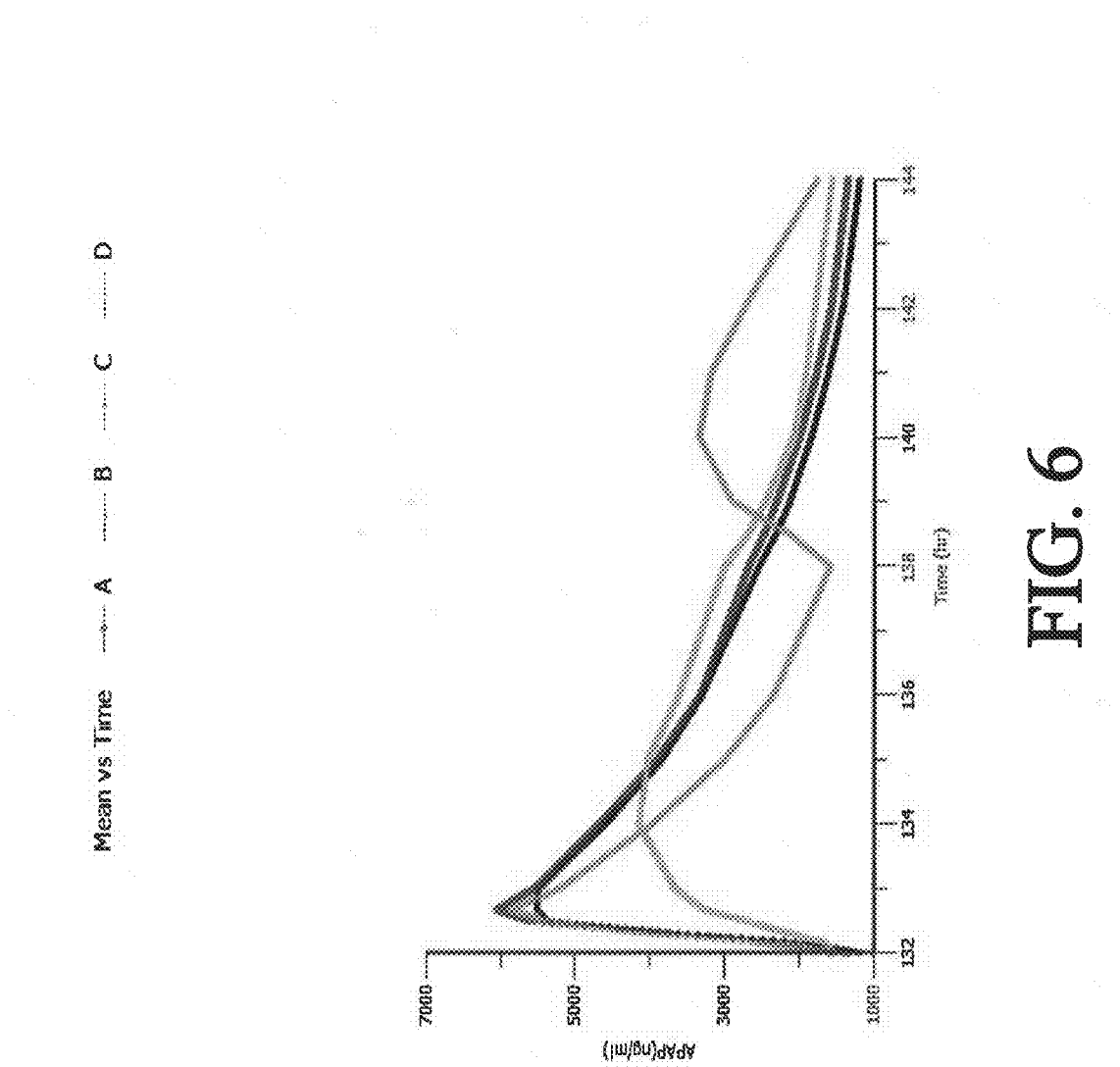

FIG. 6 presents simulated acetaminophen pharmacokinetic profiles at steady state versus time by treatment for 0 to 144 hours for Treatments A, B, C, and D of Example 1.

Figure 7:
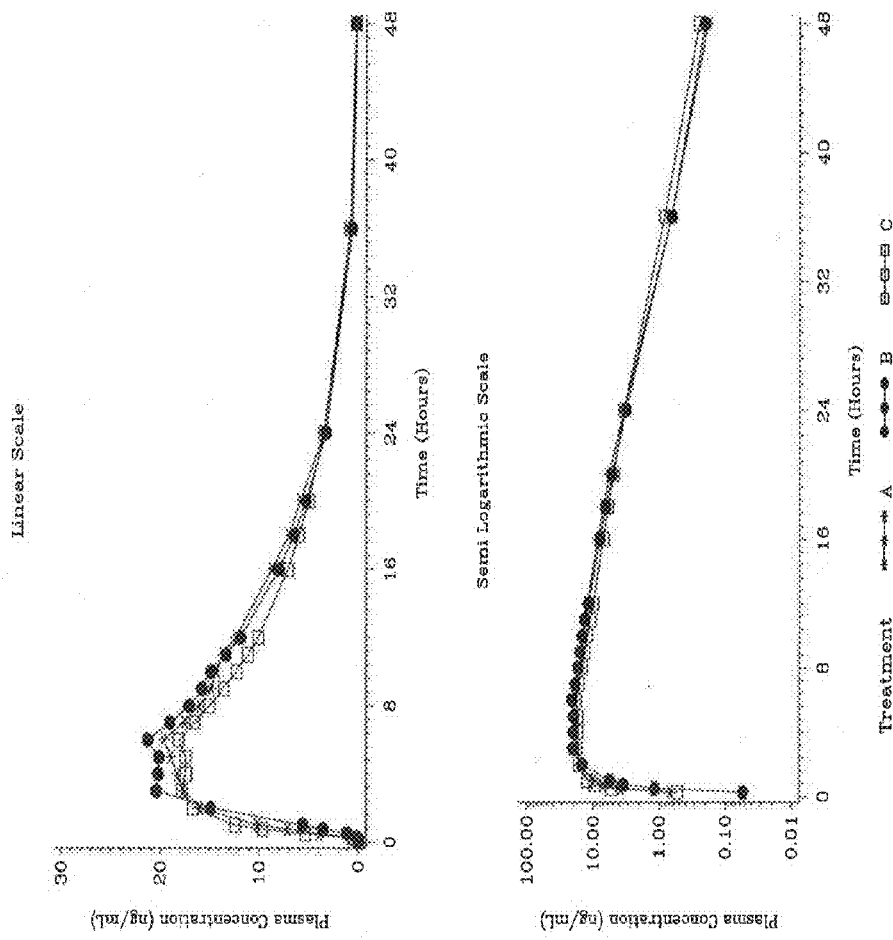

FIG. 7 presents mean plasma concentrations of hydrocodone as a function of time by treatment following oral administration of two tablets of 7.5 mg of hydrocodone and 325 mg of acetaminophen. Treatment A was under fed (high fat) conditions. Treatment B was under fed (low fat) conditions. Treatment C was under fasted conditions.

Figure 8:
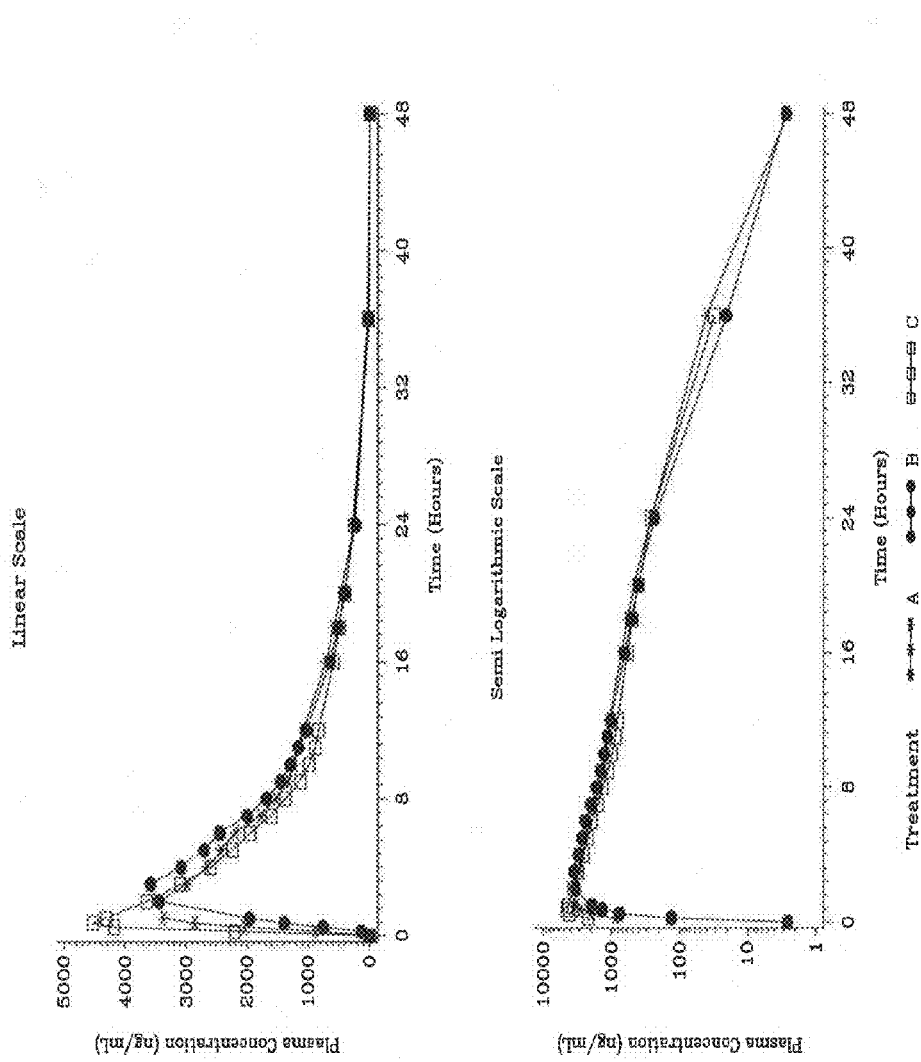

FIG. 8 presents mean plasma concentrations of acetaminophen as a function of time by treatment following oral administration of two tablets of 7.5 mg of hydrocodone and 325 mg of acetaminophen. Treatment A was under fed (high fat) conditions. Treatment B was under fed (low fat) conditions. Treatment C was under fasted conditions.

Figure 9:
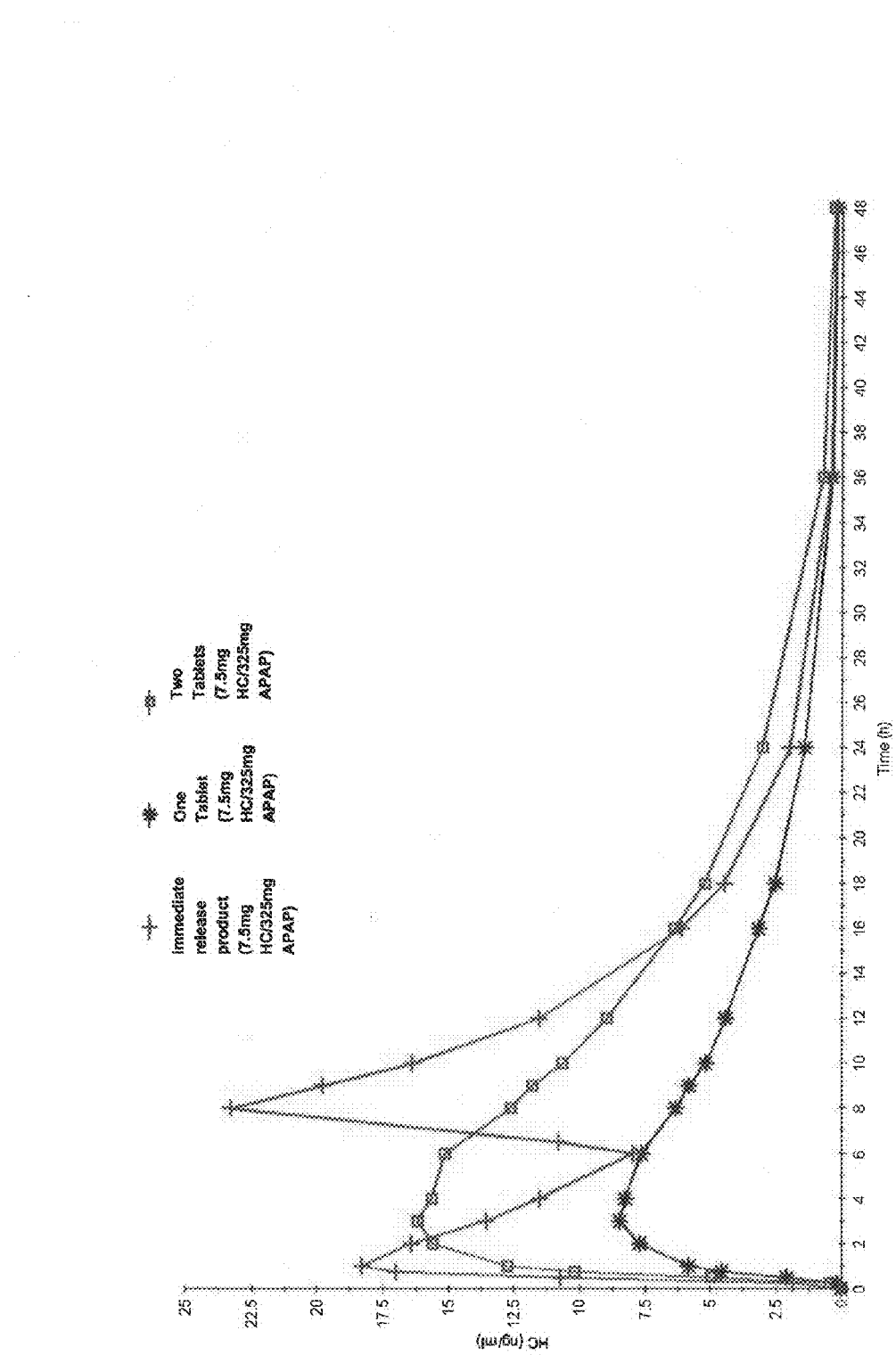

FIG. 9 presents mean plasma concentrations of hydrocodone as a function of time by treatment following oral administration of a single dose of Treatments A, B, and C of Example 3.

Figure 10:
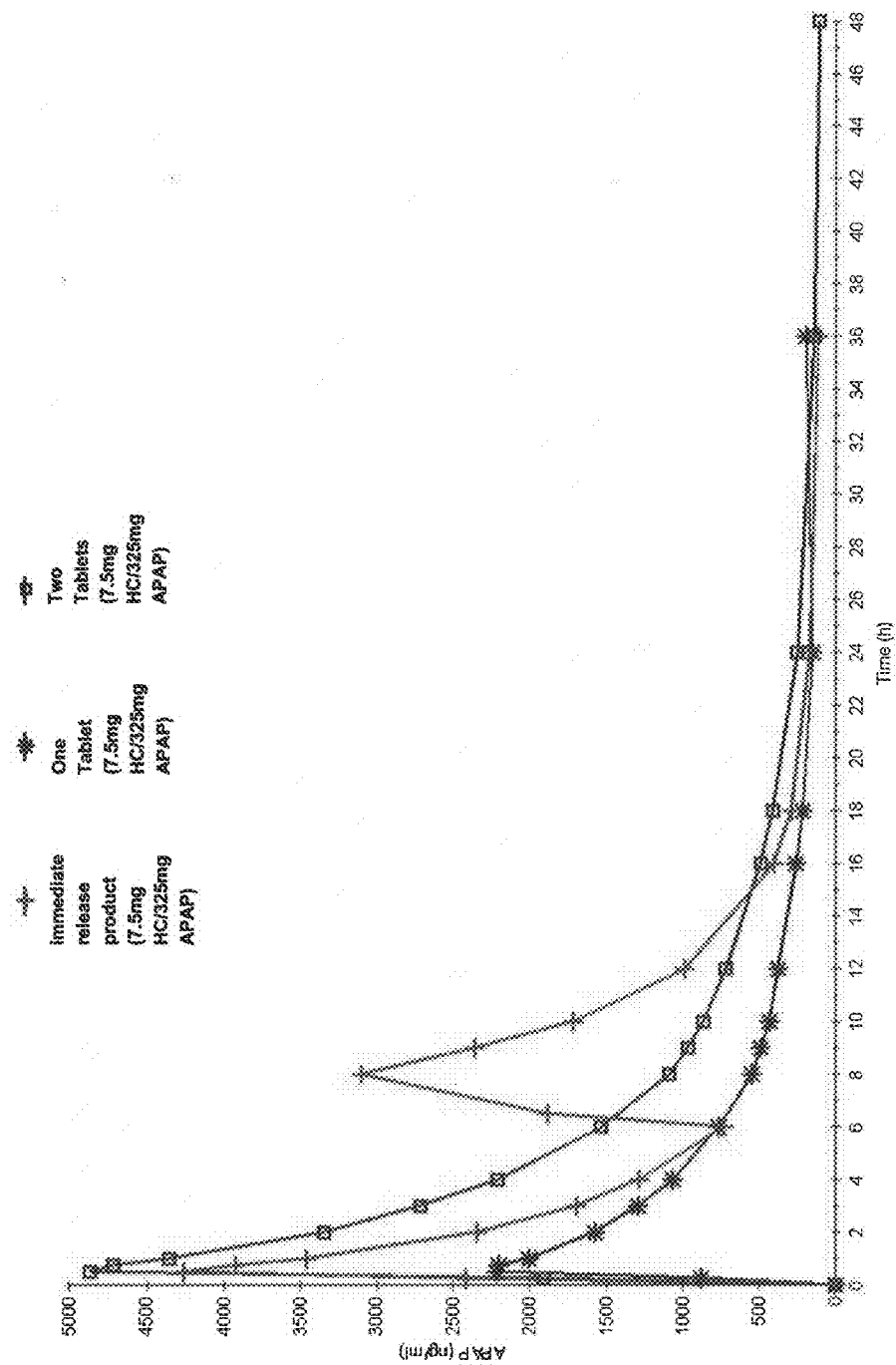

FIG. 10 presents mean plasma concentrations of acetaminophen as a function of time by treatment following oral administration of a single dose of Treatments A, B, and C of Example 3.

Figure 11:
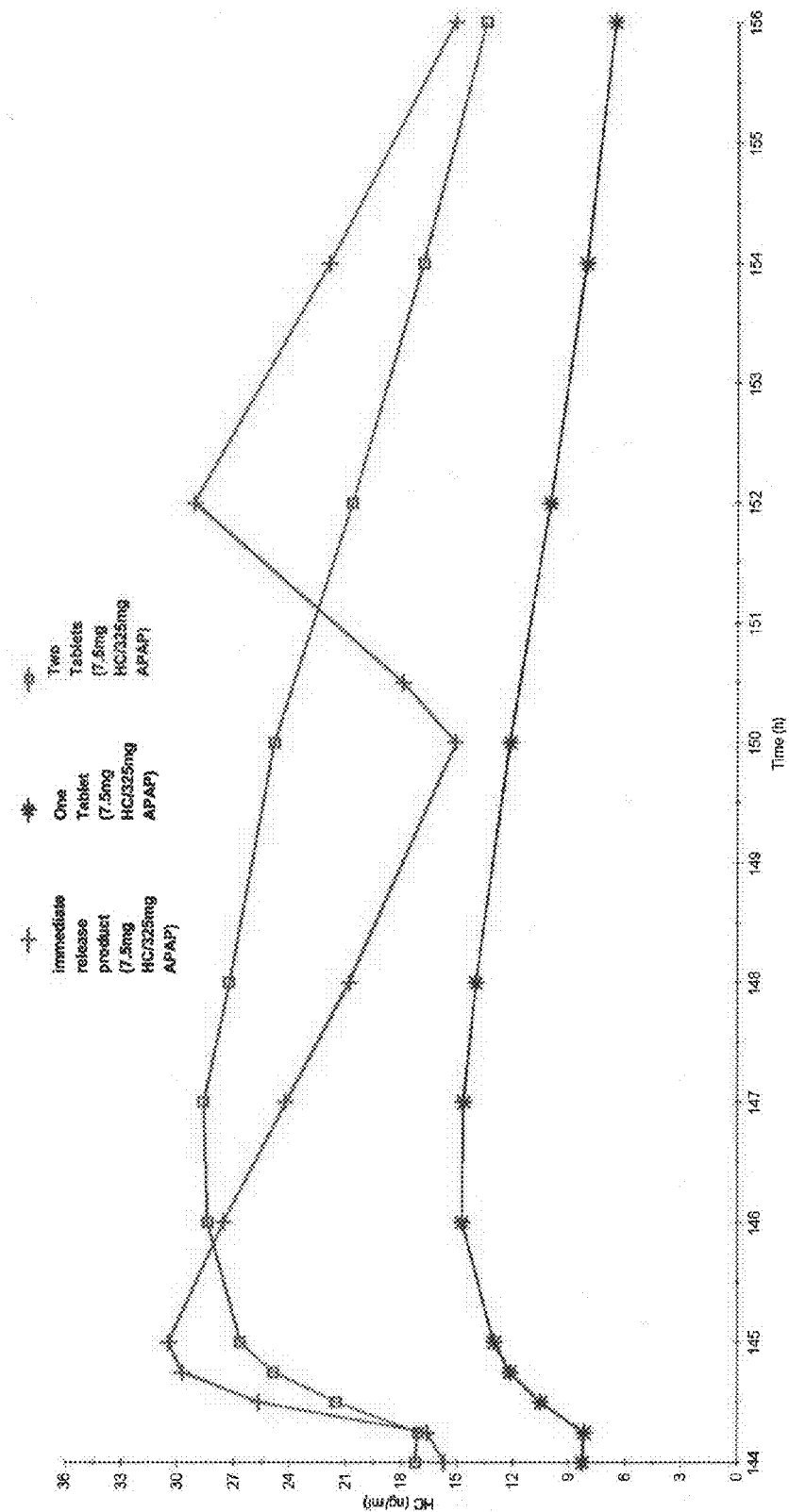

FIG. 11 presents mean plasma concentrations of hydrocodone as a function of time by treatment following oral administration of multiple doses of Treatments A, B, and C of Example 3.

Figure 12:
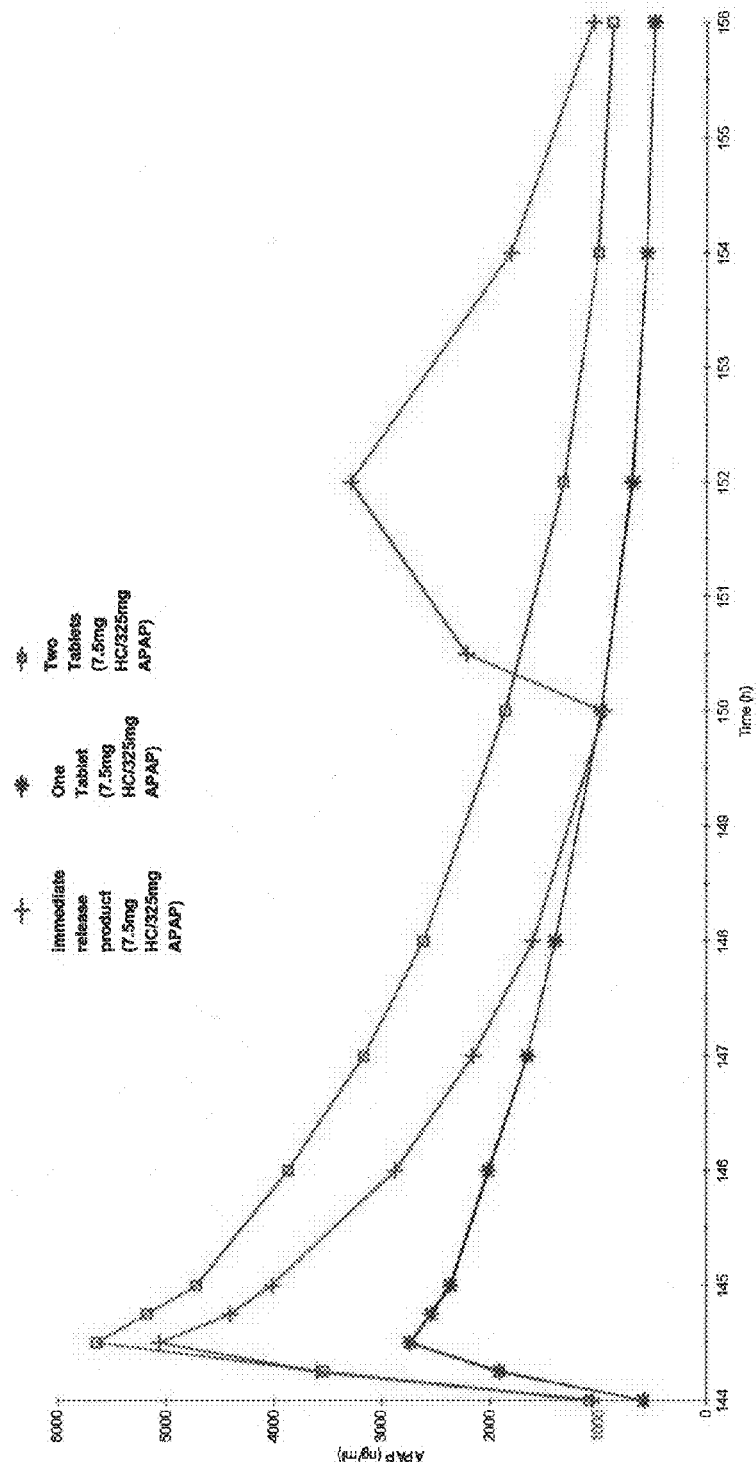

FIG. 12 presents mean plasma concentrations of acetaminophen as a function of time by treatment following oral administration of multiple doses of Treatments A, B, and C of Example 3.

Figure 13:
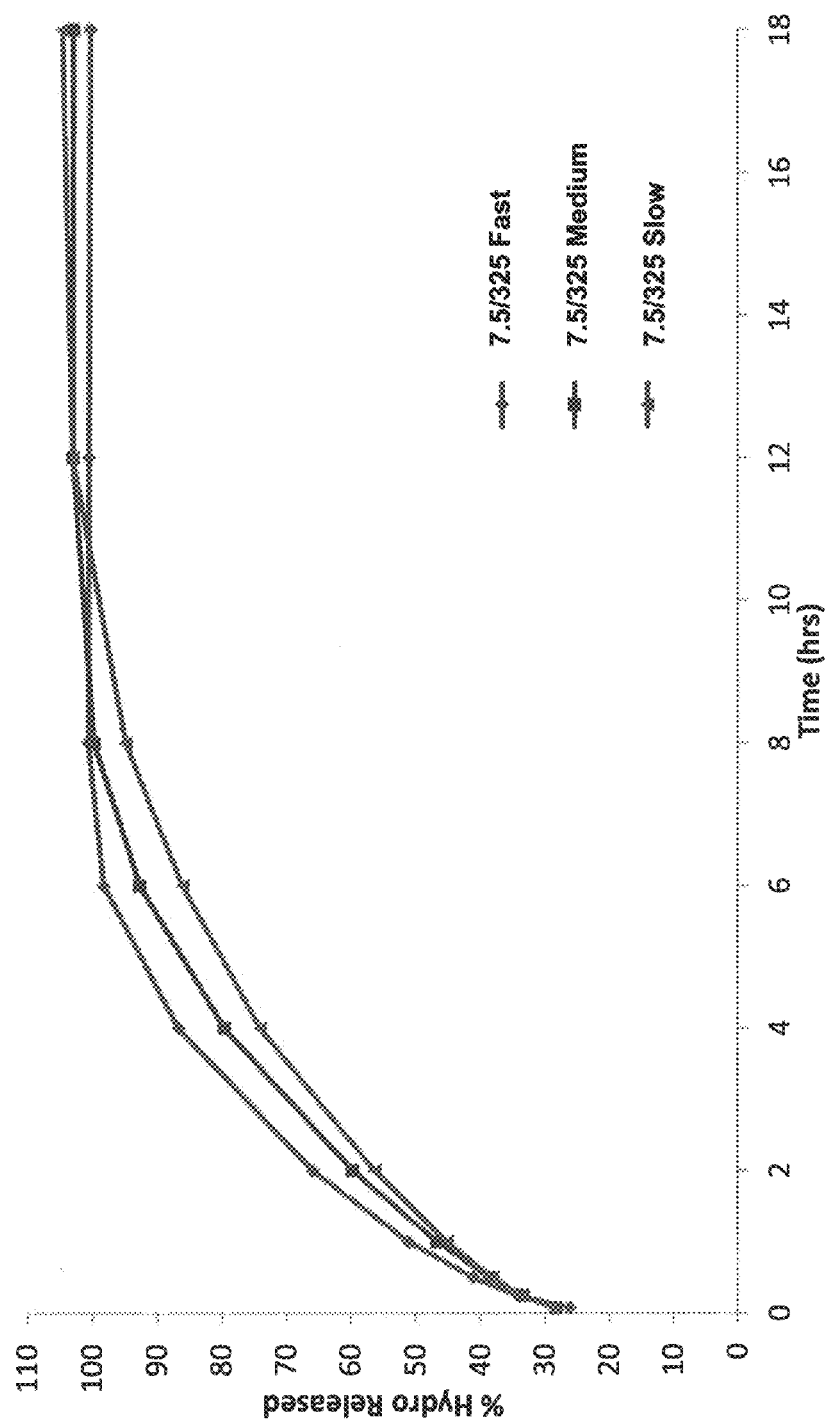

FIG. 13 presents dissolution data for the release of hydrocodone from fast-release, medium-release, and slow-release pharmaceutical compositions containing 7.5 mg hydrocodone and 325 acetaminophen.

Figure 14:
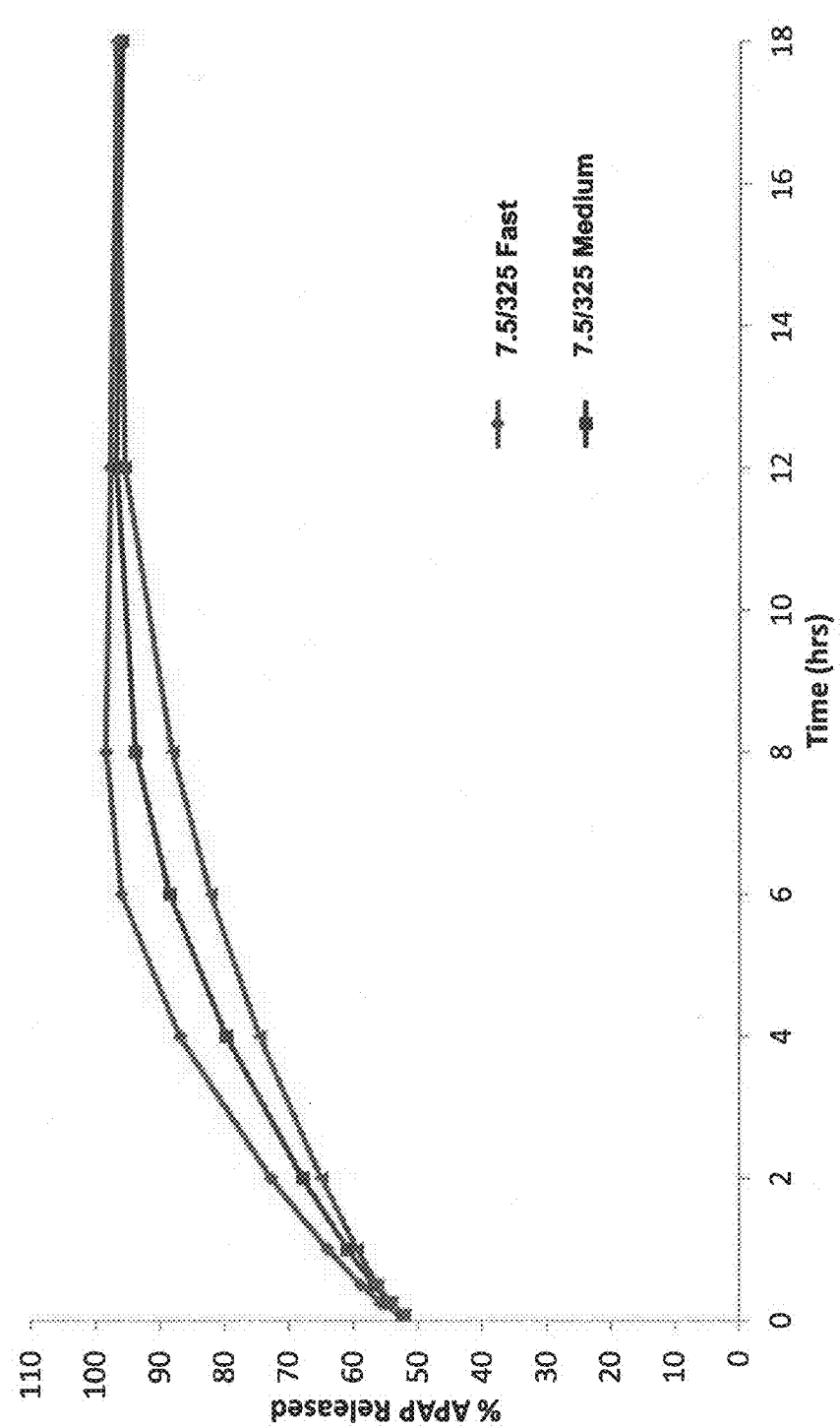

FIG. 14 presents dissolution data for the release of acetaminophen from fast-release, medium-release, and slow-release pharmaceutical compositions containing 7.5 mg hydrocodone and 325 acetaminophen.

Figure 15:
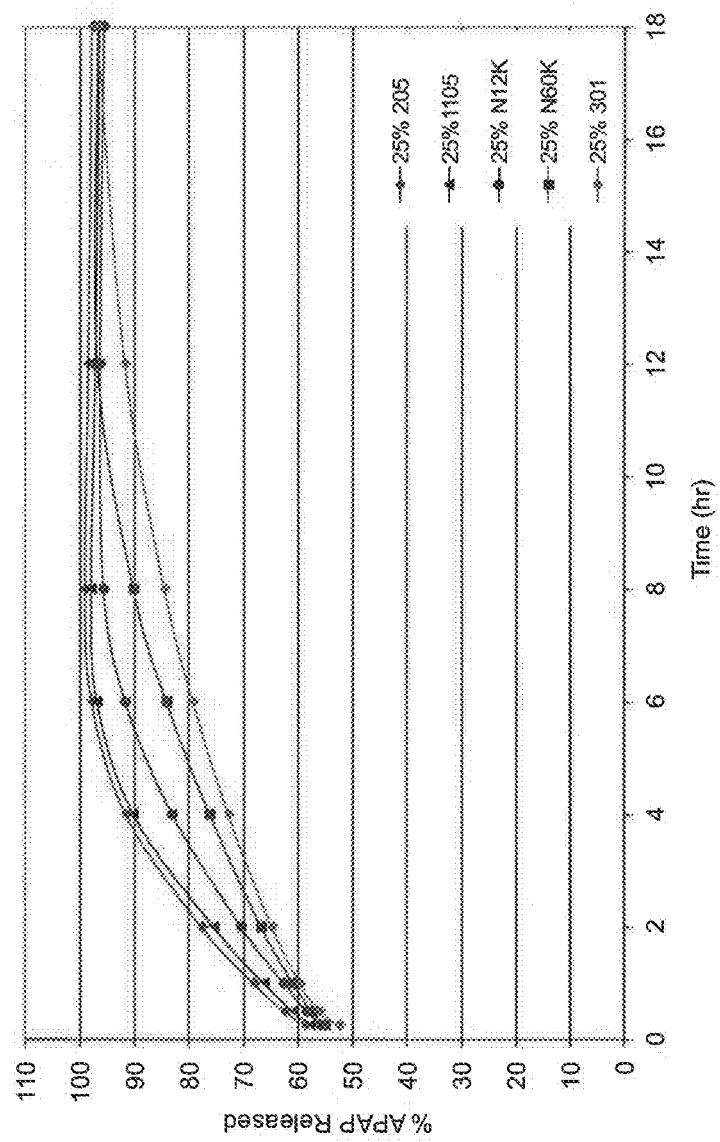

FIG. 15 presents acetaminophen dissolution data for five pharmaceutical formulations described herein. Each formulation tablet contained a total of 15 mg hydrocodone bitartrate HCl and a total of 500 mg acetaminophen. The ER portions of the five pharmaceutical formulations contained 25% by weight POLYOX® 205, 1105, N-12K, N-60K, and 301 respectively.

Figure 16:
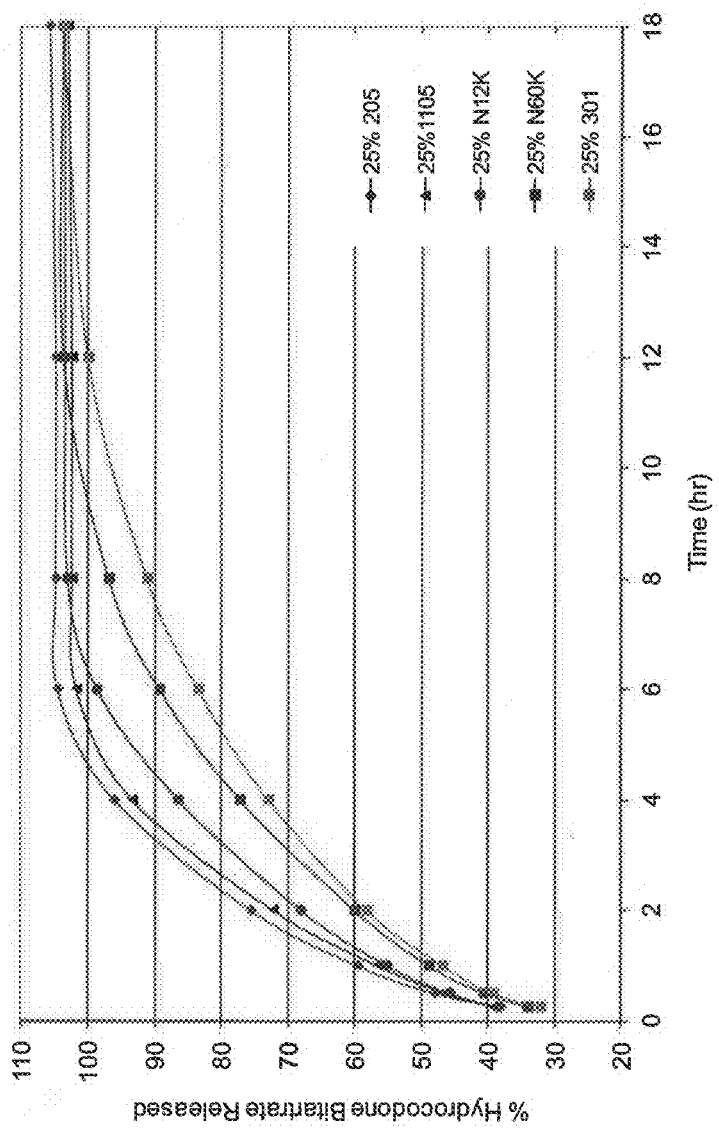

FIG. 16 presents hydrocodone bitartrate dissolution data for the five pharmaceutical formulations described in FIG. 15.

Figure 17:
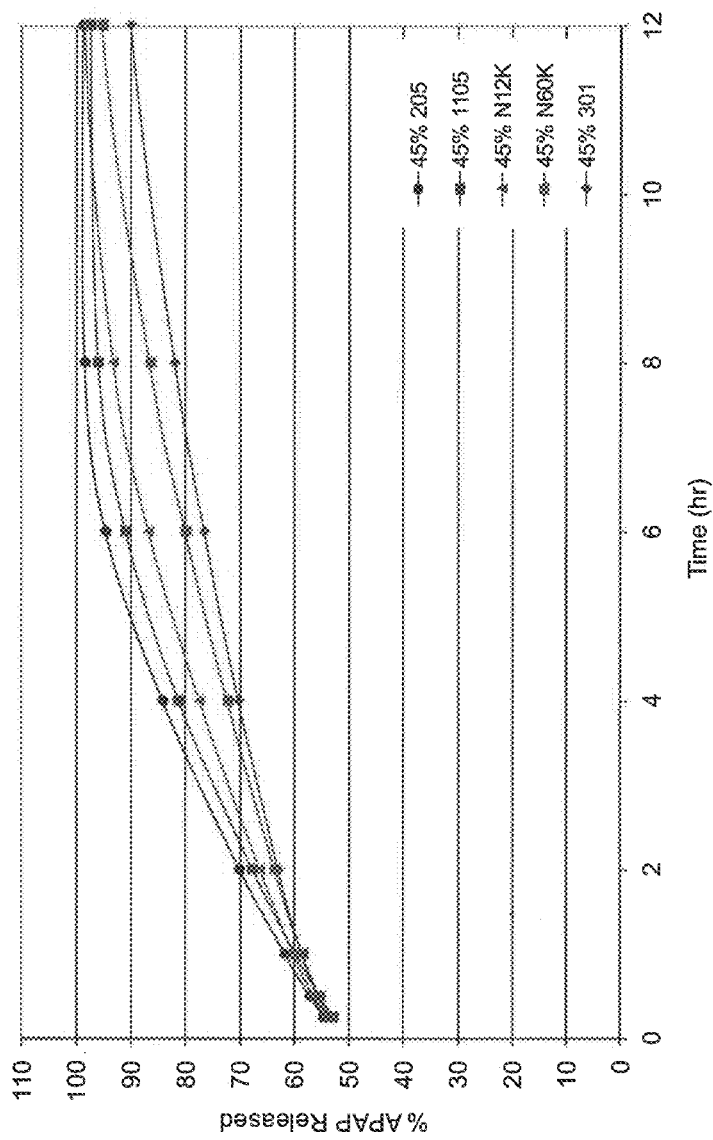

FIG. 17 presents acetaminophen dissolution data for five pharmaceutical formulations described herein. Each formulation tablet contained a total of 15 mg hydrocodone bitartrate and a total of 500 mg acetaminophen. The ER portions of the five pharmaceutical formulations contained 45% by weight POLYOX® 205, 1105, N-12K, N-60K, and 301 respectively.

Figure 18:
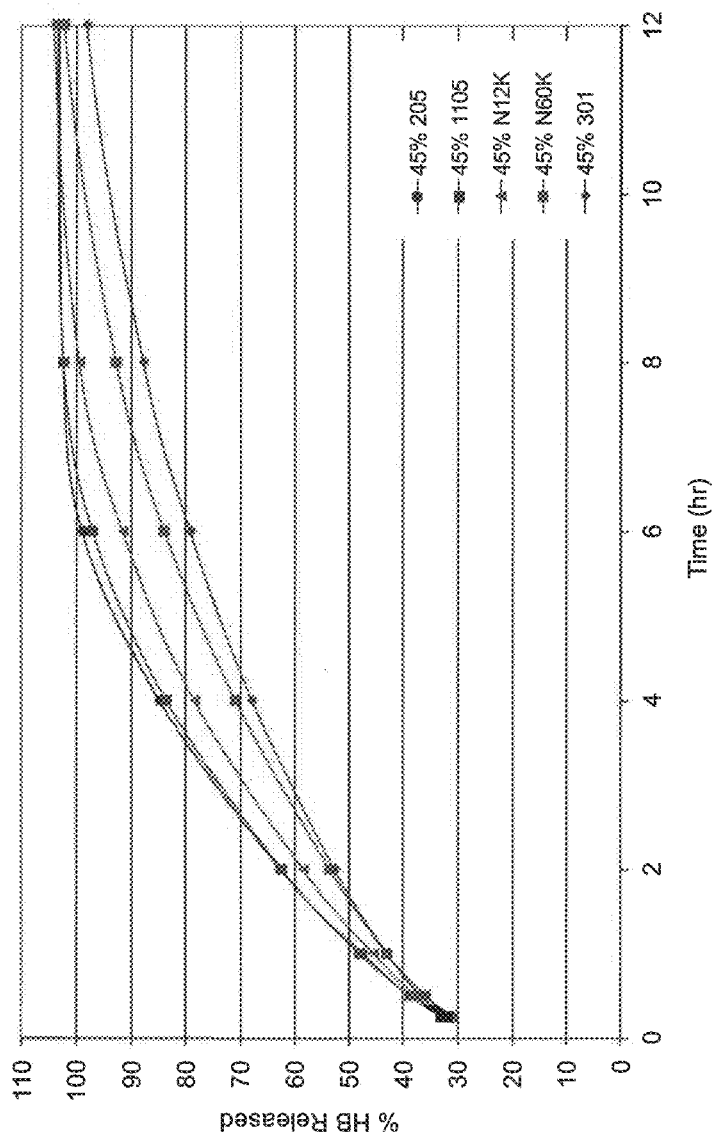

FIG. 18 presents hydrocodone bitartrate dissolution data for the five pharmaceutical formulations described in FIG. 17.

Figure 19:
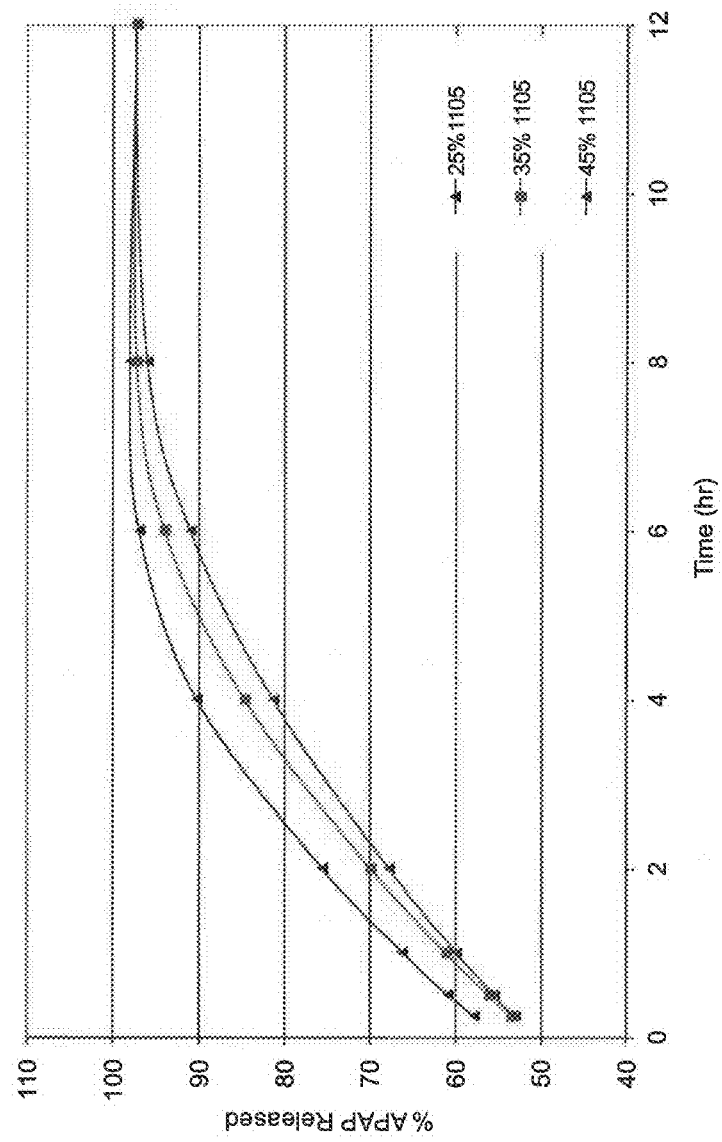

FIG. 19 presents acetaminophen dissolution data for three pharmaceutical formulations described herein. Each formulation tablet contained a total of 15 mg hydrocodone bitartrate and a total of 500 mg acetaminophen. The ER portions of the three pharmaceutical formulations contained 25% by weight, 35% by weight, and 45% by weight POLYOX® 1105, respectively.

Figure 20:
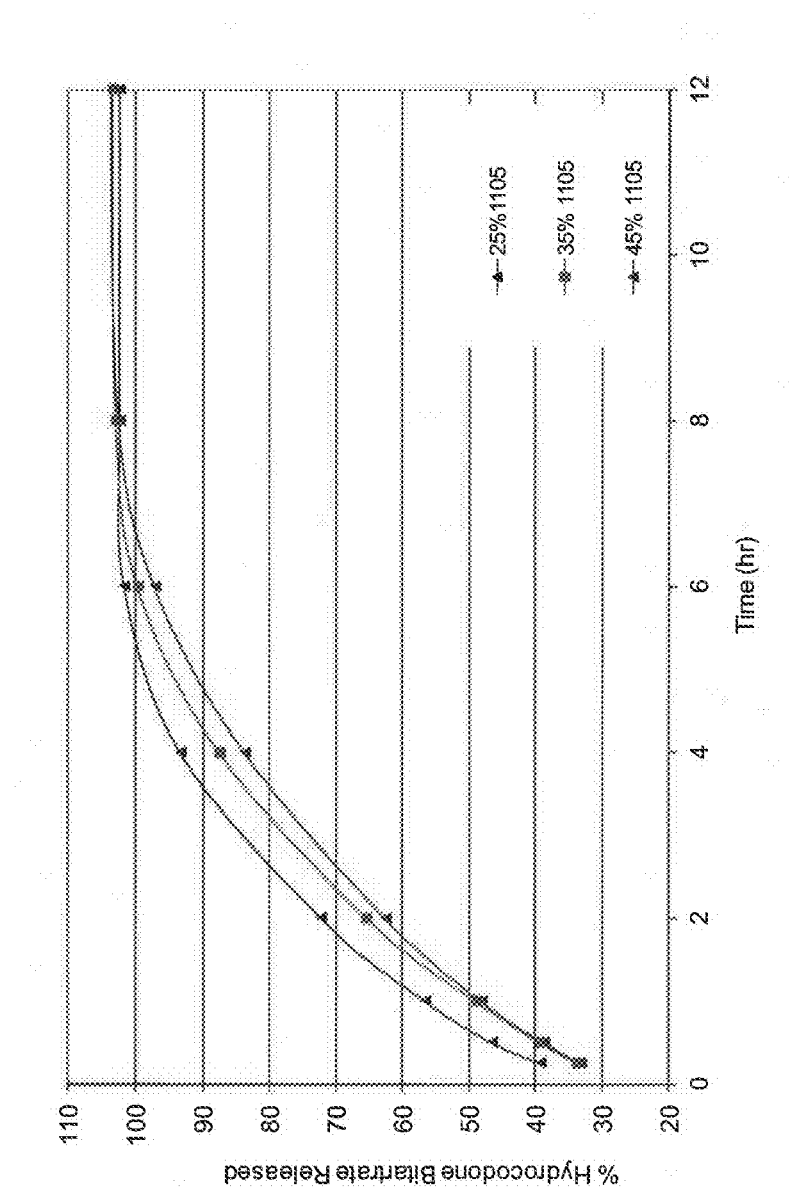

FIG. 20 presents hydrocodone bitartrate dissolution data for the three pharmaceutical formulations described in FIG. 19.

Figure 21:
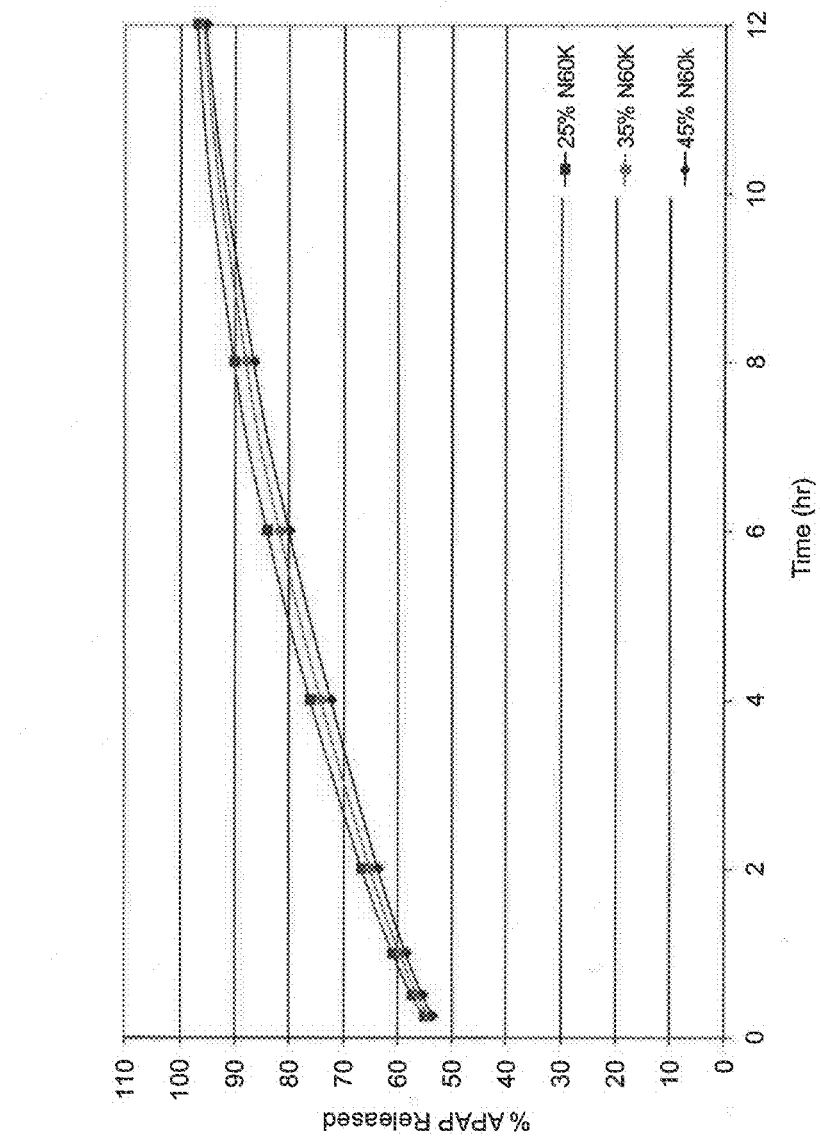

FIG. 21 presents acetaminophen dissolution data for three pharmaceutical formulations described herein. Each formulation tablet contained a total of 15 mg hydrocodone bitartrate and a total of 500 mg acetaminophen. The ER portions of the three pharmaceutical formulations contained 25% by weight, 35% by weight, and 45% by weight POLYOX® N-60K, respectively.

Figure 22:
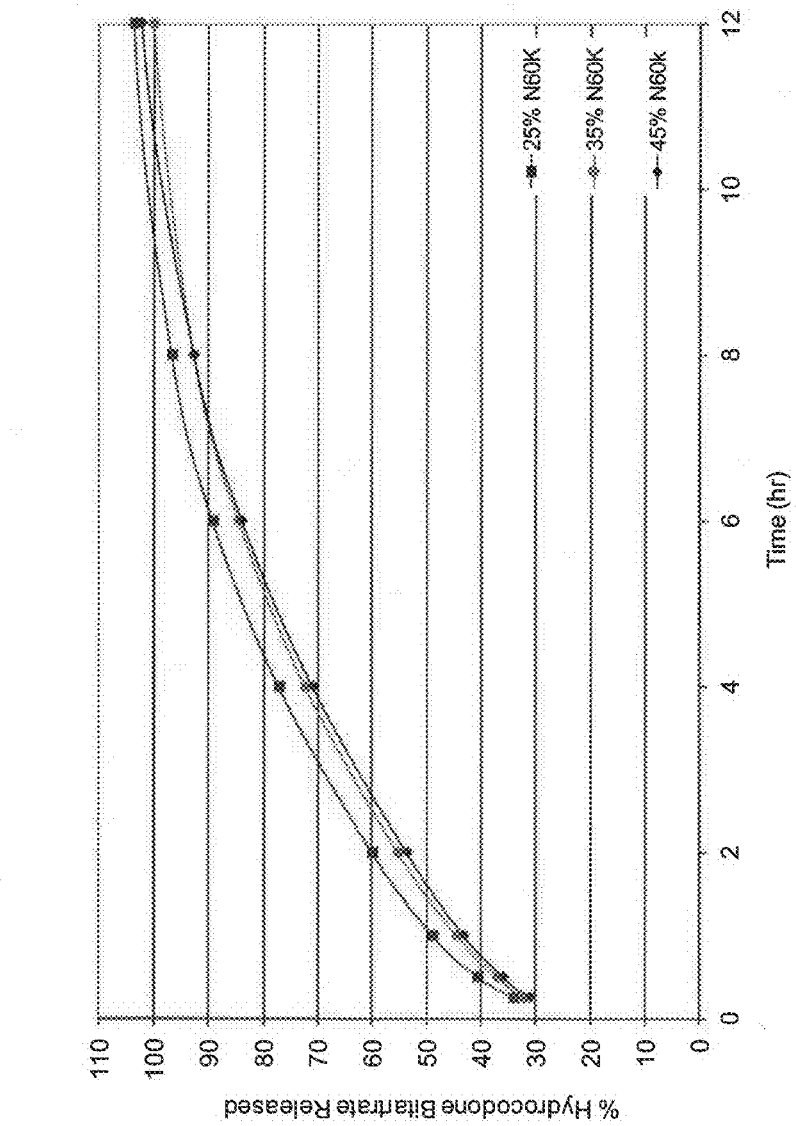

FIG. 22 presents hydrocodone bitartrate dissolution data for the three pharmaceutical formulations described in FIG. 21.

DETAILED DESCRIPTION OF THE INVENTION

Disclosed herein is a combination product of hydrocodone and acetaminophen that has the desirable attributes of both IR and MR products. The extended release pharmaceutical composition disclosed herein comprises at least one extended release portion and, optionally, at least one immediate release portion. The extended release and immediate release portions may comprise hydrocodone, acetaminophen, or combinations thereof. The at least one immediate release portion releases acetaminophen (APAP) and/or hydrocodone instantly in an immediate release fashion that provides rapid onset for the attainment of therapeutically effective plasma concentrations within about the first 5 minutes, 10 minutes, 15 minutes, 20 minutes, 25 minutes, 30 minutes, 35 minutes, 40 minutes, 45 minutes, 50 minutes, 55 minutes, or 60 minutes after administration of the composition. The at least one extended release portion releases acetaminophen and/or hydrocodone in an extended release fashion to maintain plasma concentrations above the minimum effective concentration for about 8-12 hours. In addition, two other important features of this composition are: 1) to allow the plasma concentrations of hydrocodone to fall as rapidly as an immediate release formulation to provide the same rate of termination of drug effects as the immediate release product, and 2) to allow the concentrations of APAP to fall even quicker towards the later part of the dosing interval and bring down the levels of APAP lower than those of the immediate release product. The concentrations of APAP in the last quarter of the dosing interval are comparable to the pre-dose concentrations in a multiple dose setting, allowing for the glutathione synthase enzyme cycle to replenish the body's levels of glutathione to avoid the formation of toxic intermediates with subsequent doses of APAP. Moreover, the concentrations of APAP in the later part of the dosing interval are lower than those present when administered a conventional extended release formulation. This feature has been deliberately introduced to reduce the hepatic injury due to APAP and is termed "APAP time-off".

Abuse potential is a concern with any opioid product. The addition of APAP to the opioid, however, is likely to reduce the amount of abuse by illicit routes of administration, particularly intravenous or intranasal administration. This deterrence is likely due to the bulk (grams) that the APAP provides as well as the relative aqueous insolubility compared to freely soluble opioid salts. Further, APAP is known to be irritating to nasal passages and to make drug abusers sneeze violently when they are trying to snort it. In addition, embodiments disclosed herein may be tamper resistant in that the compositions are difficult to crush for administration intravenously or intranasally; difficult to extract with water or alcohol because the mixture becomes too viscous for injecting or snorting; and resistant to dose dumping in alcohol.

In one embodiment, the pharmaceutical composition disclosed herein, therefore, provides: 1) rapid onset of analgesia within about 15, 30, 45, or 60 minutes after administration of the composition mediated by both hydrocodone and APAP, with APAP providing maximal contribution during the early phase; 2) prolonged analgesia for the entire 12 hours period, mainly contributed by hydrocodone, with minimal fluctuations during this period; 3) relatively low levels of APAP toward end of dosing interval to allow for recovery of the depleted hepatic glutathione system; 4) low abuse quotient; and 5) abuse deterrence.

Headings included herein are simply for ease of reference, and are not intended to limit the disclosure in any way.

I. Definitions

Compounds useful in the compositions and methods include those described herein in any of their pharmaceutically acceptable forms, including isomers such as diastereomers and enantiomers, salts, solvates, and polymorphs, as well as racemic mixtures and pure isomers of the compounds described herein, where applicable.

When introducing elements of the various embodiment(s) of the present disclosure thereof, the articles "a", "an", "the" and "said" are intended to mean that there are one or more of the elements. The terms "comprising", "including" and "having" are intended to be inclusive and mean that there may be additional elements other than the listed elements.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Consequently, recitation of ranges of values herein are merely intended to serve as a shorthand method of referring individually to each separate value falling within the range, unless otherwise indicated herein, and each separate value is incorporated into the specification as if it were individually recited herein.

The term "abuse quotient" for a pharmaceutical composition as used herein is the numerical value obtained via dividing the $C_{max}$ for a drug by the $T_{max}$ for the same drug. Generally speaking, the abuse quotient provides a means for predicting the degree of addictiveness of a given pharmaceutical composition. Pharmaceutical compositions with lower abuse quotients typically are less addictive compared to pharmaceutical compositions with higher abuse quotients.

The term "active agent" or "drug" is used herein to refer to any chemical that elicits a biochemical response when administered to a human or an animal. The drug may act as a substrate or product of a biochemical reaction, or the drug may interact with a cell receptor and elicit a physiological response, or the drug may bind with and block a receptor from eliciting a physiological response.

The term "bioequivalent," as used herein, refers to two compositions, products or methods where the 90% Confidence Intervals (CI) for AUC, partial AUC and $C_{max}$ are between 0.80 to 1.25.

The term "bulk density," as used herein, refers to a property of powders and is defined as the mass of many particles of the material divided by the total volume they occupy. The total volume includes particle volume, inter-particle void volume and internal pore volume.

The term "content uniformity," as used herein refers to the testing of compressed tablets to provide an assessment of how uniformly the micronized or submicron active ingredient is dispersed in the powder mixture. Content uniformity is measured by use of USP Method (General Chapters, Uniformity of Dosage Forms), unless otherwise indicated. A plurality refers to five, ten or more tablet compositions.

The term "friability," as used herein, refers to the ease with which a tablet will break or fracture. The test for friability is a standard test known to one skilled in the art. Friability is measured under standardized conditions by weighing out a certain number of tablets (generally 20 tablets or less), placing them in a rotating Plexiglas drum in which they are lifted during replicate revolutions by a radial lever, and then dropped approximately 8 inches. After replicate revolutions (typically 100 revolutions at 25 rpm), the tablets are reweighed and the percentage of composition abraded or chipped is calculated.

The term "ER" as used herein refers to extended release. The phrases "extended release layer," "ER layer," "ER portion," and "extended release portion" are used interchangeably in this document. Further, as used herein the "extended release layer," "ER layer," "ER portion," and "extended release portion" can be either (i) a discrete part(s) of the pharmaceutical composition, (ii) integrated within the pharmaceutical composition, or (iii) a combination thereof.

The term "IR" as used herein refers to immediate release. The phrases "immediate release layer," "IR layer," "IR portion" and "immediate release portion" are used interchangeable in this document. In addition, as used herein the "immediate release layer," "IR layer," "IR portion" and "immediate release portion" can be either (i) a discrete part(s) of the pharmaceutical composition, (ii) integrated within the pharmaceutical composition, or (iii) a combination thereof.

The term "half life" as used herein refers to the time required for a drug's blood or plasma concentration to decrease by one half. This decrease in drug concentration is a reflection of its excretion or elimination after absorption is complete and distribution has reached an equilibrium or quasi equilibrium state. The half life of a drug in the blood may be determined graphically off of a pharmacokinetic plot of a drug's blood-concentration time plot, typically after intravenous administration to a sample population. The half life can also be determined using mathematical calculations that are well known in the art. Further, as used herein the term "half life" also includes the "apparent half-life" of a drug. The apparent half life may be a composite number that accounts for contributions from other processes besides elimination, such as absorption, reuptake, or enterohepatic recycling.

"Optional" or "optionally" means that the subsequently described element, component or circumstance may or may not occur, so that the description includes instances where the element, component, or circumstance occurs and instances where it does not.

"Partial AUC" means an area under the drug concentration-time curve (AUC) calculated using linear trapezoidal summation for a specified interval of time, for example, $AUC_{(0-1hr)}$, $AUC_{(0-2hr)}$, $AUC_{(0-4hr)}$, $AUC_{(0-6hr)}$, $AUC_{(0-8hr)}$, $AUC_{(0-(Tmax\ of\ IR\ product+2SD))}$, $AUC_{(0-(x)hr)}$, $AUC_{(x-yhr)}$, $AUC_{(Tmax-t)}$, $AUC(0-(t)hr)$, $AUC_{(Tmax\ of\ IR\ product+2SD)-t)}$, or $AUC_{(0-\infty)}$.

A drug "release rate," as used herein, refers to the quantity of drug released from a dosage form or pharmaceutical composition per unit time, e.g., milligrams of drug released per hour (mg/hr). Drug release rates for drug dosage forms are typically measured as an in vitro rate of dissolution, i.e., a quantity of drug released from the dosage form or pharmaceutical composition per unit time measured under appropriate conditions and in a suitable fluid. The specific results of dissolution tests claimed herein are performed on dosage forms or pharmaceutical compositions immersed in 900 mL of 0.1 N HCl using a USP Type II apparatus at a paddle speed of either about 100 rpm or about 150 rpm and a constant temperature of about 37° C. Suitable aliquots of the release rate solutions are tested to determine the amount of drug released from the dosage form or pharmaceutical composition. For example, the drug can be assayed or injected into a chromatographic system to quantify the amounts of drug released during the testing intervals.

The terms "subject" or "patient" are used interchangeably herein and refer to a vertebrate, preferably a mammal. Mammals include, but are not limited to, humans.

The term "tap density" or "tapped density," as used herein, refers to a measure of the density of a powder. The tapped density of a pharmaceutical powder is determined using a tapped density tester, which is set to tap the powder at a fixed impact force and frequency. Tapped density by the USP method is determined by a linear progression of the number of taps.

II. Pharmaceutical Compositions Comprising Extended and Immediate Release Portions Comprising Hydrocodone and Acetaminophen The present disclosure provides pharmaceutical compositions comprising hydrocodone and its pharmaceutical salts and acetaminophen. The pharmaceutical composition comprises at least one extended release portion comprising hydrocodone, acetaminophen or a combination thereof, and an extended release component. The pharmaceutical composition may also comprise at least one immediate release portion comprising hydrocodone, acetaminophen, or a combination thereof. The compositions disclosed herein are formulated to deliver therapeutic concentrations of hydrocodone and acetaminophen within about the first hour after oral administration and to maintain therapeutic concentrations of hydrocodone and acetaminophen for an extended period of time (e.g., 10-12 hours).

The total amount of hydrocodone present in the pharmaceutical composition can and will vary. In some embodiments, the total amount of hydrocodone present in the pharmaceutical composition may range from about 2 mg to about 160 mg, about 5 mg to about 75 mg, about 5 mg to about 40 mg, or about 10 mg to about 30 mg. In another embodiment, the total amount of hydrocodone in the pharmaceutical composition may range from about 5 mg to about 30 mg. In various embodiments, the total amount of hydrocodone present in the pharmaceutical composition may be about 5 mg, 5.5 mg, 6.0 mg, 6.5 mg, 7.0 mg, 7.5 mg, 8.0 mg, 8.5 mg, 9.0 mg, 9.5 mg, 10 mg, 10.5 mg, 11 mg, 11.5 mg, 12 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 22.5 mg, 25 mg, 27.5 mg, 30 mg, 32.5 mg, 35 mg, 37.5 mg, 40 mg, 45 mg, 50 mg, 60 mg, 70 mg, 80 mg, 100 mg, 110 mg, 120 mg, 130 mg, 140 mg, 150 mg, or 160 mg. In one embodiment, the total amount of hydrocodone in the pharmaceutical composition may be about 30 mg. In another embodiment, the total amount of hydrocodone in the pharmaceutical composition may be about 15 mg. In still another embodiment, the total amount of hydrocodone in the pharmaceutical composition may be about 7.5 mg.

The total amount of acetaminophen present in the pharmaceutical composition also may vary. In one embodiment, the total amount of acetaminophen present in the pharmaceutical composition may range from about 80 mg to about 1600 mg. In another embodiment, the total amount of acetaminophen present in the pharmaceutical composition may be about 250 mg to about 1300 mg. In a further embodiment, the total amount of acetaminophen present in the pharmaceutical composition may be about 300 mg to about 600 mg. In yet another embodiment, the total amount of acetaminophen present in the pharmaceutical composition may be about 325 mg to about 650 mg. In another embodiment, the total amount of acetaminophen present in the pharmaceutical composition may be about 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 600 mg, 650 mg, 700 mg, 750 mg, 1000 mg, or 1300 mg. In one embodiment, the total amount of acetaminophen in the pharmaceutical composition may be about 650 mg. In another embodiment, the total amount of acetaminophen in the pharmaceutical composition may be about 500 mg. In yet another embodiment, the total amount of acetaminophen in the pharmaceutical composition may be about 325 mg.

(a) Immediate Release Portion

The pharmaceutical composition disclosed herein may comprise at least one immediate release portion. In one embodiment, the at least one immediate release portion may comprise hydrocodone. In another embodiment, the at least one immediate release portion may comprise acetaminophen. In a further embodiment, the at least one immediate release portion may comprise hydrocodone and acetaminophen.

The at least one immediate release portion of the pharmaceutical composition is designed to release more than 80%, more than 90%, or essentially all of the hydrocodone and/or acetaminophen in the at least one immediate release portion(s) within about one hour. In one embodiment, more than 80%, more than 90%, or essentially all of the hydrocodone and/or acetaminophen in the at least one immediate release portion(s) may be released in less than about 45 min. In another embodiment, more than 80%, more than 90%, or essentially all of the hydrocodone and/or acetaminophen in the at least one immediate release portion(s) may be released in less that about 30 min. In a further embodiment, more than 80%, more than 90%, or essentially all of the hydrocodone and/or acetaminophen in the at least one immediate release portion(s) may be released in less than about 20 min. In yet another embodiment, more than 80%, more than 90%, or essentially all of the hydrocodone and/or acetaminophen in the at least one immediate release portion(s) may be released in less that about 15 min. In an alternate embodiment, more than 80%, more than 90%, or essentially all of the hydrocodone and/or acetaminophen in the at least one immediate release portion(s) may be released in less that about 10 min. In yet another embodiment, more than 80%, more than 90%, or essentially all of the hydrocodone and/or acetaminophen in the at least one immediate release portion may be released in less that about 5 min.

(i) Hydrocodone

The at least one immediate release portion of the pharmaceutical composition may comprise hydrocodone. The amount of hydrocodone in the at least one immediate release portion of the pharmaceutical composition can and will vary. In one embodiment, the amount of hydrocodone in the at least one immediate release portion may range from about 1 mg to about 40 mg. In a further embodiment, the amount of hydrocodone in the at least one immediate release portion of the pharmaceutical composition may range from about 1 mg to about 7.5 mg. In another embodiment, the amount of hydrocodone in the at least one immediate release portion may range from about 7.5 mg to about 15 mg. In yet another embodiment, the amount of hydrocodone in the at least one immediate release portion may range from about 15 mg to about 40 mg. In various embodiments, the amount of hydrocodone in the at least one immediate release portion may be about 1.25 mg, 1.3 mg, 1.325 mg, 1.35 mg, 1.375 mg, 1.4 mg, 1.425 mg, 1.45 mg, 1.475 mg, 1.5 mg, 1.525 mg, 1.55 mg, 1.575 mg, 1.6 mg, 1.625 mg, 1.65 mg, 1.675 mg, 1.7 mg, 1.725 mg, 1.75 mg, 1.775 mg, 1.8 mg, 1.825 mg, 1.85 mg, 1.875 mg, 1.9 mg, 1.925 mg, 1.95 mg, 1.975 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5.0 mg, 5.25 mg, 5.5 mg, 5.75 mg, 6.0 mg, 6.25 mg, 6.5 mg, 6.75 mg, 7.0 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10.0 mg, 11.0 mg, 12.0 mg, 13.0 mg, 14.0 mg, 15.0 mg, 20.0 mg, or 40.0 mg. In one embodiment, the amount of hydrocodone in the at least one immediate release portion may range from about 7.0 mg and about 8.0 mg, for example, about 7.5 mg. In another embodiment, the amount of hydrocodone in the at least one immediate release portion may be between about 3.0 mg and about 4.0 mg, for example, about 3.75 mg. In still another embodiment, the amount of hydrocodone in the at least one immediate release portion may be between about 1.0 mg and about 2.0 mg, for example, about 1.875 mg.

The amount of hydrocodone present in the at least one immediate release portion(s) may be expressed as a percentage (w/w) of the total amount of hydrocodone in the pharmaceutical composition. In one embodiment, the at least one immediate release portion may comprise from about 20% to about 30% (w/w) of the total amount of hydrocodone present in the pharmaceutical composition. In certain embodiments, the percentage of hydrocodone present in the at least one immediate release portion of the pharmaceutical composition may be about 20%, 21%, 22%, 23%, 24%, 25%, 26%, 27%, 28%, 29%, or 30% (w/w) of the total amount of hydrocodone. In another embodiment, the percentage of hydrocodone present in the at least one immediate release portion of the pharmaceutical composition may be about 25% (w/w) of the total amount of hydrocodone present in the pharmaceutical composition.

The amount of hydrocodone in the at least one immediate release portion also may be expressed as a percentage (w/w) of the total weight of the immediate release portion(s) of the pharmaceutical composition. In one embodiment, the amount of hydrocodone in an immediate release portion may range from about 0.2 (w/w) to about 15.0% (w/w) of the total weight of such immediate release portion of the pharmaceutical composition. In another embodiment, the amount of hydrocodone in an immediate release portion may range from about 0.5% (w/w) to about 2% (w/w) of the total weight of such immediate release portion. In various embodiments, an immediate release portion may comprise an amount of hydrocodone that is approximately 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, 10%, 11%, 12%, 13%, 14%, 15%, 16%, 17%, 18%, 19%, or 20% (w/w) of the total weight of such immediate release portion of the pharmaceutical composition. In yet another embodiment, the amount of hydrocodone in an immediate release portion may be about 0.5% (w/w) to about 1.0% (w/w) of the total weight of such immediate release portion of the pharmaceutical composition.

In some embodiments, the hydrocodone of the at least one immediate release portion(s) of the pharmaceutical composition may be in the form of particles comprising hydrocodone and at least one excipient. The at least one immediate release portion, therefore, may comprise particles of hydrocodone that are admixed with the acetaminophen and optional excipient(s). The hydrocodone particles may be coated or uncoated. The average size or average diameter of the particles may vary. In general, the average diameter of the particles may range from about 50 microns to about 2000 microns, from about 100 microns to about 1000 microns, or from about 150 microns to about 200 microns. In one embodiment, the maximum diameter of about 50% of the particles (d50) may be about 40 microns, 50 microns, 100 microns, 150 microns, 200 microns, 250 microns, 300 microns, 400 microns, or 500 microns. In another embodiment, the maximum diameter of about 90% of the particles (d90) may be about 100 microns, 150 microns, 200 microns, 250 microns, 300 microns, 400 microns, or 500 microns.

(ii) Acetaminophen

The at least one immediate release portion of the pharmaceutical composition may comprise acetaminophen. The amount of acetaminophen in the at least one immediate release portion(s) can and will vary. In one embodiment, the amount of acetaminophen in the at least one immediate release portion of the pharmaceutical composition may range from about 40 mg to about 800 mg. In still another embodiment, the at least one immediate release portion of the pharmaceutical composition may comprise from about 100 mg to about 600 mg of acetaminophen. In another embodiment, the at least one immediate release portion may comprise from about 125 mg to about 400 mg of acetaminophen. In a further embodiment, the amount of acetaminophen in the at least one immediate release portion may range from about 160 mg to about 325 mg. In yet another embodiment, the amount of acetaminophen in the at least one immediate release portion may be about 120 mg, 125 mg, 130 mg, 135 mg, 140 mg, 145 mg, 150 mg, 155 mg, 160 mg, 162.5 mg, 165 mg, 170 mg, 175 mg, 180 mg, 185 mg, 190 mg, 195 mg, 200 mg, 210 mg, 220 mg, 230 mg, 240 mg, 250 mg, 260 mg, 270 mg, 280 mg, 290 mg, 300 mg, 310 mg, 320 mg, 325 mg, 330 mg, 340 mg, 350 mg, 360 mg, 370 mg, 380 mg, 390 mg, 400 mg, 500 mg, 520 mg, 650 mg, or 780 mg. In one embodiment, the at least one immediate release portion may comprise about 325 mg of acetaminophen. In another embodiment, the amount of acetaminophen in the at least one immediate release portion may be about 250 mg. In yet another embodiment, the amount of acetaminophen in the at least one immediate release portion may be about 162.5 mg. In still another embodiment, the amount of acetaminophen in the at least one immediate release portion may be about 125 mg.

The at least one immediate release portion(s) of the pharmaceutical composition may comprise from about 40% to about 60% (w/w) of the total amount of acetaminophen present in the pharmaceutical composition. The amount of acetaminophen in the at least one immediate release portion may be about 40%, 41%, 42%, 43%, 44%, 45%, 46%, 47%, 48%, 49%, 50%, 51%, 52%, 53%, 54%, 55%, 56%, 57%, 58%, 59%, or 60% (w/w) of the total amount of acetaminophen present in the pharmaceutical composition. In one embodiment, the percentage of acetaminophen present in the at least one immediate release portion may be about 50% (w/w) of the total amount of acetaminophen present in the pharmaceutical composition.

The amount of acetaminophen in an immediate release portion(s) of the pharmaceutical composition may range from about 20% (w/w) to about 95% (w/w) of the total weight of such immediate release portion of the composition. In various embodiments, an immediate release portion may comprise an amount of acetaminophen that is approximately about 20%, 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95% (w/w) of the total weight of such immediate release portion. In one embodiment, the amount of acetaminophen in an immediate release portion may range from about 70% to about 80% (w/w) of the total weight of such immediate release portion of the pharmaceutical composition.

(iii) Excipients

The at least one immediate release portion(s) of the pharmaceutical composition may further comprise at least one excipient. Suitable excipients include binders, fillers, disintegrants, lubricants, antioxidants, chelating agents, and color agents.

In one embodiment, the at least one immediate release portion(s) of the pharmaceutical composition may comprise at least one binder. Suitable binders include, without limit, starches (including corn starch and pregelatinized starch), gelatin, sugars (including sucrose, glucose, dextrose and lactose), polyethylene glycol, polyols, polyvinylalcohols, C12-C18 fatty acid alcohols, waxes, gums (e.g., guar gum, arabic gum, acacia gum, xantham gum, etc.), gelatin, pectin, sodium alginate, polyvinylpyrrolidone, cellulosic polymers (including hydroxypropyl cellulose, hydroxypropyl methylcellulose, hydroxylcellulose, methylcellulose, microcrystalline cellulose, ethylcellulose, hydroxyethyl cellulose, and the like), polyacrylamides, and polyvinyloxoazolidone. In one embodiment, the amount of binder or binders in an immediate release portion of the pharmaceutical composition may range from about 5% to about 10% (w/w) of the total weight of such immediate release portion. In various embodiments, an immediate release portion of the pharmaceutical composition may comprise at least one binder that is present in an amount that is about 5.0%, 5.25%, 5.5%, 5.75%, 6.0%, 6.25%, 6.5%, 6.75%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, or 9.0% (w/w) of such immediate release portion of the composition.

In another embodiment, the at least one immediate release portion(s) of the pharmaceutical composition may comprise at least one filler. Suitable fillers include but are not limited to microcrystalline cellulose (MCC), dibasic calcium phosphate, tribasic calcium phosphate, magnesium carbonate, magnesium oxide, calcium silicate, magnesium aluminum silicate, silicon dioxide, titanium dioxide, alumina, talc, kaolin, polyvinylpyrrolidone, dibasic calcium sulfate, tribasic calcium sulfate, starch, calcium carbonate, magnesium carbonate, carbohydrates, modified starches, lactose, sucrose, dextrose, mannitol, sorbitol, and inorganic compounds. In one embodiment, the amount of filler or fillers in an immediate release portion may range from about 1.0% to about 10.0% (w/w) of the total weight of such immediate release portion. In various embodiments, an immediate release portion of the pharmaceutical composition may comprise at least one filler that is present in an amount that is about 1.0%, 1.5%, 2.0%, 2.5%, 3.0%, 3.5%, 4.0%, 4.5%, 5.0%, 5.5%, 6.0%, 6.2%, 6.4%, 6.5%. 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, or 10.0%, (w/w) of such immediate release portion of the pharmaceutical composition.

In still another embodiment, the at least one immediate release portion(s) of the pharmaceutical composition may further comprise a disintegrant. The disintegrant may be selected from the group consisting of croscarmellose sodium, crospovidone, alginic acid, carboxymethylcellulose calcium, carboxymethylcellulose sodium, low substituted hydroxypropylcellulose, microcrystalline cellulose, and sodium starch glycolate. In one embodiment, the amount of disintegrant in an immediate release portion may range from about 2.0% to about 15.0% (w/w) of the total weight of such immediate release portion. In some embodiments, the amount of disintegrant in an immediate release portion may be about 4.0%, 4.2%, 4.4%, 4.6%, 4.8%, 5.0%, 5.2%, 5.4%, 5.6%. 5.8%, 6.0%, 6.2%, 6.4%. 6.6%, 6.8%, or 7.0% (w/w) of such immediate release portion of the pharmaceutical composition.

In a further embodiment, the at least one immediate release portion(s) of the pharmaceutical composition may further comprise a lubricant. Useful lubricants include magnesium stearate, calcium stearate, stearic acid, and hydrogenated vegetable oil (preferably comprised of hydrogenated and refined triglycerides of stearic and palmitic acids). The lubricant may be present in an amount ranging from about 0.1% to about 3.0% (w/w) of the total weight of an immediate release portion. In certain embodiments, the amount of lubricant in at least one immediate release portion may be about 0.25%, 0.5%, 0.75%, 1.0%, 1.5%, 1.55%, 1.6%, 1.65%, 1.7%, 1.75%, 1.80%, 1.85%, 1.90%, or 2.0% (w/w) of the total weight of such immediate release portion.

In yet another embodiment, the at least one immediate release portion(s) of the pharmaceutical composition may comprise at least one antioxidant. Suitable antioxidants include, without limitation, ascorbic acid, citric acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiarybutylphenol, alphatocopherol, and propylgallate. The amount of antioxidant present in an immediate release portion of the pharmaceutical composition may range from about 0.01% to about 4.0% (w/w), or from about 0.02% to about 0.10% (w/w) of the total weight of such immediate release portion. In various embodiments, the amount of antioxidant present in an immediate release portion of the pharmaceutical composition may be about 0.01%, 0.02%, 0.03%, 0.04%, 0.05%, 0.06%, 0.07%, 0.08%, 0.09%, 0.10%, 0.12%, 0.14%, 0.16%, 0.18%. 0.20%, 0.25%, 0.50%, 0.75%, 1.00%, 1.50%, or 2.00% (w/w) of the total weight of such immediate release portion.

In still another embodiment, the at least one immediate release portion(s) of the pharmaceutical composition may comprise at least one chelating agent. Suitable chelating agents include ethylenediamine tetracetic acid (EDTA) and its salts, N-(hydroxy-ethyl)ethylenediaminetriacetic acid, nitrilotriacetic acid (NIA), ethylene-bis(oxyethylene-nitrilo) tetraacetic acid, 1,4,7,10-tetraazacyclodo-decane-N,N',N'', N'''-tetraacetic acid, 1,4,7,10-tetraaza-cyclododecane-N,N', N''-triacetic acid, 1,4,7-tris(carboxymethyl)-10-(2'-hydroxypropyl)-1,4,7,10-tetraazocyclodecane, 1,4,7-triazacyclonane-N,N',N''-triacetic acid, 1,4,8,11-tetraazacyclotetra-decane-N,N',N'',N'''-tetraacetic acid; diethylenetriamine-pentaacetic acid (DTPA), ethylenedicysteine, bis(aminoethanethiol)carboxylic acid, triethylenetetraamine-hexaacetic acid, and 1,2-diaminocyclohexane-N,N, N',N'-tetraacetic acid. In one embodiment, the chelating agent may be the sodium salt of EDTA. The amount of chelating agent present in an immediate release portion of the pharmaceutical composition may range from about 0.001% to about 0.20% (w/w) of such immediate release portion. In some embodiments, the amount of chelating agent present in an immediate release portion of the pharmaceutical composition may be about 0.001%, 0.002%, 0.003%, 0.004%, 0.005%, 0.01%, 0.02%, 0.03%, 0.04%, 0.05%, 0.06%, 0.07%, 0.08%, 0.09%, 0.10%, 0.11%, 0.12%, 0.13%, 0.14%, or 0.15% (w/w) of the total weight of such immediate release portion.

In an alternate embodiment, the at least one immediate release portion of the pharmaceutical composition may comprise a color agent. Suitable color additives include, but are not limited to, food, drug and cosmetic colors (FD&C), drug and cosmetic colors (D&C), and external drug and cosmetic colors (Ext. D&C). In various embodiments, the amount of color agent present in an immediate release portion may range from about 2.0% to about 5.0% (w/w) of the total weight of such immediate release portion of the composition. In other embodiments, the amount of color agent present in an immediate release portion may be about 1.0%, 1.5%, 2.0%, 2.5%, 3.0%, 3.5%, 4.0%, 4.5%, or 5.0% (w/w) of the total weight of such immediate release portion.

(b) Extended Release Portion

The pharmaceutical composition disclosed herein comprises at least one extended release portion. The at least one extended release portion may comprise hydrocodone, acetaminophen, or a combination thereof. The extended release portion(s) further comprise(s) an extended release component. The extended release component may comprise at least one extended release polymer.

The at least one extended release portion of the pharmaceutical composition is designed to release the active agents over an extended period of time. In general, the extended release portion(s) provides release of hydrocodone and/or acetaminophen for a period of time ranging from at least about 3 hours (hrs) to at least about 12 hrs. In one embodiment, the extended release portion(s) may release hydrocodone and/or acetaminophen over a period of at least about 5 hrs, or over a period at least about 6 hrs. In another embodiment, hydrocodone and/or acetaminophen may be released from the extended release portion(s) over a period of at least about 7 hrs, or over a period of at least about 8 hrs. In still another embodiment, the extended release portion(s) may release hydrocodone and/or acetaminophen over a period of at least about 9 hrs, or over a period of at least about 10 hrs. In a further embodiment, hydrocodone and/or acetaminophen may be released from the extended release portion(s) over a period of at least about 11 hrs, or over a period of at least about 12 hrs.

(i) Hydrocodone

The amount of hydrocodone present in the at least one extended release portion(s) can and will vary. In one embodiment, the amount of hydrocodone in the at least one extended release portion may range from about 1 mg to about 120 mg. In a further embodiment, the at least one extended release portion of the pharmaceutical composition may comprise about 1 mg to about 22.5 mg of hydrocodone. In another embodiment, the amount of hydrocodone in the at least one extended release portion may be about 10 mg to about 30 mg. In yet another embodiment, the amount of hydrocodone in the at least one extended release portion may be about 30 mg to about 60 mg. In another embodiment, the at least one extended release portion comprises about 5 mg to about 7 mg of hydrocodone. In a further embodiment, the amount of hydrocodone may be about 5.625 mg to about 11.25 mg. In an additional embodiment, the amount of hydrocodone may be about 10 mg to about 12.5 mg. In a further embodiment, the amount of hydrocodone may be about 12 mg to about 18 mg. In another embodiment, the amount of hydrocodone in the at least one extended release portion may be about 20 mg to about 25 mg. In yet another embodiment, the amount of hydrocodone may be about 1.0 mg, 1.5 mg, 2.0 mg, 2.5 mg, 3.0 mg, 3.5 mg, 4.0 mg, 4.5 mg, 5.0 mg, 5.5 mg, 5.625 mg, 6.0 mg, 6.5 mg, 7.0 mg, 7.5 mg, 8.0 mg, 8.5 mg, 9.0 mg, 9.5 mg, 10.0 mg, 10.5 mg, 11.0 mg, 11.25 mg, 11.5 mg, 12.0 mg, 12.5 mg, 13.0 mg, 13.5 mg, 14.0 mg, 14.5 mg, 15.0 mg, 15.5 mg, 16.0 mg, 16.5 mg, 17.0 mg, 17.5 mg, 18.0 mg, 18.5 mg, 19.0 mg, 19.5 mg, 20.0 mg, 22.5 mg, or 25 mg. In one embodiment, the amount of hydrocodone in the at least one extended release portion may be from about 22 mg to about 23 mg, for example, about 22.5 mg. In another embodiment, the amount of hydrocodone in the at least one extended release portion may be about 10 mg to about 12 mg, for example, about 11.25 mg. In still another embodiment, the amount of hydrocodone in the at least one extended release portion may be from about 5 mg to about 6 mg, for example, about 5.625 mg.

The amount of hydrocodone present in the at least one extended release portion(s) may be expressed as a percentage of the total amount of hydrocodone in the pharmaceutical composition. In one embodiment, the at least one extended release portion of the pharmaceutical composition comprises from about 70% to about 80% (w/w) of the total amount of hydrocodone present in the pharmaceutical composition. In certain embodiments, the percentage of hydrocodone present in the at least one extended release portion of the pharmaceutical composition may be about 70%, 71%, 72%, 73%, 74%, 75%, 76%, 77%, 78%, 79%, or 80% of the total amount of hydrocodone. In one embodiment, the percentage of hydrocodone present in the at least one extended release portion of the pharmaceutical composition may be about 75% of the total amount of hydrocodone present in the pharmaceutical composition.

The amount of hydrocodone in the extended release portion(s) also may be expressed as a percentage of the total weight of the extended release portion(s) of the pharmaceutical composition. In one embodiment, the amount of hydrocodone in an extended release portion may range from about 0.5% to about 5.0% (w/w) of the total weight of the such extended release portion of the pharmaceutical composition. In various embodiments, an extended release portion may comprise an amount of hydrocodone that is approximately 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, or 4.0% (w/w) of the total weight of such extended release portion of the pharmaceutical composition. In one embodiment, the amount of hydrocodone in an extended release portion comprises about 0.5% to about 2% (w/w) of the total weight of such extended release portion of the pharmaceutical composition.

In some embodiments, the hydrocodone of the extended release portion(s) may be in the form of particles comprising hydrocodone and at least one excipient. Thus, the at least one extended release portion may comprise particles of hydrocodone which are admixed with the acetaminophen and the extended release component, both of which are detailed below, as well as optional excipients. Suitable hydrocodone particles are described in co-pending application U.S. application Ser. No. 13/166,770, filed Jun. 22, 2011, which is incorporated herein by reference in its entirety. The hydrocodone particles may be coated or uncoated. The average size or average diameter of the particles may vary. In general, the average diameter of the particles may range from about 50 microns to about 2000 microns, from about 100 microns to about 1000 microns, or from about 150 microns to about 200 microns. In one embodiment, the maximum diameter of about 50% of the particles (d50) may be about 40 microns, 50 microns, 100 microns, 150 microns, 200 microns, 250 microns, 300 microns, 400 microns, or 500 microns. In another embodiment, the maximum diameter of about 90% of the particles (d90) may be about 100 microns, 150 microns, 200 microns, 250 microns, 300 microns, 400 microns, or 500 microns.

(ii) Acetaminophen

The extended release portion(s) of the pharmaceutical composition may comprise acetaminophen. The amount of acetaminophen in the extended release portion(s) of the pharmaceutical composition can and will vary. In one embodiment, the at least one extended release portion of the pharmaceutical composition may comprise an amount of acetaminophen ranging from about 40 mg to about 800 mg. In still another embodiment, the at least one extended release portion of the pharmaceutical composition may comprise from about 100 mg to about 600 mg of acetaminophen. In another embodiment, the at least one extended release portion may comprise from about 125 mg to about 400 mg of acetaminophen. In a further embodiment, the amount of acetaminophen in the at least one extended release portion may range from about 160 mg to about 325 mg. In yet another embodiment, the amount of acetaminophen in the at least one extended release portion may be about 100 mg, 110 mg, 120 mg, 125 mg, 130 mg, 135 mg, 140 mg, 145 mg, 150 mg, 155 mg, 160 mg, 162.5 mg, 165 mg, 170 mg, 175 mg, 180 mg, 185 mg, 190 mg, 195 mg, 200 mg, 210 mg, 220 mg, 230 mg, 240 mg, 250 mg, 260 mg, 270 mg, 280 mg, 290 mg, 300 mg, 310 mg, 320 mg, 325 mg, 330 mg, 340 mg, 350 mg, 360 mg, 370 mg, 380 mg, 390 mg, 400 mg, 500 mg, 520 mg, 650 mg, or 780 mg. In one embodiment, the at least one extended release portion comprises about 325 mg of acetaminophen. In another embodiment, the amount of acetaminophen in the at least one extended release portion may be about 250 mg. In yet another embodiment, the amount of acetaminophen in the at least one extended release portion may be about 162.5 mg. In still another embodiment, the amount of acetaminophen in the at least one extended release portion may be about 125 mg.

The extended release portion(s) of the pharmaceutical composition may comprise from about 40% to about 60% of the total amount of acetaminophen present in the pharmaceutical composition. The amount of acetaminophen in the at least one extended release portion may be about 40%, 41%, 42%, 43%, 44%, 45%, 46%, 47%, 48%, 49%, 50%, 51%, 52%, 53%, 54%, 55%, 56%, 57%, 58%, 59%, or 60% (w/w) of the total amount of acetaminophen present in the pharmaceutical composition. In one embodiment, the percentage of acetaminophen present in the extended release portion(s) of the pharmaceutical composition may be about 50% (w/w) of the total amount of acetaminophen.

The amount of acetaminophen in an extended release portion of the pharmaceutical composition may range from about 15% to about 60% (w/w) of the total weight of such extended release portion of the pharmaceutical composition. In various embodiments, an extended release portion may comprise an amount of acetaminophen that is approximately about 15%, 16%, 17%, 18%, 19%, 20%, 21%, 22%, 23%, 24%, 25%, 26%, 27%, 28%, 30%, 32%, 35%, 37%, 40%, 42%, 45%, 47%, 50%, 52%, or 55% (w/w) of the total weight of such extended release portion. In one embodiment, the amount of acetaminophen in an extended release portion may range from about 20% to about 40% (w/w) of the total weight of such extended release portion of the pharmaceutical composition.

(iii) Extended Release Component

The extended release portion(s) of the pharmaceutical composition also comprise(s) an extended release component. Suitable extended release components include polymers, resins, hydrocolloids, hydrogels, and the like.

In one embodiment, the extended release component may comprise at least one extended release polymer. Suitable polymers for inclusion in the at least one extended release portion of the pharmaceutical composition may be linear, branched, dendrimeric, or star polymers, and include synthetic hydrophilic polymers as well as semi-synthetic and naturally occurring hydrophilic polymers. The polymers may be homopolymers or copolymers, such as random copolymers, block copolymers, and graft copolymers. Suitable hydrophilic polymers include, but are not limited to: polyalkylene oxides, particularly poly(ethylene oxide), polyethylene glycol and poly(ethylene oxide)-poly(propylene oxide) copolymers; cellulosic polymers, such as methylcellulose, hydroxymethylcellulose, hydroxyethylcellulose, hydroxypropylcellulose, hydroxypropylmethylcellulose, and carboxymethylcellulose, microcrystalline cellulose, and polysaccharides and their derivatives; acrylic acid and methacrylic acid polymers, copolymers and esters thereof, preferably formed from acrylic acid, methacrylic acid, methyl acrylate, ethyl acrylate, methyl methacrylate, ethyl methacrylate, and copolymers thereof, with each other or with additional acrylate species such as aminoethyl acrylate; maleic anhydride copolymers; polymaleic acid; poly(acrylamides) such as polyacrylamide per se, poly(methacrylamide), poly(dimethylacrylamide), and poly(N-isopropyl-acrylamide); polyalkylene oxides; poly(olefinic alcohol)s such as poly (vinyl alcohol); poly(N-vinyl lactams) such as poly(vinyl pyrrolidone), poly(N-vinyl caprolactam), and copolymers thereof; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxyethylated propylene glycol, and mono and di-polyoxyethylated trimethylene glycol; polyoxyethylated sorbitol and polyoxyethylated glucose; polyoxazolines, including poly(methyloxazoline) and poly(ethyloxazoline); polyvinylamines; polyvinylacetates, including polyvinylacetate per se as well as ethylene-vinyl acetate copolymers, polyvinyl acetate phthalate, and the like, polyimines, such as polyethyleneimine; starch and starch-based polymers; polyurethane hydrogels; chitosan; polysaccharide gums; xanthan gum; zein; and shellac, ammoniated shellac, shellac-acetyl alcohol, and shellac n-butyl stearate. The polymers may be used individually or in combination. Certain combinations will often provide a more controlled release of hydrocodone and acetaminophen than their components when used individually. Suitable combinations include cellulose-based polymers combined with gums, such as hydroxyethyl cellulose or hydroxypropyl cellulose combined with xanthan gum, and poly(ethylene oxide) combined with xanthan gum.

In one embodiment, the extended release polymer(s) may be a cellulosic polymer, such as an alkyl substituted cellulose derivative as detailed above. In terms of their viscosities, one class of exemplary alkyl substituted celluloses includes those whose viscosity is within the range of about 100 to about 110,000 centipoise as a 2% aqueous solution at 20° C. Another class includes those whose viscosity is within the range of about 1,000 to about 4,000 centipoise as a 1% aqueous solution at 20° C.

In one embodiment, the extended release polymer(s) may be a polyalkylene oxide. In another aspect, the polyalkylene oxide may be poly(ethylene) oxide. In a further embodiment, the poly(ethylene) oxide may have an approximate molecular weight between 500,000 Daltons (Da) to about 10,000,000 Da or about 900,000 Da to about 7,000,000 Da. In yet a further embodiment, the poly(ethylene) oxide may have a molecular weight of approximately 600,000 Da, 700,000 Da, 800,000 Da, 900,000 Da, 1,000,000 Da, 2,000, 000 Da, 3,000,000 Da, 4,000,000 Da, 5,000,000 Da, 6,000, 000 Da, 7,000,000 Da, 8,000,000 Da, 9,000,000 Da, or 10,000,000 Da.

In another embodiment, the polyethylene oxide may be any desirable grade of POLYOX™ or any combination thereof. By way of example and without limitation, the POLYOX™ grade may be WSR N-10, WSR N-80, WSR N-750, WSR 205, WSR 1105, WSR N-12K, WSR N-60K, WSR-301, WSR Coagulant, WSR-303, WSR-308, WSR N-3000, UCARFLOC Polymer 300, UCARFLOC Polymer 302, UCARFLOC Polymer 304, and UCARFLOC Polymer 309. In one embodiment, the polyethylene oxide may have an average molecular weight of from about 100,000 Da to about 8,000,000 Da. In another embodiment, the polyethylene oxide may have an average molecular weight of about 100,000 Da, about 200,000 Da, about 300,000 Da, about 400,000 Da, about 600,000 Da, about 900,000 Da, about 1,000,000 Da, about 2,000,000 Da about 4,000,000 Da, about 5,000,000 Da, about 7,000,000 Da, or about 8,000,000 Da. In still another embodiment, the polyethylene oxide may have an average number of repeating ethylene oxide units ($—CH_2CH_2O—$) of about 2,000 to about 160,000. In yet another embodiment, the polyethylene oxide may have an average number of repeating ethylene oxide units of about 2,275, about 4,500, about 6,800, about 9,100, about 14,000, about 20,000, about 23,000, about 45,000, about 90,000, about 114,000, or about 159,000.

The release profile of the extended release pharmaceutical composition disclosed herein will depend partially upon the molecular weight of the extended release polymer(s). In certain embodiments, the polymers are of a moderate to high molecular weight (900,000 Da to 4,000,000 Da) to control release of hydrocodone and/or acetaminophen from the composition via diffusion of the active agent(s) out of the polymer and/or erosion of the polymer. An example of suitable polyethylene oxide polymers are those having molecular weights (viscosity average) on the order of about 900,000 Da to about 2,000,000 Da. Using a lower molecular weight ("MW") polyethylene oxide, such as POLYOX® 1105 (900,000 MW), the release rates for both drugs are higher. Using a higher molecular weight polyethylene oxide (such as POLYOX® N-60K (2,000,000 MW) or POLYOX® WSR-301 (4,000,000 MW) reduces the rate of release for both drugs. In another embodiment of the invention, a hydroxypropylmethylcellulose polymer of such molecular weight is utilized so that the viscosity of a 2% aqueous solution is about 4000 cps to greater than about 100,000 cps.

The release profile of the extended release pharmaceutical composition disclosed herein may also depend upon the amount of the extended release polymer(s) in the pharmaceutical composition. In general, the release rates for hydrocodone and/or acetaminophen may be decreased by increasing the amount of the extended release polymer(s) in the pharmaceutical composition. By way of example and without limitation, the release profile of acetaminophen and hydrocodone may be decreased by increasing the amount of POLYOX® 1105 from about 25% by weight of the ER portion to about 35% by weight of the ER portion.

The amount of extended release polymer or polymers present in the extended release portion(s) of the pharmaceutical composition can and will vary. In one embodiment, the polymer present in an extended release portion of the pharmaceutical composition may range from about 15% to about 70% (w/w), or about 20% to about 60% (w/w), or about 25% to about 55% (w/w) of the total weight of such extended release portion of the dosage form. In another embodiment, the amount of polymer present in an extended release portion of the pharmaceutical composition may range from about 30% to about 50% (w/w) of the total weight of such extended release portion. In still another embodiment, the amount of polymer present in an extended release portion of the pharmaceutical composition may range from about 35% to about 45% (w/w) of the total weight of such extended release portion. In yet another embodiment, the amount of polymer present in an extended release portion of the pharmaceutical composition may be about 30%, 35%, 40%, 45%, 50%, 55%, or 60% (w/w) of the total weight of such extended release portion. In one embodiment, the amount of polymer present in an extended release portion of the pharmaceutical composition may be about 35% (w/w) of the total weight of such extended release portion. In another embodiment, the amount of polymer present in an extended release portion of the pharmaceutical composition may be about 45% (w/w) of the total weight of such extended release portion. In one embodiment, the ER layer swells upon imbibition of fluid to a size which is about 15%, 20%, 25%, 30%, 35% 40%, 45%, 50%, 55%, 60%, 65%, 70%, 75%, 80%, 85%, 90%, 95% or 100% larger than the size of the ER layer prior to imbibition of fluid. In another embodiment, the ER layer swells upon imbibition of fluid to a size at least about 25% larger than the size of the ER layer prior to imbibition of fluid within about 15 minutes of the start of fluid imbibition. In still another embodiment, the ER layer swells upon imbibition of fluid to a size at least about 100% larger than the size of the ER layer prior to imbibition of fluid within about 45 min, 50 min, 60 min, 75 min, or 90 min of the start of fluid imbibitions.

(iv) Excipients

The extended release portion(s) of the pharmaceutical composition may further comprise at least one excipient. Suitable excipients include binders, fillers, lubricants, antioxidants, chelating agents, and color agents.

In one embodiment, the extended release portion(s) of the pharmaceutical composition may comprise at least one binder. Suitable binders include, without limit, starches (including corn starch and pregelatinized starch), gelatin, sugars (including sucrose, glucose, dextrose and lactose), polyethylene glycol, polyols, polyvinylalcohols, C12-C18 fatty acid alcohols, waxes, gums (e.g., guar gum, arabic gum, acacia gum, xanthan gum, etc.), gelatin, pectin, sodium alginate, polyvinylpyrrolidone, cellulosic polymers (including hydroxypropyl cellulose, hydroxypropyl methylcellulose, hydroxylcellulose, methylcellulose, microcrystalline cellulose, ethylcellulose, hydroxyethyl cellulose, and the like), polyacrylamides, and polyvinyloxoazolidone. In one embodiment, the amount of binder or binders in an extended release portion of the pharmaceutical composition may range from about 0.5% to about 8.0% (w/w) of such extended release portion. In various embodiments, an extended release portion of the pharmaceutical composition may comprise at least one binder that is present in an amount that is about 0.5%, 1.0%, 1.1%, 1.2%, 1.3%, 1.4%, 1.5%, 2.0%, 2.5%, 3.0%, 3.5%, 4.0%, 4.5%, 5.0%, 5.5%, 6.0%, 6.5%, 7.0%, 7.5%, or 8.0% (w/w) of such extended release portion of the dosage form.

In another embodiment, the extended release portion(s) of the pharmaceutical composition may comprise at least one filler. Suitable fillers include but are not limited to microcrystalline cellulose (MCC), dibasic calcium phosphate, tribasic calcium phosphate, magnesium carbonate, magnesium oxide, calcium silicate, magnesium aluminum silicate, silicon dioxide, titanium dioxide, alumina, talc, kaolin, polyvinylpyrrolidone, dibasic calcium sulfate, tribasic calcium sulfate, starch, calcium carbonate, magnesium carbonate, carbohydrates, modified starches, lactose, sucrose, dextrose, mannitol, sorbitol, and inorganic compounds. In one embodiment, the amount of filler or fillers in an extended release portion may range from about 2% to about 50% (w/w) of the total weight of such extended release portion. In various embodiments, an extended release portion of the pharmaceutical composition may comprise at least one filler that is present in an amount that is about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% (w/w) of such extended release portion of the dosage form.

In a further embodiment, the extended release portion(s) of the pharmaceutical composition may further comprise a lubricant. Useful lubricants include magnesium stearate, calcium stearate, stearic acid, and hydrogenated vegetable oil (preferably comprised of hydrogenated and refined triglycerides of stearic and palmitic acids). The lubricant may be present in an amount ranging from about 0.1% to about 3.0% (w/w) of the total weight of such extended release portion. In certain embodiments, the amount of lubricant in an extended release portion may be about 0.25%, 0.5%, 0.75%, 1.0%, 1.5%, 1.75%, 1.80%, 1.85%, 1.90%, or 2.0% (w/w) of the total weight of such extended release portion.

In yet another embodiment, the extended release portion(s) of the pharmaceutical composition may comprise at least one antioxidant. Suitable antioxidants include, without limit, ascorbic acid, citric acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiarybutylphenol, alphatocopherol, and propylgallate. The amount of antioxidant present in an extended release portion of the pharmaceutical composition may range from about 0.01% to about 4.0%, or from about 0.02% to about 0.10% (w/w). In various embodiments, the amount of antioxidant present in an extended release portion of the pharmaceutical composition may be about 0.01%, 0.02%, 0.03%, 0.04%, 0.05%, 0.06%, 0.07%, 0.08%, 0.09%, 0.10%, 0.12%, 0.14%, 0.16%, 0.18%. 0.20%, 0.25%, 0.50%, 0.75%, 1.00%, 1.50%, or 2.00% (w/w) of the total weight of such extended release portion.

In still another embodiment, the extended release portion(s) of the pharmaceutical composition may comprise at least one chelating agent. Suitable chelating agents include ethylenediamine tetracetic acid (EDTA) and its salts, N-(hydroxy-ethyl)ethylenediaminetriacetic acid, nitrilotriacetic acid (NIA), ethylene-bis(oxyethylene-nitrilo)tetraacetic acid, 1,4,7,10-tetraazacyclodo-decane-N,N',N",N'''-tetraacetic acid, 1,4,7,10-tetraaza-cyclododecane-N,N',N"-triacetic acid, 1,4,7-tris(carboxymethyl)-10-(2'-hydroxypropyl)-1,4,7,10-tetraazocyclodecane, 1,4,7-triazacyclonane-N,N',N"-triacetic acid, 1,4,8,11-tetraazacyclotetra-decane-N,N',N",N'''-tetraacetic acid; diethylenetriamine-pentaacetic acid (DTPA), ethylenedicysteine, bis(aminoethanethiol)carboxylic acid, triethylenetetraamine-hexaacetic acid, and 1,2-diaminocyclohexane-N,N,N',N'-tetraacetic acid. In one embodiment, the chelating agent is the sodium salt of EDTA. The amount of chelating agent present in an extended release portion of the pharmaceutical composition may range from about 0.001% to about 0.20% (w/w) of such extended release portion. In some embodiments, the amount of chelating agent present in an extended release portion of the pharmaceutical composition may be about 0.001%, 0.002%, 0.003%, 0.004%, 0.005%, 0.01%, 0.02%, 0.03%, 0.04%, 0.05%, 0.06%, 0.07%, 0.08%, 0.09%, 0.10%, 0.11%, 0.12%, 0.13%, 0.14%, or 0.15% (w/w) of the total weight of such extended release portion.

In an alternate embodiment, the extended release portion(s) of the pharmaceutical composition may comprise a color agent. Suitable color additives include, but are not limited to, food, drug and cosmetic colors (FD&C), drug and cosmetic colors (D&C), and external drug and cosmetic colors (Ext. D&C). In various embodiments, the amount of color agent present in an extended release portion may range from about 2.0% to about 5.0% (w/w) of such extended release portion of the dosage form. In other embodiments, the amount of color agent present in an extended release portion may be about 1.0%, 1.5%, 2.0%, 2.5%, 3.0%, 3.5%, 4.0%, 4.5%, or 5.0% (w/w) of such extended release portion.

(c) Dosage Forms of the Pharmaceutical Composition

The physical form of the pharmaceutical composition disclosed herein can and will vary. In general, the pharmaceutical composition is a solid dosage form comprising at least one extended release portion and, optionally, at least one immediate release portion. Suitable solid dosage forms include tablets, caplets, capsules, encapsulated beads, and gelcaps. Non-limiting types of tablets include coated tablets, uncoated tablets, bilayer tablets, multiparticle tablets, monolithic tablets, matrix tablets, compressed tablets, and molded tablets. Non-limiting types of capsules include hard capsules and multi-layer capsules.

In one embodiment, the dosage form may be a capsule. Non-limiting examples of suitable hard capsules include hard starch capsules, hard gelatin capsules, hard cellulose capsules, and hydrogel capsules. In one example, the core of the capsule may comprise the at least one extended release portion and the shell of the capsule may comprise the at least one immediate release portion of the composition. In another example, the core of the capsule may comprises one extended release portion, comprising hydrocodone, acetaminophen and an extended release component, and the shell of the capsule may comprise one immediate release portion of the composition comprising hydrocodone and acetaminophen. In yet another example, the core of the capsule may comprise two extended release portions, each comprising an extended release component and one of hydrocodone or acetaminophen, and the shell of the capsule may comprise two immediate release portions of the composition, each comprising one of the hydrocodone and the acetaminophen. In still another embodiment, the dosage form may be a sustained release capsule comprising the hydrocodone or acetaminophen and exhibiting immediate release and/or extended release properties.

In another embodiment, the dosage form may be a tablet comprising at least one extended release portion and at least one immediate release portion. The at least one immediate release portion may be adjacent to, abutting, or surrounding the at least one extended release portion. In one embodiment, the dosage form may be a bilayer tablet comprising one extended release layer comprising the hydrocodone and the acetaminophen and one immediate release layer comprising the hydrocodone and the acetaminophen. In still another embodiment, the dosage form may be a sustained release tablet comprising the hydrocodone and/or acetaminophen and exhibiting immediate release and/or extended release properties. The bilayer tablet may comprise a coating.

In another embodiment, the dosage form may be a multilayer tablet comprising two extended release portions, each comprising one of the hydrocodone and the acetaminophen, and one immediate release portion comprising both the hydrocodone and the acetaminophen. In yet another embodiment, the dosage form may be a multilayer tablet comprising two extended release portions, each comprising one of the hydrocodone and the acetaminophen, and two immediate release portions, each comprising one of the hydrocodone and the acetaminophen. In still another embodiment, the dosage form may be a sustained release tablet comprising the hydrocodone or acetaminophen and exhibiting immediate release and/or extended release properties.

In certain embodiments, the tablet may have a friability of no greater than about 0.1%, 0.2%, 0.3%, 0.4%, 0.5%, 0.7% or 1.0%. In another embodiment, the tablet may have a friability of greater than 0 but less that about 1.0%, greater than 0 but less than about 0.5%, greater than 0 but less than about 0.3%, or greater than 0 but less than about 0.2%. In still another embodiment, the tablet may have a friability of zero.

In another embodiment, the tablet may have a hardness of at least about 10 Kilopond (also known as kilopons) (kp). In some embodiments, the tablet may have a hardness of about 9 kp to about 25 kp, or about 12 kp to about 20 kp. In further embodiments, the tablet may have a hardness of about 11 kp, 12 kp, 13 kp, 14 kp, 15 kp, 16 kp, 17 kp, 18 kp, 19 kp, or 20 kp.

In additional embodiments, the tablet may have a content uniformity of from about 85 to about 115 percent by weight or from about 90 to about 110 percent by weight, or from about 95 to about 105 percent by weight. In other embodiments, the content uniformity may have a relative standard deviation (RSD) equal to or less than about 3.5%, 3.0%, 2.5%, 2.0%, 1.5%, 1.0%, or 0.5%.

In still other embodiments, prior to administration to a patient or immersion in fluid, the pharmaceutical composition may have (i) a length of approximately 18 mm, 18.01 mm, 18.02 mm, 18.03 mm, 18.04 mm, 18.05 mm, 18.06 mm, 18.07 mm, 18.08 mm, 18.09 mm, 18.1 mm, 18.11 mm, 18.12 mm, 18.13 mm, 18.14 mm, 18.15 mm, 18.16 mm, 18.17 mm, 18.18 mm, 18.19 mm, 18.2 mm, 18.21 mm, 18.22 mm, 18.23 mm, 18.24 mm, 18.25 mm, 18.26 mm, 18.27 mm, 18.28 mm, 18.29 mm, 18.3 mm, 18.31 mm, 18.32 mm, 18.33 mm, 18.34 mm, 18.35 mm, 18.36 mm, 18.37 mm, 18.38 mm, 18.39 mm, 18.4 mm, 18.41 mm, 18.42 mm, 18.43 mm, 18.44 mm, 18.45 mm, 18.46 mm, 18.47 mm, 18.48 mm, 18.49 mm, 18.5 mm, 18.51 mm, 18.52 mm, 18.53 mm, 18.54 mm, 18.55 mm, 18.56 mm, 18.57 mm, 18.58 mm, 18.59 mm, 18.6 mm, 18.61 mm, 18.62 mm, 18.63 mm, 18.64 mm, 18.65 mm, 18.66 mm, 18.67 mm, 18.68 mm, 18.69 mm, 18.7 mm, 18.71 mm, 18.72 mm, 18.73 mm, 18.74 mm, 18.75 mm, 18.76 mm, 18.77 mm, 18.78 mm, 18.79 mm, 18.8 mm, 18.81 mm, 18.82 mm, 18.83 mm, 18.84 mm, 18.85 mm, 18.86 mm, 18.87 mm, 18.88 mm, 18.89 mm, 18.9 mm, 18.91 mm, 18.92 mm, 18.93 mm, 18.94 mm, 18.95 mm, 18.96 mm, 18.97 mm, 18.98 mm, 18.99 mm, 19 mm, 19.01 mm, 19.02 mm, 19.03 mm, 19.04 mm, 19.05 mm, 19.06 mm, 19.07 mm, 19.08 mm, 19.09 mm, 19.1 mm, 19.11 mm, 19.12 mm, 19.13 mm, 19.14 mm, 19.15 mm, 19.16 mm, 19.17 mm, 19.18 mm, 19.19 mm, 19.2 mm, 19.21 mm, 19.22 mm, 19.23 mm, 19.24 mm, 19.25 mm, 19.26 mm, 19.27 mm, 19.28 mm, 19.29 mm, 19.3 mm, 19.31 mm, 19.32 mm, 19.33 mm, 19.34 mm, 19.35 mm, 19.36 mm, 19.37 mm, 19.38 mm, 19.39 mm, 19.4 mm, 19.41 mm, 19.42 mm, 19.43 mm, 19.44 mm, 19.45 mm, 19.46 mm, 19.47 mm, 19.48 mm, 19.49 mm, 19.5 mm, 19.51 mm, 19.52 mm, 19.53 mm, 19.54 mm, 19.55 mm, 19.56 mm, 19.57 mm, 19.58 mm, 19.59 mm 19.6 mm, 19.61 mm, 19.62 mm, 19.63 mm, 19.64 mm, 19.65 mm, 19.66 mm, 19.67 mm, 19.68 mm, 19.69 mm, 19.7 mm, 19.71 mm, 19.72 mm, 19.73 mm, 19.74 mm, 19.75 mm, 19.76 mm, 19.77 mm, 19.78 mm, 19.79 mm, 19.8 mm, 19.81 mm, 19.82 mm, 19.83 mm, 19.84 mm, 19.85 mm, 19.86 mm, 19.87 mm, 19.88 mm, 19.89 mm, 19.9 mm, 19.91 mm, 19.92 mm, 19.93 mm, 19.94 mm, 19.95 mm, 19.96 mm, 19.97 mm, 19.98 mm, 19.99 mm, or 20 mm as measured on the major axis, (ii) a width of approximately 11 mm, 11.01 mm, 11.02 mm, 11.03 mm, 11.04 mm, 11.05 mm, 11.06 mm, 11.07 mm, 11.08 mm, 11.09 mm, 11.1 mm, 11.11 mm, 11.12 mm, 11.13 mm, 11.14 mm, 11.15 mm, 11.16 mm, 11.17 mm, 11.18 mm, 11.19 mm, 11.2 mm, 11.21 mm, 11.22 mm, 11.23 mm, 11.24 mm, 11.25 mm, 11.26 mm, 11.27 mm, 11.28 mm, 11.29 mm, 11.3 mm, 11.31 mm, 11.32 mm, 11.33 mm, 11.34 mm, 11.35 mm, 11.36 mm, 11.37 mm, 11.38 mm, 11.39 mm, 11.4 mm, 11.41 mm, 11.42 mm, 11.43 mm, 11.44 mm, 11.45 mm, 11.46 mm, 11.47 mm, 11.48 mm, 11.49 mm, 11.5 mm, 11.51 mm, 11.52 mm, 11.53 mm, 11.54 mm, 11.55 mm, 11.56 mm, 11.57 mm, 11.58 mm, 11.59 mm, 11.6 mm, 11.61 mm, 11.62 mm, 11.63 mm, 11.64 mm, 11.65 mm, 11.66 mm, 11.67 mm, 11.68 mm, 11.69 mm, 11.7 mm, 11.71 mm, 11.72 mm, 11.73 mm, 11.74 mm, 11.75 mm, 11.76 mm, 11.77 mm, 11.78 mm, 11.79 mm, 11.8 mm, 11.81 mm, 11.82 mm, 11.83 mm, 11.84 mm, 11.85 mm, 11.86 mm, 11.87 mm, 11.88 mm, 11.89 mm, 11.9 mm, 11.91 mm, 11.92 mm, 11.93 mm, 11.94 mm, 11.95 mm, 11.96 mm, 11.97 mm, 11.98 mm, 11.99 mm, 12 mm, 12.01 mm, 12.02 mm, 12.03 mm, 12.04 mm, 12.05 mm, 12.06 mm, 12.07 mm, 12.08 mm, 12.09 mm, 12.1 mm, 12.11 mm, 12.12 mm, 12.13 mm, 12.14 mm, 12.15 mm, 12.16 mm, 12.17 mm, 12.18 mm, 12.19 mm, 12.2 mm, 12.21 mm, 12.22 mm, 12.23 mm, 12.24 mm, 12.25 mm, 12.26 mm, 12.27 mm, 12.28 mm, 12.29 mm, 12.3 mm, 12.31 mm, 12.32 mm, 12.33 mm, 12.34 mm, 12.35 mm, 12.36 mm, 12.37 mm, 12.38 mm, 12.39 mm, 12.4 mm, 12.41 mm, 12.42 mm, 12.43 mm, 12.44 mm, 12.45 mm, 12.46 mm, 12.47 mm, 12.48 mm, 12.49 mm, 12.5 mm, 12.51 mm, 12.52 mm, 12.53 mm, 12.54 mm, 12.55 mm, 12.56 mm, 12.57 mm, 12.58 mm, 12.59 mm, 12.6 mm, 12.61 mm, 12.62 mm, 12.63 mm, 12.64 mm, 12.65 mm, 12.66 mm, 12.67 mm, 12.68 mm, 12.69 mm, 12.7 mm, 12.71 mm, 12.72 mm, 12.73 mm, 12.74 mm, 12.75 mm, 12.76 mm, 12.77 mm, 12.78 mm, 12.79 mm, 12.8 mm, 12.81 mm, 12.82 mm, 12.83 mm, 12.84 mm, 12.85 mm, 12.86 mm, 12.87 mm, 12.88 mm, 12.89 mm, 12.9 mm, 12.91 mm, 12.92 mm, 12.93 mm, 12.94 mm, 12.95 mm, 12.96 mm, 12.97 mm, 12.98 mm, 12.99 mm, or 13 mm, and (iii) a height or thickness of approximately 5 mm, 5.01 mm, 5.02 mm, 5.03 mm, 5.04 mm, 5.05 mm, 5.06 mm, 5.07 mm, 5.08 mm, 5.09 mm, 5.1 mm, 5.11 mm, 5.12 mm, 5.13 mm, 5.14 mm, 5.15 mm, 5.16 mm, 5.17 mm, 5.18 mm, 5.19 mm, 5.2 mm, 5.21 mm, 5.22 mm, 5.23 mm, 5.24 mm, 5.25 mm, 5.26 mm, 5.27 mm, 5.28 mm, 5.29 mm, 5.3 mm, 5.31 mm, 5.32 mm, 5.33 mm, 5.34 mm, 5.35 mm, 5.36 mm, 5.37 mm, 5.38 mm, 5.39 mm, 5.4 mm, 5.41 mm, 5.42 mm, 5.43 mm, 5.44 mm, 5.45 mm, 5.46 mm, 5.47 mm, 5.48 mm, 5.49 mm, 5.5 mm, 5.51 mm, 5.52 mm, 5.53 mm, 5.54 mm, 5.55 mm, 5.56 mm, 5.57 mm, 5.58 mm, 5.59 mm, 5.6 mm, 5.61 mm, 5.62 mm, 5.63 mm, 5.64 mm, 5.65 mm, 5.66 mm, 5.67 mm, 5.68 mm, 5.69 mm, 5.7 mm, 5.71 mm, 5.72 mm, 5.73 mm, 5.74 mm, 5.75 mm, 5.76 mm, 5.77 mm, 5.78 mm, 5.79 mm, 5.8 mm, 5.81 mm, 5.82 mm, 5.83 mm, 5.84 mm, 5.85 mm, 5.86 mm, 5.87 mm, 5.88 mm, 5.89 mm, 5.9 mm, 5.91 mm, 5.92 mm, 5.93 mm, 5.94 mm, 5.95 mm, 5.96 mm, 5.97 mm, 5.98 mm, 5.99 mm, or 6 mm. In yet another embodiment, the pharmaceutical composition may have (i) a length of approximately 19.1 mm, 19.11 mm, 19.12 mm, 19.13 mm, 19.14 mm, 19.15 mm, 19.16 mm, 19.17 mm, 19.18 mm, 19.19 mm, 19.2 mm, 19.21 mm, 19.22 mm, 19.23 mm, 19.24 mm, 19.25 mm, 19.26 mm, 19.27 mm, 19.28 mm, 19.29 mm, or 19.3 mm as measured on the major axis, (ii) a width of approximately 12.4 mm, 12.41 mm, 12.42 mm, 12.43 mm, 12.44 mm, 12.45 mm, 12.46 mm, 12.47 mm, 12.48 mm, 12.49 mm, or 12.5 mm, and (iii) a height or thickness of approximately 5.6 mm, 5.61 mm, 5.62 mm, 5.63 mm, 5.64 mm, 5.65 mm, 5.66 mm, 5.67 mm, 5.68 mm, 5.69 mm, 5.7 mm, 5.71 mm, 5.72 mm, 5.73 mm, 5.74 mm, 5.75 mm, 5.76 mm, 5.77 mm, 5.78 mm, 5.79 mm, or 5.8 mm.

In additional embodiments, the pharmaceutical composition may expand upon immersion in fluid to have (i) a length of about 18.5 mm, 18.6 mm, 18.7 mm, 18.8 mm, 18.9 mm, 19 mm, 19.1 mm, 19.2 mm, 19.3 mm, 19.4 mm, 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, or 21 mm; and (ii) a width of about 11 mm, 11.1 mm, 11.2 mm, 11.3 mm, 11.4 mm, 11.5 mm, 11.6 mm, 11.7 mm, 11.8 mm, 11.9 mm, 12 mm, 12.1 mm, 12.2 mm, 12.3 mm, 12.4 mm, 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, or 14 mm within about 5 minutes of immersion in fluid. In other embodiments, the pharmaceutical composition may expand upon immersion in fluid to (i) a length of about 18.5 mm, 18.6 mm, 18.7 mm, 18.8 mm, 18.9 mm, 19 mm, 19.1 mm, 19.2 mm, 19.3 mm, 19.4 mm, 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, 21 mm, 21.1 mm, 21.2 mm, 21.3 mm, 21.4 mm, 21.5 mm, 21.6 mm, 21.7 mm, 21.8 mm, 21.9 mm, or 22 mm; and (ii) a width of about 11 mm, 11.1 mm, 11.2 mm, 11.3 mm, 11.4 mm, 11.5 mm, 11.6 mm, 11.7 mm, 11.8 mm, 11.9 mm, 12 mm, 12.1 mm, 12.2 mm, 12.3 mm, 12.4 mm, 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, or 15 mm within about 10 minutes to about 15 minutes of immersion in fluid. In still other embodiments, the pharmaceutical composition may expand upon immersion in fluid to (i) a length of about 19 mm, 19.1 mm, 19.2 mm, 19.3 mm, 19.4 mm, 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, 21 mm, 21.1 mm, 21.2 mm, 21.3 mm, 21.4 mm, 21.5 mm, 21.6 mm, 21.7 mm, 21.8 mm, 21.9 mm, 22 mm, 22.1 mm, 22.2 mm, 22.3 mm, 22.4 mm, or 22.5 mm; and (ii) a width of about 12 mm, 12.1 mm, 12.2 mm, 12.3 mm, 12.4 mm, 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, or 15 mm within about 20 minutes to about 25 minutes of immersion in fluid. In additional embodiments, the pharmaceutical composition may expand upon immersion in fluid to (i) a length of about 19 mm, 19.1 mm, 19.2 mm, 19.3 mm, 19.4 mm, 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, 21 mm, 21.1 mm, 21.2 mm, 21.3 mm, 21.4 mm, 21.5 mm, 21.6 mm, 21.7 mm, 21.8 mm, 21.9 mm, 22 mm, 22.1 mm, 22.2 mm, 22.3 mm, 22.4 mm, 22.5 mm, 22.6 mm, 22.7 mm, 22.8 mm, 22.9 mm, or 23 mm; and (ii) a width of about 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, or 15 mm within about 30 minutes to about 35 minutes of immersion in fluid. In still other embodiments, the pharmaceutical composition may expand upon immersion in fluid to (i) a length of about 18 mm, 18.1 mm, 18.2 mm, 18.3 mm, 18.4 mm, 18.5 mm, 18.6 mm, 18.7 mm, 18.8 mm, 18.9 mm, 19 mm, 19.1 mm, 19.2 mm, 19.3 mm, 19.4 mm, 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, 21 mm, 21.1 mm, 21.2 mm, 21.3 mm, 21.4 mm, 21.5 mm, 21.6 mm, 21.7 mm, 21.8 mm, 21.9 mm, 22 mm, 22.1 mm, 22.2 mm, 22.3 mm, 22.4 mm, 22.5 mm, 22.6 mm, 22.7 mm, 22.8 mm, 22.9 mm, 23 mm, 23.1 mm, 23.2 mm, 23.3 mm, 23.4 mm, or 23.5; (ii) a width of about 11.5 mm, 11.6 mm, 11.7 mm, 11.8 mm, 11.9 mm, 12 mm, 12.1 mm, 12.2 mm, 12.3 mm, 12.4 mm, 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, 15 mm, 15.1 mm, 15.2 mm, 15.3 mm, 15.4 mm, 15.5 mm, 15.6 mm, 15.7 mm, 15.8 mm, 15.9 mm, or 16 mm; and (iii) a height or thickness of about 5.5 mm, 5.6 mm, 5.7 mm, 5.8 mm, 5.9 mm, 6 mm, 6.1 mm, 6.2 mm, 6.3 mm, 6.4 mm, 6.5 mm, 6.6 mm, 6.7 mm, 6.8 mm, 6.9 mm, or 7 mm within about 50 minutes to about 55 minutes of immersion in fluid. In yet another embodiment, the pharmaceutical composition may expand upon immersion in fluid to (i) a length of about 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, 21 mm, 21.1 mm, 21.2 mm, 21.3 mm, 21.4 mm, 21.5 mm, 21.6 mm, 21.7 mm, 21.8 mm, 21.9 mm, 22 mm, 22.1 mm, 22.2 mm, 22.3 mm, 22.4 mm, 22.5 mm, 22.6 mm, 22.7 mm, 22.8 mm, 22.9 mm, 23 mm, 23.1 mm, 23.2 mm, 23.3 mm, 23.4 mm, or 23.5; (ii) a width of about 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, 15 mm, 15.1 mm, 15.2 mm, 15.3 mm, 15.4 mm, 15.5 mm, 15.6 mm, 15.7 mm, 15.8 mm, 15.9 mm, or 16 mm; and (iii) a height or thickness of about 5.5 mm, 5.6 mm, 5.7 mm, 5.8 mm, 5.9 mm, 6 mm, 6.1 mm, 6.2 mm, 6.3 mm, 6.4 mm, 6.5 mm, 6.6 mm, 6.7 mm, 6.8 mm, 6.9 mm, or 7 mm within about 60 minutes of immersion in fluid.

In yet another embodiment, the length of the pharmaceutical composition increases by about 4%, 4.25%, 4.5% 4.75%, 5%, 5.25%, 5.5%, 5.75%, 6%, 6.25%, 6.5%, 6.75%, 7%, 7.25%, 7.5%, 7.75% 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, or 13% within about 10 minutes of immersion in fluid. In still another embodiment, the length of the pharmaceutical composition increases by about 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, or 15% within about 15 minutes of immersion in fluid. In yet another embodiment, the length of the pharmaceutical composition increases by about 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, or 15% within about 20 minutes of immersion in fluid. In a further embodiment, the length of the pharmaceutical composition increases by about 7%, 7.25%, 7.5%, 7.75% 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, or 18% within about 30 minutes of immersion in fluid. In another embodiment, the length of the pharmaceutical composition increases by about 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, or 19% within about 45 minutes of immersion in fluid. In yet another embodiment, the length of the pharmaceutical composition increases by about 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, or 19% within about 55 minutes of immersion in fluid. In still another embodiment, the length of the pharmaceutical composition increases by about 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, or 20% within about 60 minutes of immersion in fluid.

In a further embodiment, the width of the pharmaceutical composition increases by about 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, or 15% within about 10 minutes of immersion in fluid. In still another embodiment, the width of the pharmaceutical composition increases by about 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, or 18%, within about 15 minutes of immersion in fluid. In yet another embodiment, the width of the pharmaceutical composition increases by about 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, or 18%, within about 20 minutes of immersion in fluid. In a further embodiment, the width of the pharmaceutical composition increases by about 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, 20%, 20.25%, 20.5%, 20.75%, 21%, 21.25%, 21.5%, 21.75%, 22%, 22.25%, 22.5%, 22.75%, 23%, 23.25%, 23.5%, 23.75%, or 24% within about 30 minutes of immersion in fluid. In another embodiment, the width of the pharmaceutical composition increases by about 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, 20.0%, 20.25%, 20.5%, 20.75%, 21%, 21.25%, 21.5%, 21.75%, 22%, 22.25%, 22.5%, 22.75%, 23%, 23.25%, 23.5%, 23.75%, 24%, 24.25%, 24.5%, 24.75%, or 25% within about 45 minutes of immersion in fluid. In yet another embodiment, the width of the pharmaceutical composition increases by about 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, 20.25%, 20.5%, 20.75%, 21%, 21.25%, 21.5%, 21.75%, 22%, 22.25%, 22.5%, 22.75%, 23%, 23.25%, 23.5%, 23.75%, 24%, 24.25%, 24.5%, 24.75%, or 25% within about 55 minutes of immersion in fluid. In still another embodiment, the width of the pharmaceutical composition increases by about 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, 20%, 20.25%, 20.5%, 20.75%, 21%, 21.25%, 21.5%, 21.75%, 22%, 22.25%, 22.5%, 22.75%, 23%, 23.25%, 23.5%, 23.75%, 24%, 24.25%, 24.5%, 24.75%, 25%, 25.25%, 25.5%, 25.75%, or 26% within about 60 minutes of immersion in fluid.

The pharmaceutical composition disclosed herein includes one or more dosage forms that are designed to achieve the therapeutic concentrations of the active ingredients. In some embodiments, therefore, a therapeutically effective dose of the pharmaceutical composition may comprise one dosage form. In other embodiments, a therapeutically effective dose of the pharmaceutical composition may comprise two dosage forms. In additional embodiments, a therapeutically effective dose of the pharmaceutical composition may comprise three or more dosage forms.

(d) Abuse and Tamper Resistant Properties of the Composition

Extended release pain medications have provided many benefits to patients in the management of their chronic pain by providing a sustained release over time of a larger quantity of drug than is typically contained in an immediate release formulation. Consequently, these dosage forms (especially if they contain opioids) are attractive targets for drug abusers looking to defeat the extended release formulation to allow immediate bolus administration or "dose-dumping" of the entire drug contents of the dosage form.

Dosage forms of the pharmaceutical composition disclosed herein may be more resistant to crushing, grinding, pulverizing, or other common means used to produce a powder than an immediate release product. Accordingly, some embodiment forms are tamper resistant and less prone to abuse or misuse. For example, certain embodiments may not be crushed into a powder and snorted. Additionally, some embodiments comprising an extended release polymer may not be crushed, mixed with an aqueous solution, and injected (i.e., the resultant mixture becomes extremely viscous and cannot be drawn into a syringe.

For example, dosage forms of the pharmaceutical composition disclosed herein form a pasty semi-solid mixture when dissolved. Thus, the pharmaceutical composition is difficult to draw into a syringe and inject intravenously. The yield of active pharmaceutical ingredient(s) obtained from the pharmaceutical composition is also low (less than 20%).

Further, dosage forms of the pharmaceutical composition disclosed herein cannot easily be snorted. In order for a drug abuser to successfully snort a drug obtained from a dosage form, he must prepare a crushed, finely divided powder form of the dosage form for insufflating the powder into the nasal cavity. However, the pharmaceutical compositions disclosed herein form a clumpy, solid mass and do not allow acceptable absorption through the nasal tissue.

Dosage forms of the pharmaceutical composition disclosed herein also do not allow "dose dumping" caused by the deliberate introduction of alcohol into a drug abuser's stomach which accelerates the release of active ingredient(s) from the time-release formulation. The pharmaceutical compositions disclosed herein are resistant to the accelerated release of active ingredient(s).

In addition, dosage forms of the pharmaceutical composition disclosed herein do not allow for "free basing." Successful free basing by a drug abuser requires the generation of a salt free form of the active pharmaceutical ingredient(s). This requires physical and chemical manipulation to release the active pharmaceutical ingredient(s) from its salt(s) and selective extraction from other matrix excipients. The pharmaceutical composition disclosed herein cannot be easily manipulated to generate a free base preparation.

Moreover, the tamper resistance properties of the pharmaceutical compositions disclosed herein may be increased by increasing the average molecular weight of the extended release polymer used in the pharmaceutical composition. In another embodiment, the tamper resistance properties of the pharmaceutical compositions disclosed herein may be increased by increasing the amount of the extended release polymer used in the pharmaceutical composition.

In further embodiments, the solid oral dosage forms of the pharmaceutical compositions disclosed herein exhibit substantial differences in the release profiles of hydrocodone and acetaminophen when the dosage forms are crushed or ground. Indeed, the intact solid oral dosage forms surprisingly exhibit a higher release rate of both active ingredients than one that is crushed or ground. This suggests that upon grinding or crushing the solid oral dosage forms disclosed herein, the immediate release portion and extended release portion of the dosage form combine, and the hydration and swelling of the polymer(s) in the extended release portion of the dosage form retards the release of the hydrocodone and acetaminophen in the immediate release portion. Hence the incorporation of the ground or crushed components from the immediate release portion into a mixture with the ground or crushed components of the extended release portion causes the pharmaceutical composition to lose its immediate release characteristics. This feature may effectively negate a drug abuser's purpose for crushing the solid oral dosage form in the first place—to obtain an early onset of analgesia. Thus, this is an unexpected tamper resistant property of the pharmaceutical compositions disclosed herein.

In another embodiment, as the amount of hydrocodone in the pharmaceutical composition increases, so does the duration of gastric retention after administration to a subject. Consequently, if a subject either intentionally or accidentally ingests a larger dose of the pharmaceutical composition than prescribed, the pharmaceutical composition will be retained in the stomach for a longer time period than an IR or traditional ER pharmaceutical composition, thereby giving a medical provider additional time to perform gastric lavage, induce vomiting, or administer activated charcoal to prevent the body from absorbing the hydrocodone. In a further embodiment, the pharmaceutical composition provides a medical provider with about an additional 15 minutes, 30 minutes, 45 minutes, 60 minutes, 75 minutes, 90 minutes, 105 minutes, 2.0 hours, 2.25 hours, 2.5 hours, 2.75 hours, 3.0 hours, 3.25 hours, 3.5 hours, 3.75 hours, or 4 hours in which to prevent the absorption of hydrocodone in the subject. In another embodiment, the pharmaceutical composition provides a medical provider with sufficient time to treat a subject who has overdosed on hydrocodone so that death, difficulty breathing, cardiac arrest, and limp muscles do not occur in the subject.

In yet another embodiment, if vomiting is induced or naturally occurs as a result of an increased dose of hydrocodone, the entire pharmaceutical composition is expelled from the subject. Thus, toxic concentrations of the hydrocodone due to absorption into the subject's blood are prevented by removing the further release of hydrocodone. In still another embodiment, if vomiting is induced or naturally occurs as a result of the increased dose of hydrocodone about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the pharmaceutical composition is expelled from the subject. In yet another embodiment, if vomiting is induced or naturally occurs within about 30 minutes to about 60 minutes after ingestion of the increased dose of hydrocodone about 50% to about 65% of the hydrocodone dose is expelled from the subject.

(e) In vitro Release Properties of the Composition

The in vitro release rates of hydrocodone and acetaminophen from the pharmaceutical compositions disclosed herein may be measured in 900 mL of 0.1 N HCl using a USP type II paddle apparatus and at a paddle speed of either about 100 rpm or 150 rpm and a constant temperature of 37° C.

In one embodiment, the at least one immediate release portion of the composition may have in vitro release rates of hydrocodone and acetaminophen as follows: more than about 90% of the hydrocodone and/or the acetaminophen present in the at least one immediate release portion is released in about 15 minutes, or essentially 100% of the hydrocodone and/or the acetaminophen present in the at least one immediate release portion may be released within about 15 minutes. In another embodiment, more than about 90% of the hydrocodone and/or the acetaminophen present in the at least one immediate release portion may be released within about 5 min. In yet another embodiment, essentially 100% of the hydrocodone and/or the acetaminophen present in the at least one immediate release portion may be released within about 5 min.

In one embodiment, the at least one extended release portion of the composition may have in vitro release rate of hydrocodone as follows: from about 1% to about 20% of the hydrocodone present in the at least one extended release portion may be released within about 15 min, from about 30% to about 50% of the hydrocodone present in the at least one extended release portion is released within about 2 hours, from about 50% to about 75% of the hydrocodone present in the at least one extended release portion is released in about 4 hours, at least about 80% of the hydrocodone present in the at least one extended release portion is released within about 8 hours, and at least about 90% of the hydrocodone present in the at least one extended release portion is released within about 12 hours.

In yet another embodiment, the at least one extended release portion may have in vitro release rates of hydrocodone as follows: from about 1% to about 20% of the hydrocodone present in the extended release portion may be released within about 15 min, from about 30% to about 50% of the hydrocodone present in the extended release portion may be released within about 2 hours, from about 50% to about 75% of the hydrocodone present in the extended release portion may be released within about 4 hours, and from about 80% to about 100% of the hydrocodone present in the extended release portion may be released within about 8 hours.

In one embodiment, the in vitro release rates of hydrocodone from the composition may be as follows: about 20% to about 50% of hydrocodone may be released from the composition within about 15 minutes, from about 25% to about 55% of hydrocodone may be released from the composition within about 30 minutes, from about 35% to about 65% of hydrocodone may be released within about 1 hour, from about 40% to about 80% of hydrocodone may be released from the composition in about 2 hours, from about 60% to about 100% of hydrocodone may be released from the composition within about 4 hours, from about 70% to about 100% of hydrocodone may be released from the composition within about 6 hours, from about 80% to about 100% of hydrocodone may be released from the composition within about 8 hours, from about 90% to about 100% of hydrocodone may be released from the composition within about 12 hours, and from about 90% to about 100% of hydrocodone may be released from the composition within about 18 hours.

In another embodiment, the in vitro release rates of hydrocodone from the composition may be as follows: about 20% to about 40% of hydrocodone may be released from the composition within about 15 minutes, from about 25% to about 45% of hydrocodone may be released from the composition within about 30 minutes, from about 35% to about 55% of hydrocodone may be released within about 1 hour, from about 45% to about 65% of hydrocodone may be released from the composition in about 2 hours, from about 60% to about 85% of hydrocodone may be released from the composition within about 4 hours, from about 70% to about 100% of hydrocodone may be released from the composition within about 6 hours, from about 80% to about 100% of hydrocodone may be released from the composition within about 8 hours, from about 85% to about 100% of hydrocodone may be released from the composition within about 12 hours, and from about 90% to about 100% of hydrocodone may be released from the composition within about 18 hours.

In another embodiment, the in vitro release rates of hydrocodone from the composition may be as follows: about 30% to about 35% of hydrocodone may be released from the composition within about 15 minutes, from about 35% to about 40% of hydrocodone may be released from the composition within about 30 minutes, from about 40% to about 50% of hydrocodone may be released within about 1 hour, from about 50% to about 60% of hydrocodone may be released from the composition in about 2 hours, from about 65% to about 75% of hydrocodone may be released from the composition within about 4 hours, from about 80% to about 90% of hydrocodone may be released from the composition within about 6 hours, from about 90% to about 100% of hydrocodone may be released from the composition within about 8 hours, and from about 95% to about 100% of hydrocodone may be released from the composition within about 12 hours.

In one embodiment, the in vitro release rates of acetaminophen from the composition may be as follows: about 40% to about 65% of acetaminophen may be released from the composition within about 15 minutes, from about 45% to about 65% of acetaminophen may be released from the composition with about 30 minutes, from about 50% to about 70% of acetaminophen may be released from the composition within about 1 hour, from about 55% to about 80% of acetaminophen may be released from the composition within about 2 hours, from about 65% to about 95% of acetaminophen may be released from the composition within about 4 hours, from about 75% to about 100% of acetaminophen may be released from the composition within about 6 hours, from about 80% to about 100% of acetaminophen may be released from the composition within about 8 hours, from about 85% to about 100% of acetaminophen may be released from the composition within about 12 hours, and from about 90% to about 100% of acetaminophen may be released from the composition within about 18 hours.

In a further embodiment, the in vitro release rates of acetaminophen from the composition may be as follows: about 50% to about 55% of acetaminophen may be released from the composition within about 15 minutes, from about 52% to about 58% of acetaminophen may be released from the composition within about 30 minutes, from about 55% to about 60% of acetaminophen may be released from the composition within about 1 hour, from about 60% to about 65% of acetaminophen may be released from the composition within about 2 hours, from about 70% to about 75% of acetaminophen may be released from the composition within about 4 hours, from about 80% to about 85% of acetaminophen may be released from the composition within about 6 hours, from about 90% to about 95% of acetaminophen may be released from the composition with about 8 hours, and from about 95% to about 100% of acetaminophen may be released from the composition within about 12 hours.

In one embodiment, the in vitro release rates of hydrocodone and acetaminophen from the composition generally are not affected by low concentrations of ethanol (e.g., 5% v/v or 20% v/v) when measured in 900 mL of 0.1 N HCl containing the desired percentage of ethanol using a USP type II paddle apparatus and at a constant temperature of 37° C. and about 150 rpm. For example, from about 25% to about 35% of hydrocodone and about 50% to about 55% of acetaminophen may be released from the composition within about 15 minutes when measured in the presence of 5% to 20% ethanol, and from about 50% to about 65% of hydrocodone and from about 60% to about 70% of acetaminophen may be released from the composition within about 2 hours when measured in the presence of 5% to 20% ethanol.

The in vitro release rates of hydrocodone and acetaminophen from the composition generally are reduced, however, in the presence of 40% ethanol. For example, from about 5% to about 15% of the hydrocodone and from about 15% to about 30% of the acetaminophen may be released from the composition within about 15 minutes when measured in the presence of 40% ethanol, and from about 30% to about 45% of hydrocodone and from about 45% to about 55% of acetaminophen may be released from the composition within about 2 hours when measured in the presence of 40% ethanol.

Stated another way, less hydrocodone is extracted from the composition by a solution of 0.1 N HCl and 40% ethanol than is extracted by a solution of 0.1 N HCl. In some embodiments, less than about 75% of the hydrocodone that is released in the presence of 0.1 N HCl is released in the presence 0.1 N HCl containing 40% ethanol. In additional embodiments, less than about 70%, 65%, 60%, 55%, 50%, 45%, or 40% of the hydrocodone that may be released in the presence of 0.1 N HCl is released in the presence 0.1 N HCl and 40% ethanol. For example, less than about 40% of the hydrocodone that is released in the presence of 0.1N HCl within about 15 minutes may be released in the presence 0.1N HCl and 40% ethanol within about 15 minutes. In other embodiments, less than about 60% of the hydrocodone that is released in the presence of 0.1 N HCl within about 30 minutes may be released in the presence of 0.1 N HCl and 40% ethanol within about 30 minutes. In additional embodiments, less than about 75% of the hydrocodone that is released in the presence of 0.1 N HCl within about 2 hours may be released in the presence 0.1 N HCl and 40% ethanol within about 2 hours.

(f) Stability Data for the Pharmaceutical Composition

In one embodiment, p-aminophenol may be present in the pharmaceutical composition as a degradation product of acetaminophen in any amount up to and including, but no more than, about 100 ppm. In other embodiments, p-aminophenol may be present in the pharmaceutical composition as a degradation product of acetaminophen in an amount of about 0.2 ppm to about 6.0 ppm after storage for about 1, 2, or 3 months at a temperature of about 25° C. to about 40° C. and at about 60% to about 75% relative humidity. In yet another embodiment, p-aminophenol may be present in the pharmaceutical composition as a degradation product of acetaminophen in an amount of about 0.6 ppm to about 6.0 ppm after storage for about 1, 2, or 3 months at a temperature of about 25° C. to about 40° C. and at about 60% to about 75% relative humidity. In still another embodiment, p-aminophenol may be present in the pharmaceutical composition as a degradation product of acetaminophen in an amount of about 0.2 ppm, 0.3 ppm, 0.4 ppm, 0.5 ppm, 0.6 ppm, 0.7 ppm, 0.8 ppm, 0.9 ppm, 1.0 ppm, 1.1 ppm, 1.2 ppm, 1.3 ppm, 1.4 ppm, 1.5 ppm, 1.6 ppm, 1.7 ppm, 1.8 ppm, 1.9 ppm, 2.0 ppm, 2.1 ppm, 2.2 ppm, 2.3 ppm, 2.4 ppm, 2.5 ppm, 2.6 ppm, 2.7 ppm, 2.8 ppm, 2.9 ppm, 3.0 ppm, 3.1 ppm, 3.2 ppm, 3.3 ppm, 3.4 ppm, 3.5 ppm, 3.6 ppm, 3.7 ppm, 3.8 ppm, 3.9 ppm, 4.0 ppm, 4.1 ppm, 4.2 ppm, 4.3 ppm, 4.4 ppm, 4.5 ppm, 4.6 ppm, 4.7 ppm, 4.8 ppm, 4.9 ppm, 5.0 ppm, 5.1 ppm, 5.2 ppm, 5.3 ppm, 5.4 ppm, 5.5 ppm, 5.6 ppm, 5.7 ppm, 5.8 ppm, 5.9 ppm, and 6.0 ppm after storage for about 1, 2, or 3 months at a temperature of 25° C. to about 40° C. and at about 60% to about 75% relative humidity In one embodiment, each unspecified acetaminophen degradation product may be present in the pharmaceutical composition in any amount up to about 0.15% by weight of the acetaminophen. In another embodiment, each unspecified acetaminophen degradation product may be present in the pharmaceutical composition as a degradation product of acetaminophen in an amount of about 0.01% and about 0.15% by weight of the acetaminophen after storage for about 1, 2, or 3 months at a temperature of about 25° C. to about 40° C. and at about 60% to about 75% relative humidity. In still another embodiment, each unspecified acetaminophen degradation product may be present in the pharmaceutical composition as a degradation product of acetaminophen in an amount of about 0.05% and about 0.15% by weight of the acetaminophen after storage for about 1, 2, or 3 months at a temperature of about 25° C. to about 40° C. and at about 60% to about 75% relative humidity. In other embodiments, each unspecified acetaminophen degradation product may be present in the pharmaceutical composition as a degradation product of acetaminophen in an amount of about 0.01%, 0.02%, 0.03%, 0.04%, 0.05%, 0.06%, 0.07%, 0.08%, 0.09%, 0.1%, 0.11%, 0.12%, 0.13%, 0.14%, and 0.15% by weight of the acetaminophen after storage for about 1, 2, or 3 months at a temperature of about 25° C. to about 40° C. and at about 60% to about 75% relative humidity.

In one embodiment, the total acetaminophen degradation products may be present in the pharmaceutical composition in a maximum amount of about 1.0% by weight of the acetaminophen. In other embodiments, the total acetaminophen degradation products may be present in the pharmaceutical composition in an amount of about 0.05% to about 1.0% by weight of the acetaminophen after storage for about 1, 2, or 3 months at a temperature of about 25° C. to about 40° C. and at about 60% to about 75% relative humidity. In further embodiments, the total acetaminophen degradation products may be present in the pharmaceutical composition in an amount of about 0.05%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, and 1.0% by weight of the acetaminophen after storage for about 1, 2, or 3 months at a temperature of about 25° C. to about 40° C. and at about 60% to about 75% relative humidity.

In one embodiment, the total hydrocodone degradation products may be present in the pharmaceutical composition in a maximum amount of about 1.0% by weight of the hydrocodone. In further embodiments, the total hydrocodone degradation products may be present in the pharmaceutical composition in an amount of about 0.05% to about 1.0% by weight of the hydrocodone after storage for about 1, 2, or 3 months at a temperature of about 25° C. to about 40° C. and at about 60% to about 75% relative humidity. In yet other embodiments, the total hydrocodone degradation products may be present in the pharmaceutical composition in an amount of about 0.05%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, and 1.0% by weight of the hydrocodone after storage for about 1, 2, or 3 months at a temperature of about 25° C. to about 40° C. and at about 60% to about 75% relative humidity.

(g) In vivo and Pharmacokinetic Properties of the Pharmaceutical Composition

The pharmaceutical composition disclosed herein comprises at least one immediate release portion for immediate release of hydrocodone and acetaminophen such that therapeutic plasma concentrations are quickly attained (e.g., within one hour) and the initial onset of action is achieved within about 5 minutes, 10 minutes, 15 minutes, 20 minutes, 25 minutes, 30 minutes, 35 minutes, 40 minutes, 45 minutes, 50 minutes, 55 minutes, or 60 minutes after administration of the composition upon oral administration to a subject. The pharmaceutical composition disclosed herein also comprises at least one extended release portion for sustained release of hydrocodone and acetaminophen over an extended period of time, e.g., about 3 to about 12 hours, or about 4 to about 9 hours, or at least about 6 hours, or at least about 8 hours, to the upper gastrointestinal tract where acetaminophen, and potentially hydrocodone, is best absorbed.

The pharmaceutical composition may be orally administered to a subject once in a 24 hour period (q.d. or once-daily), two times in a 24 hour period (b.i.d. or twice-daily), or three times in a 24 hour period (t.i.d. or three times daily).

In one embodiment, the pharmaceutical composition may be orally administered to the subject twice a day (i.e., every 12 hours). The subject may be a mammal, and in certain embodiments, the subject may be a human.

In another embodiment, the subject may be administered a first or loading dose of the pharmaceutical composition. This first or loading dose may assist the subject in more quickly attaining steady state blood levels of the active drugs. In a further embodiment, the subject may be administered a first or loading dose of the pharmaceutical composition comprising about 22.5 mg of hydrocodone and about 975 mg of acetaminophen. In yet another embodiment, the subject may be administered a first or loading dose of the pharmaceutical composition comprising 2 tablets, each tablet comprising about 11.25 mg of hydrocodone and about 462.5 mg of acetaminophen. In yet another embodiment, the subject may be administered a first or loading dose of the pharmaceutical composition comprising 3 tablets, each tablet comprising about 7.5 mg of hydrocodone and about 325 mg of acetaminophen. In still another embodiment, the subject may be administered a first or loading dose of the pharmaceutical composition comprising 4 tablets, each tablet comprising about 5.625 mg of hydrocodone and about 231.25 mg of acetaminophen. In yet another embodiment, the subject may be administered a first or loading dose of the pharmaceutical composition comprising 2 capsules, each capsule comprising about 11.25 mg of hydrocodone and about 462.5 mg of acetaminophen. In yet another embodiment, the subject may be administered a first or loading dose of the pharmaceutical composition comprising 3 capsules, each capsules comprising about 7.5 mg of hydrocodone and about 325 mg of acetaminophen. In still another embodiment, the subject may be administered a first or loading dose of the pharmaceutical composition comprising 4 capsules, each capsules comprising about 5.625 mg of hydrocodone and about 231.25 mg of acetaminophen.

Further, upon oral administration to a subject, the composition disclosed herein may maintain a therapeutic blood plasma concentration of hydrocodone of at least about 5 ng/mL from about 0.75 hours to about 20 hours after administration of the composition. In another embodiment, the plasma concentration of hydrocodone may be maintained at a concentration of at least about 7.5 ng/mL from about 0.5 hour to about 10 hours after administration of the composition. In yet another embodiment, the plasma concentration of hydrocodone may be maintained at a concentration of at least about 7.5 ng/mL from about 1 hour to about 12 hours after administration of the composition. In a further embodiment, the plasma concentration of hydrocodone may be maintained at a concentration of at least about 10 ng/mL from about 2 hours to about 10 hours after administration of the composition. In yet another embodiment, the plasma concentration of hydrocodone may be maintained at a concentration of at least about 10 ng/mL from about 1 hour to about 10 hours after administration of the composition. In still another embodiment, the plasma concentration of hydrocodone may be maintained at a concentration of at least about 10 ng/mL from about 0.75 hour to about 10 hours after administration of the composition.

In another embodiment, the composition, when orally administered to a subject, may produce a plasma profile characterized by a mean Cmax (peak plasma concentration) for hydrocodone from about 0.9 ng/mL/mg to about 2.0 ng/mL/mg. In another embodiment, the mean Cmax for hydrocodone may range from about 1.0 ng/mL/mg to about 1.6 ng/mL/mg. In an additional embodiment, the mean Cmax for hydrocodone may be 0.9, 1.0, 1.1, 1.2, 1.3, 1.4, 1.5, 1.6, 1.7, 1.8, 1.9, or 2.0 ng/mL/mg. Moreover, the mean Cmax for hydrocodone at steady state may range from about 1.3 ng/mL/mg to about 2.0 ng/mL/mg, from about 1.5 ng/mL/mg to about 1.95 ng/mL/mg, or from about 1.6 ng/mL/mg to about 1.85 ng/mL/mg.

In a further embodiment, the pharmaceutical composition, when orally administered to a subject, surprisingly may produce a plasma profile characterized by a biphasic absorption of hydrocodone. Deconvolution of the pharmaceutical composition and the target plasma profiles can be done in WinNonLin (version 5.2, Pharsight Corp., Mountain View, Calif.). The biphasic absorption of hydrocodone may be characterized by an initial rapid absorption resulting in a first peak in plasma concentrations between about 1 hour and 2 hours, which contributes to the early onset of action, and a second peak in plasma concentrations between about 3 hours and 7 hours as a result of slower absorption taking place from the at least one extended release portion after administration of the composition, which contributes to the duration or maintenance of analgesia. In some instances, the second peak may correspond to the overall Cmax of the composition. The biphasic absorption of hydrocodone may be characterized by a plasma concentration-time profile for hydrocodone in which the slope of a line drawn between 0 hour and 2 hour is greater than the slope of a line drawn between about 2 hours and 5 hours.

This biphasic increase in hydrocodone levels resulting from the composition has several benefits. For example, providing rapid but not too high concentrations of hydrocodone for quick onset of analgesia followed by maintenance of hydrocodone levels over an extended time period could prevent a human subject from developing liking or dependence (abuse) for hydrocodone. Further fluctuations in the hydrocodone plasma levels could also prevent development of tolerance at the active site. Thus, the biphasic increase in hydrocodone levels helps to prevent this acute tolerance.

In an additional embodiment, the pharmaceutical composition, when orally administered to a subject, may produce a plasma profile characterized by a mean AUC for hydrocodone from about 9.0 ng·hr/mL/mg to about 24.0 ng·hr/mL/mg. In a further embodiment, the mean AUC for hydrocodone may be from about 10.0 ng·hr/mL/mg to about 22.0 ng·hr/mL/mg. In another embodiment, the mean AUC for hydrocodone may be about 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, or 24.0 ng·hr/mL/mg. Additionally, the mean AUC for hydrocodone at steady state may range from about 10.0 ng·hr/mL/mg to about 20.0 ng·hr/mL/mg, from about 12.0 ng·hr/mL/mg to about 19.0 ng·hr/mL/mg, or from about 13.0 ng·hr/mL/mg to about 18.0 ng·hr/mL/mg.

In a further embodiment, the pharmaceutical composition, when orally administered to a subject, may produce a plasma profile characterized by a median Tmax (time to peak plasma concentration) for hydrocodone from about 2.0 hours to about 8.0 hours. In an alternate embodiment, the median Tmax for hydrocodone may be from about 3.0 hours to about 6.0 hours. In another embodiment, the median Tmax for hydrocodone may be about 2.0, 2.5, 3.0, 3.5, 4.0, 4.5, 5.0, 5.5, 6.0, 6.5, 7.0, 7.5, or 8.0 hours. Moreover, the median Tmax for hydrocodone at steady state may range from about 1.5 hours to about 5.0 hours, or from about 2 hours to about 4 hours.

In still another embodiment, the pharmaceutical composition, when orally administered to a subject, may produce a plasma profile characterized by a median $t_{lag}$ for hydrocodone from about 0 hours to about 0.5 hours. In an alternate embodiment, the median tlag for hydrocodone may be from about 0 hours to about 0.33 hours.

Rates of absorption are often assessed by comparing standard pharmacokinetic parameters such as Tmax and Cmax. The extent of absorption is assessed by the AUC. A short Tmax has been used to indicate rapid absorption. The U.S. FDA, *Guidance for Industry: Bioavailability and Bioequivalence Studies for Orally Administered Drug Products—General Considerations* (March 2003) and related publications (Chen et al, Clin. Pharmacokinet. 40(8):565-72, 2001) also recommends the use of partial AUC for some modified-release drugs ("MR drugs"), such as the pharmaceutical compositions disclosed herein. A partial AUC calculation may be used to measure early exposure to a drug, which may signify an initial onset of pain relief and/or to measure prolonged exposure of a drug in achieving sustained relief. Partial AUC calculations can also demonstrate whether two MR drugs are truly bioequivalent by comparing, for example, an early partial AUC, which will be associated with a drug's response onset, and a late partial AUC, which will be associated with a drug's sustained response. The parameters for compositions vary greatly between subjects. The parameters also vary depending on aspects of the study protocol such as the sampling scheduling, subject posture and general subject health. Values quoted in this specification are given as mean±standard deviation unless otherwise noted.

For partial AUC calculations, the standard linear trapezoidal summation over each time interval is used. The partial AUCs are calculated from the mean pharmacokinetic profile. For time 0 to 1 hour the partial AUC is $AUC_{(0-1hr)}$; for time 0 to 2 hours the partial AUC is $AUC_{(0-2hr)}$; for time 0-4 hours the partial AUC is $AUC_{(0-4hr)}$; for time 0 to 6 hour the partial AUC is $AUC_{(0-6hr)}$; for time 0 to 8 hours the partial AUC is $AUC_{(0-8hr)}$; and for time 0 to the last measurable time point ("x") the partial AUC is $AUC_{(0-(x)hr)}$ where each partial AUC is calculated according to standard pharmaceutical industry pharmacokinetic calculation methodologies as given by:

$AUC_{(0-1hr)}$—Area under the drug concentration-time curve calculated using linear trapezoidal summation from time zero to time 1 hour.

$AUC_{(0-2hr)}$—Area under the drug concentration-time curve calculated using linear trapezoidal summation from time zero to time 2 hours.

$AUC_{(0-4hr)}$—Area under the drug concentration-time curve calculated using linear trapezoidal summation from time zero to time 4 hours.

$AUC_{(0-6hr)}$—Area under the drug concentration-time curve calculated using linear trapezoidal summation from time zero to time 6 hours.

$AUC_{(0-8hr)}$—Area under the drug concentration-time curve calculated using linear trapezoidal summation from time zero to time 8 hours.

$AUC_{(0-(t)hr)}$—Area under the drug concentration-time curve calculated using linear trapezoidal summation from time zero to the last measurable time point.

$AUC_{(0-(Tmax\ of\ IR\ product+2SD))}$—Area under the drug concentration-time curve calculated using linear trapezoidal summation from time zero to the time of the mean peak (Tmax) for the immediate release version of the drug plus two standard deviations ("2SD") for the immediate release drug. The FDA has identified this calculation in association with an early onset of response for certain modified-release dosage forms, which show complex pharmacokinetic characteristics. (See supra March 2003 Guidance; Draft Guidance on Dexmethylphenidate Hydrochloride (March 2012); Draft Guidance on Methylphenidate Hydrocholoride (November 2011)).

$AUC_{((Tmax\ of\ IR\ product+2SD)-t)}$—Area under the drug concentration-time curve calculated using linear trapezoidal summation from the time of the mean peak (Tmax) for the immediate release version of the drug plus two standard deviations ("2SD") for the immediate release drug to the last measurable time point. The FDA has identified this parameter in association with sustaining the response for modified-release dosage forms, which shows complex pharmacokinetic characteristics. (See March 2003 Guidance supra; Draft Guidance on Dexmethylphenidate Hydrochloride (March 2012); Draft Guidance on Methylphenidate Hydrocholoride (November 2011)).

$AUC_{(x-(y)hr)}$—Area under the drug concentration-time curve calculated using linear trapezoidal summation from time "x" (e.g., any measurable time point, such as 8 hours) to time "y" (e.g., any other measurable time point later than "x", such as 12 hours).

$AUC_{(0-\infty)}$—Area under the drug concentration-time curve calculated using linear trapezoidal summation from time 0 to infinity.

Further, partial AUC may be calculated using trapezoidal summation from time Tmax to time t (the last measured time point of plasma concentration profile).

In one embodiment, the pharmaceutical composition, when orally administered to a subject, may produce a plasma profile characterized by an $AUC_{(0-(Tmax\ of\ IR\ product+2SD))}$ for hydrocodone after a single dose from about 1.0 ng·hr/mL/mg to about 5.0 ng·hr/mL/mg, from about 1.50 ng·hr/mL/mg to about 4.25 ng·hr/mL/mg, or from about 2.0 ng·hr/mL/mg to about 3.0 ng·hr/mL/mg. In another embodiment, the $AUC_{0-(Tmax+2SD\ of\ IR\ product)}$ for hydrocodone may be about 1.0, 1.25, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, or 3.5 ng·hr/mL/mg.

In one embodiment, the pharmaceutical composition, when orally administered to a subject, may produce a plasma profile characterized by an $AUC_{(0-3hr)}$ for hydrocodone after a single dose from about 1.0 ng·hr/mL/mg to about 5.0 ng·hr/mL/mg, from about 1.50 ng·hr/mL/mg to about 4.25 ng·hr/mL/mg, or from about 2.0 ng·hr/mL/mg to about 3.0 ng·hr/mL/mg. In another embodiment, the $AUC_{(0-3hr)}$ for hydrocodone may be about 1.0, 1.25, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, or 3.5 ng·hr/mL/mg.

In another embodiment, the pharmaceutical composition, when orally administered to a subject, may produce a plasma profile characterized by an $AUC_{(0-2.44hr)}$ for hydrocodone after a single dose from about 0.5 ng·hr/mL/mg to about 5.0 ng·hr/mL/mg, from about 1.0 ng·hr/mL/mg to about 4.25 ng·hr/mL/mg, or from about 1.5 ng·hr/mL/mg to about 3.0 ng·hr/mL/mg. In another embodiment, the $AUC_{(0-2.44hr)}$ for hydrocodone may be about 0.5, 0.55, 0.6, 0.65, 0.7, 0.75, 0.8, 0.85, 0.9, 0.95, 1.0, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, or 3.5 ng·hr/mL/mg.

In one embodiment, the pharmaceutical composition, when orally administered to a subject, may produce a plasma profile characterized by an $AUC_{0-12hr}$ for hydrocodone from about 5 ng·hr/mL/mg to about 25 ng·hr/mL/mg, from about 7.5 ng·hr/mL/mg to about 15.5 ng·hr/mL/mg, or from about 8.5 ng·hr/mL/mg to about 12.5 ng·hr/mL/mg. In other embodiments, the pharmaceutical composition, when orally administered to a subject, may produce a plasma profile characterized by an $AUC_{0-12hr}$ for hydrocodone from about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, or 20.0 ng·hr/mL/mg.

In one embodiment, the pharmaceutical composition, when orally administered to a subject, may produce a plasma profile characterized by an $AUC_{1-12hr}$ for hydrocodone from about 3 ng·hr/mL/mg to about 20 ng·hr/mL/mg, from about 7.5 ng·hr/mL/mg to about 15.0 ng·hr/mL/mg, or from about 8 ng·hr/mL/mg to about 12.5 ng·hr/mL/mg. In other embodiments, the pharmaceutical composition, when orally administered to a subject, may produce a plasma profile characterized by an $AUC_{1-12hr}$ for hydrocodone from about 3.0, 4.0, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, or 20.0 ng·hr/mL/mg.

In one embodiment, the pharmaceutical composition, when orally administered to a subject, may produce a plasma profile characterized by an $AUC_{12-36hr}$ for hydrocodone from about 2 ng·hr/mL/mg to about 10 ng·hr/mL/mg, from about 4 ng·hr/mL/mg to about 8 ng·hr/mL/mg, and from about 6 ng·hr/mL/mg to about 7 ng·hr/mL/mg. In other embodiments, the pharmaceutical composition, when orally administered to a subject, may produce a plasma profile characterized by an $AUC_{12-36hr}$ for hydrocodone from about 2.0, 2.5, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0 ng·hr/mL/mg.

In one embodiment, the pharmaceutical composition, when orally administered to a subject, may produce a plasma profile characterized by an $AUC_{8-12hr}$ for hydrocodone from about 1 ng·hr/mL/mg to about 6 ng·hr/mL/mg, from about 2 ng·hr/mL/mg to about 5 ng·hr/mL/mg, or from about 3 ng·hr/mL/mg to about 4 ng·hr/mL/mg. In other embodiments, the pharmaceutical composition, when orally administered to a subject, may produce a plasma profile characterized by an $AUC_{8-12hr}$ for hydrocodone from about 1.25, 1.3, 1.35, 1.4, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4.0, 4.05, 4.1, 4.15, 4.2, 4.25, 4.3, 4.35, 4.4, 4.45, 4.5, 4.55, 4.6, 4.65, 4.7, 4.75, 4.8, 4.85, 4.9, 4.95, 5.0, 5.05, 5.1, 5.15, 5.2, 5.25, 5.3, 5.35, 5.4, 5.45, 5.5, 5.55, 5.6, 5.65, 5.7, or 5.75 ng·hr/mL/mg.

In one embodiment, the pharmaceutical composition, when orally administered to a subject, may produce a plasma profile characterized by an $AUC_{Tmax+2SD-36hr}$ for hydrocodone from about 5 ng·hr/mL/mg to about 25 ng·hr/mL/mg, from about 10 ng·hr/mL/mg to about 20 ng·hr/mL/mg, or from about 13 ng·hr/mL/mg to about 17 ng·hr/mL/mg. In other embodiments, the pharmaceutical composition, when orally administered to a subject, may produce a plasma profile characterized by an $AUC_{3-36hr}$ for hydrocodone from about 5.0, 5.25, 5.50, 5.75, 6.0, 6.25, 6.5, 6.75, 7.0, 7.25, 7.5, 7.75, 8.0, 8.25, 8.5, 8.75, 9.0, 9.25, 9.5, 9.75, 10.0, 10.25, 10.5, 10.75, 11.0, 11.25, 11.5, 11.75, 12.0, 12.25, 12.5, 12.75, 13.0, 13.25, 13.5, 13.75, 14.0, 14.25, 14.5, 14.75, 15.0, 15.25, 15.5, 15.75, 16.0, 16.25, 16.50, 16.75, 17.0, 17.25, 17.5, 17.75, 18.0, 18.25, 18.5, 18.75, 19.0, 19.25, 19.5, 19.75, 20.0, 20.25, 20.5, 20.75, 21.0, 21.25, 21.5, 21.75, 22.0, 22.25, 22.5, 22.75, 23.0, 23.25, 23.5, 23.75, 24.0, 24.25, 24.5, 24.75, or 25.0 ng·hr/mL/mg.

In one embodiment, the pharmaceutical composition, when orally administered to a subject, may produce a plasma profile characterized by an $AUC_{2.44-36hr}$ for hydrocodone from about 5 ng·hr/mL/mg to about 25 ng·hr/mL/mg, from about 10 ng·hr/mL/mg to about 20 ng·hr/mL/mg, or from about 13 ng·hr/mL/mg to about 17 ng·hr/mL/mg. In other embodiments, the pharmaceutical composition, when orally administered to a subject, may produce a plasma profile characterized by an $AUC_{2.44-36hr}$ for hydrocodone from about 5.0, 5.25, 5.50, 5.75, 6.0, 6.25, 6.5, 6.75, 7.0, 7.25, 7.5, 7.75, 8.0, 8.25, 8.5, 8.75, 9.0, 9.25, 9.5, 9.75, 10.0, 10.25, 10.5, 10.75, 11.0, 11.25, 11.5, 11.75, 12.0, 12.25, 12.5, 12.75, 13.0, 13.25, 13.5, 13.75, 14.0, 14.25, 14.5, 14.75, 15.0, 15.25, 15.5, 15.75, 16.0, 16.25, 16.50, 16.75, 17.0, 17.25, 17.5, 17.75, 18.0, 18.25, 18.5, 18.75, 19.0, 19.25, 19.5, 19.75, 20.0, 20.25, 20.5, 20.75, 21.0, 21.25, 21.5, 21.75, 22.0, 22.25, 22.5, 22.75, 23.0, 23.25, 23.5, 23.75, 24.0, 24.25, 24.5, 24.75, or 25.0 ng·hr/mL/mg.

In one embodiment, the pharmaceutical composition, when orally administered to a subject, may produce a plasma profile characterized by an $AUC_{0-12hr}$ for hydrocodone from about 50% to about 90% of the $AUC_{0-t}$, from about 55% to about 80% of the $AUC_{0-t}$, or from about 60% to about 70% of the $AUC_{0-t}$. In other embodiments, the pharmaceutical composition, when orally administered to a subject, may produce a plasma profile characterized by an $AUC_{0-12hr}$ for hydrocodone that is about 50%, about 53%, about 55%, about 58%, about 60%, about 63%, about 65%, about 68%, about 70%, about 73%, about 75%, about 78%, about 80%, about 83%, about 85%, about 88%, or about 90% of the $AUC_{0-t}$.

In one embodiment, the pharmaceutical composition, when orally administered to a subject, may produce a plasma profile characterized by an $AUC_{1-12hr}$ for hydrocodone from about 40% to about 90% of the $AUC_{0-t}$, from about 55% to about 80% of the $AUC_{0-t}$, or from about 60% to about 70% of the $AUC_{0-t}$. In other embodiments, the pharmaceutical composition, when orally administered to a subject, may produce a plasma profile characterized by an $AUC_{1-12hr}$ for hydrocodone of about 40%, about 43%, about 45%, about 48%, about 50%, about 53%, about 55%, about 58%, about 60%, about 63%, about 65%, about 68%, about 70%, about 73%, about 75%, about 78%, about 80%, about 83%, about 85%, about 88%, or about 90% of the $AUC_{0-t}$.

In one embodiment, the pharmaceutical composition, when orally administered to a subject, may produce a plasma profile characterized by an $AUC_{12-36hr}$ for hydrocodone from about 20% to about 50% of the $AUC_{0-t}$, from about 25% to about 45% of the $AUC_{0-t}$, or from about 30% to about 40% of the $AUC_{0-t}$. In other embodiments, the pharmaceutical composition, when orally administered to a subject, may produce a plasma profile characterized by an $AUC_{1-12hr}$ for hydrocodone of about 20%, about 23%, about 25%, about 28%, about 30%, about 33%, about 35%, about 38%, about 40%, about 43%, about 45%, about 48%, about 50%, or about 53% of the $AUC_{0-t}$.

In one embodiment, the pharmaceutical composition, when orally administered to a subject, may produce a plasma profile characterized by an $AUC_{8-12hr}$ for hydrocodone from about 5% to about 30% of the $AUC_{0-t}$, from about 10% to about 25% of the $AUC_{0-t}$, or from about 15% to about 20% of the $AUC_{0-t}$. In other embodiments, the pharmaceutical composition, when orally administered to a subject, may produce a plasma profile characterized by an $AUC_{1-12hr}$ for hydrocodone of about 5%, about 8%, about 10%, about 13%, about 15%, about 18%, about 20%, about 23%, about 25%, about 28%, or about 30% of the $AUC_{0-t}$.

In an alternate embodiment, the pharmaceutical composition, when orally administered to a subject, may provide a mean half-life of hydrocodone that ranges from about 3.5 hours to about 5.5 hours, or from about 4 hours to about 5 hours. In various embodiments, the mean half-life of hydrocodone may be about 3.8, 4.0, 4.2, 4.4, 4.6, 4.8, 5.0, or 5.2 hours.

In yet another embodiment, the pharmaceutical composition, when orally administered to a subject, produces a plasma profile characterized by an abuse quotient for hydrocodone from about 3 to about 5. In other embodiments, the abuse quotient for hydrocodone may be about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

Moreover, upon oral administration, the pharmaceutical composition disclosed herein may maintain a therapeutic plasma concentration of acetaminophen of at least about 2 mg/mL from about 1 hour to about 6 hours after administration. In another embodiment, the pharmaceutical composition may maintain a therapeutic plasma concentration of acetaminophen of at least about 2 mg/mL from about 0.75 hour to about 6.5 hours after administration. In yet another embodiment, the composition may maintain a plasma concentration of acetaminophen of at least about 1 mg/mL from about 0.5 hour to about 12 hours after administration.

In another embodiment, the pharmaceutical composition, when orally administered to a subject, may produce a plasma profile characterized by a mean $C_{max}$ for acetaminophen from about 4.0 ng/mL/mg to about 11.0 ng/mL/mg. In other embodiments, the mean $C_{max}$ for acetaminophen may be from about 4.0, 4.5, 5.0, 5.5, 6.0, 6.5, 7.0, 7.5, 8.0, 8.5, 9.0, 9.5, 10.0, 10.5, or 11.0 ng/mL/mg. Moreover, the mean $C_{max}$ for acetaminophen at steady state may range from about 6.0 ng/mL/mg to about 9.0 ng/mL/mg, from about 6.5 ng/mL/mg to about 8.5 ng/mL/mg, or from about 7.0 ng/mL/mg to about 8.0 ng/mL/mg.

In a further embodiment, the pharmaceutical composition, when orally administered to a subject, surprisingly may produce a blood plasma concentration profile characterized by a biphasic increase in blood plasma concentrations of acetaminophen. The biphasic absorption of acetaminophen may characterized by an initial rapid absorption resulting in first peak in plasma concentrations between about 0.5 hour and 2 hours, which contributes to the early onset on action, and a second peak in plasma concentrations between about 3 hours and 7 hours after administration of the composition, which contributes to the duration or maintenance of analgesia. In some instances, the second peak may correspond to the overall $C_{max}$ of the composition. The biphasic increase in blood plasma concentrations of acetaminophen is characterized by a plasma concentration-time profile for acetaminophen in which the slope of a line drawn between 0 hour and 2 hour is greater than the slope of a line drawn between about 2 hours and 5 hours. See FIG. 24.

This biphasic increase in acetaminophen levels resulting from the composition has several benefits. For example, the initial rapid rise in plasma levels produce quick onset of analgesia and the slower absorption provides maintenance of analgesia for an extended period of time.

In a further embodiment, the pharmaceutical composition, when orally administered to a subject, may produce a plasma profile characterized by a mean AUC for acetaminophen from about 35.0 ng·hr/mL/mg to about 80.0 ng·hr/mL/mg. In a further embodiment, the mean AUC for acetaminophen may range from about 35.0 ng·hr/mL/mg to about 60.0 ng·hr/mL/mg. In other embodiments, the mean AUC for acetaminophen may be about 35.0, 40.0, 45.0, 50.0, 55.0, 60.0, 65.0, 70.0, 75.0, or 80.0 ng·hr/mL/mg. Additionally, the mean AUC for acetaminophen at steady state may range from about 40.0 ng·hr/mL/mg to about 50.0 ng·hr/mL/mg, from about 35.0 ng·hr/mL/mg to about 45.0 ng·hr/mL/mg, or from about 37.0 ng·hr/mL/mg to about 42.0 ng·hr/mL/mg.

In yet another embodiment, the pharmaceutical composition when orally administered to a subject, may produce a plasma profile characterized by a median $T_{max}$ for acetaminophen from about 0.5 hours to about 6.0 hours. In another embodiment, the median $T_{max}$ for acetaminophen may be from about 1.0 hour to about 5.0 hours. In a further embodiment, the median $T_{max}$ for acetaminophen may range from about 0.5 hour to about 4.0 hours. In still another embodiment, the median $T_{max}$ for acetaminophen may range from about 0.75 to about 1.5 hours. In other embodiments, the median $T_{max}$ may be about 0.5, 0.6, 0.7, 0.8, 0.9, 1.0, 1.1, 1.2, 1.3, 1.4, 1.5, 1.6, 1.7 1.8, 1.9, 2.0, 2.2, 2.4, 2.6, 2.8, 3.0, 3.2, 3.4, 3.6, 3.8, 4.0, 4.2, 4.4, 4.6, 4.8, or 5.0 hours. Moreover, the median $T_{max}$ for acetaminophen at steady state may range from about 0.5 hour to about 1.0 hour, or from about 0.5 hour to about 0.75 hour.

In a further embodiment, the pharmaceutical composition, when orally administered to a subject, may produce a plasma profile characterized by a median $t_{lag}$ for acetaminophen from about 0 hour to about 0.5 hour. In an alternate embodiment, the median $t_{lag}$ for acetaminophen may be from about 0 hour to about 0.25 hour. In one embodiment, the median $t_{lag}$ for acetaminophen may be 0 hour. In another embodiment, the median $t_{lag}$ for acetaminophen may be 0.25 hour.

In one embodiment, the pharmaceutical composition, when orally administered to a subject, may produce a plasma profile characterized by various partial AUCs for acetaminophen. The partial AUCs for acetaminophen are calculated as described above for hydrocodone. The pharmaceutical composition, when orally administered to a subject, may produce a plasma profile characterized by an $AUC_{0-1hr}$ for acetaminophen from about 1.25 ng·hr/mL/mg to about 3.25 ng·hr/mL/mg, from about 1.60 ng·hr/mL/mg to about 2.0 ng·hr/mL/mg, or from about 2.0 ng·hr/mL/mg to about 2.75 ng·hr/mL/mg. In another embodiment, the $AUC_{0-1hr}$ for acetaminophen may be about 1.25, 1.30, 1.40, 1.50, 1.55, 1.60, 1.65, 1.70, 1.75, 1.80, 1.85, 1.90, 1.95, 2.0, 2.05, 2.10, 2.15, 2.20, 2.25, 2.30, 2.35, 2.40, 2.45, 2.50, 2.55, 2.60, 2.65, 2.70, 2.75, 2.80, 2.85, or 2.90 or ng·hr/mL/mg.

In an additional embodiment, the pharmaceutical composition, when orally administered to a subject, may produce a plasma profile characterized by an $AUC_{0-2hr}$ for acetaminophen from about 4.25 ng·hr/mL/mg to about 8.75 ng·hr/mL/mg, from about 5.50 ng·hr/mL/mg to about 6.0 ng·hr/mL/mg, or from about 6.0 ng·hr/mL/mg to about 7.25 ng·hr/mL/mg. In another embodiment, the $AUC_{0-2hr}$ for acetaminophen may be about 4.25, 4.5, 4.75, 5.0, 5.25, 5.5, 5.75, 6.0, 6.25, 6.5, 6.75, 7.0, 7.25, 7.50, 7.75 or 8.0 ng·hr/mL/mg.

In a further embodiment, the pharmaceutical composition, when orally administered to a subject, may produce a plasma profile characterized by an $AUC_{0-4hr}$ for acetaminophen from about 10.0 ng·hr/mL/mg to about 20.0 ng·hr/mL/mg, from about 13.0 ng·hr/mL/mg to about 14.5 ng·hr/mL/mg, or from about 14.5 ng·hr/mL/mg to about 16.5 ng·hr/mL/mg. In another embodiment, the $AUC_{0-4hr}$ for acetaminophen may be about 10.0, 11.0, 12.0, 13.0, 13.5, 14.0, 14.5, 15.0, 15.5, 16.0, 16.5, or 17.0 ng·hr/mL/mg.

In yet another embodiment, the pharmaceutical composition, when orally administered to a subject, may produce a plasma profile characterized by an $AUC_{Tmax-t}$ for acetaminophen from about 20.0 ng·hr/mL/mg to about 40.0 ng·hr/mL/mg, from about 23.5 ng·hr/mL/mg to about 36.0 ng·hr/mL/mg, or from about 29.0 ng·hr/mL/mg to about 31.0 ng·hr/mL/mg. In another embodiment, the $AUC_{Tmax-t}$ for acetaminophen may be about 20.0, 21.0, 22.0, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5 or 36.0 ng·hr/mL/mg.

In yet another embodiment, the pharmaceutical composition, when orally administered to a subject, may produce a plasma profile characterized by an $AUC_{(0-(Tmax\ of\ IR\ product+2SD))}$ for acetaminophen after a single dose from about 3.0 ng·hr/mL/mg to about 13.0 ng·hr/mL/mg, from about 4.0 ng·hr/mL/mg to about 11.6 ng·hr/mL/mg, or from about 5.0 ng·hr/mL/mg to about 10.0 ng·hr/mL/mg. In another embodiment, the $AUC_{(0-(Tmax\ of\ IR\ product+2SD))}$ for acetaminophen may be about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, or 13 ng·hr/mL/mg.

In still another embodiment, the pharmaceutical composition, when orally administered to a subject, may produce a plasma profile characterized by an $AUC_{(0-1.7)}$ for acetaminophen after a single dose from about 5.0 ng·hr/mL/mg to about 13.0 ng·hr/mL/mg, from about 7.2 ng·hr/mL/mg to about 11.6 ng·hr/mL/mg, or from about 8.5 ng·hr/mL/mg to about 10.0 ng·hr/mL/mg. In another embodiment, the $AUC_{(0-1.7)}$ for acetaminophen may be about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, or 13 ng·ng·hr/mL/mg.

In yet a further embodiment, the pharmaceutical composition, when orally administered to a subject, may produce a plasma profile characterized by an $AUC_{(17-48)}$ for acetaminophen after a single dose from about 25.0 ng·hr/mL/mg to about 75.0 ng·hr/mL/mg, from about 31.5 ng·hr/mL/mg to about 55.0 ng·hr/mL/mg, or from about 35.0 ng·hr/mL/mg to about 50.0 ng·hr/mL/mg. In another embodiment, the $AUC_{(17-48)}$ for acetaminophen may be about 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, or 55.0 ng·hr/mL/mg.

In another embodiment, the pharmaceutical composition, when orally administered to a subject, may produce a plasma profile characterized by an $AUC_{(0-1.27)}$ for acetaminophen after a single dose from about 3.0 ng·hr/mL/mg to about 13.0 ng·hr/mL/mg, from about 4.0 ng·hr/mL/mg to about 11.6 ng·hr/mL/mg, or from about 5.0 ng·hr/mL/mg to about 10.0 ng·hr/mL/mg. In another embodiment, the $AUC_{(0-1.27)}$ for acetaminophen may be about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, or 13 ng·hr/mL/mg.

In still a further embodiment, the pharmaceutical composition, when orally administered to a subject, may produce a plasma profile characterized by an $AUC_{(1.27-36)}$ for acetaminophen after a single dose from about 20.0 ng·hr/mL/mg to about 75.0 ng·hr/mL/mg, from about 25.0 ng·hr/mL/mg to about 65.0 ng·hr/mL/mg, or from about 30.0 ng·hr/mL/mg to about 50.0 ng·hr/mL/mg. In another embodiment, the $AUC_{(1.27-36)}$ for acetaminophen may be about 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.0, 57.5, 58.0, 58.5, 59.0, 59.5, 60.0, 60.5, 61.0, 61.5, 62.0, 62.5, 63.0, 63.5, 64.0, 64.5, 65.0, 65.5, 66.0, 66.5, 67.0, 67.5, 68.0, 68.5, 69.0, 69.5, 70.0, 70.5, 71.0, 71.5, 72.0, 72.5, 73.0, 73.5, 74.0, 74.5, or 75.0 ng·hr/mL/mg.

In one embodiment, the pharmaceutical composition, when orally administered to a subject, may produce a plasma profile characterized by an $AUC_{0-12hr}$ for acetaminophen from about 20.0 ng·hr/mL/mg to about 60.0 ng·hr/mL/mg, from about 30 ng·hr/mL/mg to about 50 ng·hr/mL/mg, from about 35 to about 45 ng·hr/mL/mg, or from about 37.5 ng·hr/mL/mg to about 42.5 ng·hr/mL/mg. In another embodiment, the pharmaceutical composition, when orally administered to a subject, may produce a plasma profile characterized by an $AUC_{0-12hr}$ for acetaminophen from about 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, or 55.0. In a further embodiment, at $AUC_{0-12hr}$ between about 70%-95%, about 75%-92%, or about 77%-90% of the acetaminophen has been cleared. In still another embodiment, about 80% of the acetaminophen has been cleared.

In another embodiment, the pharmaceutical composition, when orally administered to a subject, may produce a plasma profile characterized by an $AUC_{1-12hr}$ for acetaminophen from about 15.0 ng·hr/mL/mg to about 55.0 ng·hr/mL/mg, from about 25.0 ng·hr/mL/mg to about 45.0 ng·hr/mL/mg, or from about 30.0 to about 40.0 ng·hr/mL/mg. In another embodiment, the pharmaceutical composition, when orally administered to a subject, may produce a plasma profile characterized by an $AUC_{1-12hr}$ for acetaminophen from about 15, 16, 17, 18, 19, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, or 50.0 ng·hr/mL/mg.

In yet another embodiment, the pharmaceutical composition, when orally administered to a subject, may produce a plasma profile characterized by an $AUC_{12-36hr}$ for acetaminophen from about 5.0 ng·hr/mL/mg to about 25.0 ng·hr/mL/mg, from about 7.5 ng·hr/mL/mg to about 20.0 ng·hr/mL/mg, or from about 10.0 ng·hr/mL/mg to about 15.0. In other embodiments, the pharmaceutical composition, when orally administered to a subject, may produce a plasma profile characterized by an $AUC_{12-36hr}$ for acetaminophen from about 5.0, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, or 15.0 ng·hr/mL/mg.

In another embodiment, the pharmaceutical composition, when orally administered to a subject, may produce a plasma profile characterized by an $AUC_{8-12hr}$ for acetaminophen from about 1.5 ng·hr/mL/mg to about 15.5 ng·hr/mL/mg, from about 2 ng·hr/mL/mg to about 12.25 ng·hr/mL/mg, from about 3.5 ng·hr/mL/mg to about 10 ng·hr/mL/mg, or from about 4.5 ng·hr/mL/mg to about 6.5 ng·hr/mL/mg. In other embodiments, the pharmaceutical composition, when orally administered to a subject, may produce a plasma profile characterized by an $AUC_{8-12hr}$ for acetaminophen from about 1.5, 1.75, 2.0, 2.25, 2.5, 2.75, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0 ng·hr/mL/mg.

In one embodiment, the pharmaceutical composition, when orally administered to a subject, may produce a plasma profile characterized by an $AUC_{(0-3hr)}$ for acetaminophen from about 5 ng·hr/mL/mg to about 30 ng·hr/mL/mg, from about 10 ng·hr/mL/mg to about 20 ng·hr/mL/mg, or from about 13 ng·hr/mL/mg to about 17 ng·hr/mL/mg. In other embodiments, the pharmaceutical composition, when orally administered to a subject, may produce a plasma profile characterized by an $AUC_{(0-3hr)}$ for acetaminophen from about 5.0, 6.0, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, or 20.0 ng·hr/mL/mg.

In another embodiment, the pharmaceutical composition, when orally administered to a subject, may produce a plasma profile characterized by an $AUC_{(3-36hr)}$ for acetaminophen from about 20 ng·hr/mL/mg to about 50 ng·hr/mL/mg, from about 20 ng·hr/mL/mg to about 40 ng·hr/mL/mg, or from about 25 ng·hr/mL/mg to about 35 ng·hr/mL/mg. In other embodiments, the pharmaceutical composition, when orally administered to a subject, may produce a plasma profile characterized by an $AUC_{(3-36hr)}$ for acetaminophen from about 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, or 50 ng·hr/mL/mg.

In one embodiment, the pharmaceutical composition, when orally administered to a subject, may produce a plasma profile characterized by an $AUC_{0-12hr}$ for acetaminophen from about 50% to about 90% of the $AUC_{0-t}$, from about 55% to about 85% of the $AUC_{0-t}$, or from about 75% to about 85% of the $AUC_{0-t}$. In other embodiments, the pharmaceutical composition, when orally administered to a subject, may produce a plasma profile characterized by an $AUC_{0-12hr}$ for acetaminophen that is about 50%, 55%, 60%, 65%, 70%, 75%, 76%, 77%, 78%, 79%, 80%, 81%, 82%, 83%, 84% or 85% of the $AUC_{0-t}$.

In one embodiment, the pharmaceutical composition, when orally administered to a subject, may produce a plasma profile characterized by an $AUC_{1-12hr}$ for acetaminophen from about 40% to about 90% of the $AUC_{0-t}$, from about 55% to about 85% of the $AUC_{0-t}$, or from about 60% to about 75% of the $AUC_{0-t}$. In other embodiments, the pharmaceutical composition, when orally administered to a subject, may produce a plasma profile characterized by an $AUC_{1-12hr}$ for acetaminophen of about 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, or 80% of the $AUC_{0-t}$.

In one embodiment, the pharmaceutical composition, when orally administered to a subject, may produce a plasma profile characterized by an $AUC_{12-36hr}$ for acetaminophen from about 10% to about 40% of the $AUC_{0-t}$, from about 15% to about 35% of the $AUC_{0-t}$, or from about 20% to about 30% of the $AUC_{0-t}$. In other embodiments, the pharmaceutical composition, when orally administered to a subject, may produce a plasma profile characterized by an $AUC_{12-36hr}$ for acetaminophen of about 10%, 12%, 14%, 16%, 18%, 20%, 21%, 22%, 23%, 24%, 25%, 26%, 27%, 28%, 29%, or 30% of the $AUC_{0-t}$.

In one embodiment, the pharmaceutical composition, when orally administered to a subject, may produce a plasma profile characterized by an $AUC_{8-12hr}$ for acetaminophen from about 5% to about 30% of the $AUC_{0-t}$, from about 7% to about 25% of the $AUC_{0-t}$, or from about 10% to about 20% of the $AUC_{0-t}$. In other embodiments, the pharmaceutical composition, when orally administered to a subject, may produce a plasma profile characterized by an $AUC_{8-12hr}$ for acetaminophen of about 5%, 6%, 7%, 8%, 9%, 10%, 11%, 12%, 13%, 14%, 15%, 16%, 17%, 18%, 19%, 20%, 21%, 22%, 23%, 24%, or 25% of the $AUC_{0-t}$.

In an alternate embodiment, the pharmaceutical composition, when orally administered to a subject, may have a mean half-life of acetaminophen that ranges from about 2 hours to about 10 hours, or from about 3 hours to about 6 hours. In another embodiment, the pharmaceutical composition, when orally administered to a subject, may have a mean half-life of acetaminophen that ranges from about 3 hours to about 5 hours. In still another embodiment, the pharmaceutical composition, when orally administered to a subject, may have a mean half-life of acetaminophen that ranges from about 4 hours to about 5 hours. In various embodiments, the mean half-life of acetaminophen may be about 2.5, 3.0, 3.5, 4.0, 4.5, 5.0, 5.5, 6.0, 6.5, 6.0, 7.0, 7.5, or 8 hours. In additional embodiments, the pharmaceutical composition, when orally administered to a subject, has a mean observed half-life of acetaminophen that is more than the mean half-life of commercially available immediate release acetaminophen products.

In another embodiment, upon administration of the pharmaceutical composition to a subject, the composition may provide at least about 4 hours to about 12 hours of drug delivery to the upper gastrointestinal tract, which includes the duodenum, jejunum, and ileum of the small intestine. In another embodiment, the composition may provide at least about 6 hours of drug delivery to the upper gastrointestinal tract. In yet a further embodiment, the composition may provide at least about 8 hours of drug delivery to the upper gastrointestinal tract. In yet a further embodiment, the composition may provide at least about 9 hours, or at least about 10 hours of drug delivery to the upper gastrointestinal tract.

In yet another embodiment, upon administration of the pharmaceutical composition to a subject, APAP undergoes presystemic metabolism in the gut and/or liver allowing only a fraction of the drug to reach the systemic circulation. The fraction of drug that is originally absorbed prior to presystemic metabolism is referred to as the fraction absorbed and denoted "Fab." This is different from the fraction bioavailable "F," which is the fraction that reaches the systemic circulation after the metabolism in the gut and liver.

In another embodiment, 60-90% of the acetaminophen in the pharmaceutical composition, which is available for absorption into the systemic circulation, is absorbed in the upper gastrointestinal tract. In still another embodiment, 60-85% of acetaminophen in the pharmaceutical composition, which is available for absorption into the systemic circulation, is absorbed in the duodenum and jejunum. Greater than 50% absorption of acetaminophen in the upper gastrointestinal tract is beneficial to a human subject because acetaminophen is poorly absorbed in the stomach and well absorbed in the small intestine and particularly, the upper segment of the gastrointestinal tract. It is therefore critical that acetaminophen is available in upper small intestine for its absorption. In one embodiment acetaminophen is released in stomach and reaches quickly into upper part of the small intestine for the absorption to take place.

In another embodiment, when about 60% to about 75% of the acetaminophen is released from the dosage form in the stomach within 2 hours following oral administration, about 10% to about 25% of the total amount of the acetaminophen in the dosage form, which is available for absorption into the systemic circulation, is absorbed in the duodenum, about 25% to about 40% is absorbed in the proximal jejunum, about 15% to about 20% is absorbed in the distal jejunum, and about 5% to about 15% is absorbed in the ileum.

In another embodiment, when about 70% to about 90% of the acetaminophen is released from the dosage form in the stomach within 4 hours following oral administration, about 10% to about 25% of the total amount of the acetaminophen in the dosage form, which is available for absorption into the systemic circulation, is absorbed in the duodenum, about 25% to about 40% is absorbed in the proximal jejunum, about 15% to about 20% is absorbed in the distal jejunum, and about 5% to about 15% is absorbed in the ileum.

In yet another embodiment, when at least about 55% of the total amount of the acetaminophen is released from the dosage form in the stomach within 1 hour after oral administration and when at least about 60% of the acetaminophen is released in the stomach after 2 hours, about 15% to about 20% of the total amount of the acetaminophen in the dosage form, which is available for absorption into the systemic circulation, is absorbed in the duodenum, about 30% to about 37% is absorbed in the proximal jejunum, about 15% to about 18% is absorbed in the distal jejunum, and about 8% to about 10% is absorbed in the ileum.

In still another embodiment, upon administration of the pharmaceutical composition to a subject, the hydrocodone undergoes presystemic metabolism in the gut and/or liver allowing only a fraction of the drug to reach the systemic circulation. The fraction of drug that is originally absorbed prior to pre-systemic metabolism is referred to as the fraction absorbed and denoted "Fab." This is different from the fraction bioavailable "F," which is the fraction that reaches the systemic circulation after metabolism in the gut and liver.

In a further embodiment, 70-95% of the hydrocodone in the pharmaceutical composition, which is available for absorption into the systemic circulation, is absorbed in the upper gastrointestinal tract. In still another embodiment, 80-95% of hydrocodone in the pharmaceutical composition, which is available for absorption into the systemic circulation, is absorbed in the duodenum and jejunum.

In one embodiment, about 25% to about 50% of hydrocodone is released from the dosage form in the stomach within 1 hour following oral administration, about 10% to about 45% of the total amount of the hydrocodone in the dosage form, which is available for absorption into the systemic circulation, is absorbed in the duodenum, about 25% to about 50% is absorbed in the proximal jejunum, about 7% to about 20% is absorbed in the distal jejunum, and about 2% to about 15% is absorbed in the ileum.

In another embodiment, when about 45% to about 65% of hydrocodone is released from the dosage form in the stomach within 2 hours following oral administration, about 10% to about 50% of the total amount of the hydrocodone in the dosage form, which is available for absorption into the systemic circulation, is absorbed in the duodenum, about 25% to about 55% is absorbed in the proximal jejunum, about 5% to about 25% is absorbed in the distal jejunum, and about 2% to about 15% is absorbed in the ileum.

In another embodiment, when about 60% to about 85% of hydrocodone is released from the dosage form in the stomach within 4 hours following oral administration, about 10% to about 55% of the total amount of the hydrocodone in the dosage form, which is available for absorption into the systemic circulation, is absorbed in the duodenum, about 30% to about 60% is absorbed in the proximal jejunum, about 10% to about 30% is absorbed in the distal jejunum, and about 2% to about 20% is absorbed in the ileum.

In yet another embodiment, when at least 25% of the total amount of the hydrocodone is released from the dosage form in the stomach within 1 hour after oral administration and when at least 45% of the hydrocodone is released in the stomach after 2 hours, about 30% to about 45% of the total amount of hydrocodone in the dosage form, which is available for absorption into the systemic circulation, is absorbed in the duodenum, about 37% to about 43% is absorbed in the proximal jejunum, about 10% to about 15% is absorbed in the distal jejunum, and about 2% to about 8% is absorbed in the ileum.

In another embodiment, about 90% to about 100% of the IR dose of acetaminophen is released within about 15 minutes, 30 minutes, 45 minutes or 60 minutes after oral administration. In one embodiment, the dosage form provides a dissolution profile wherein about 20% to about 65%, about 35% to about 55% or about 40% to about 50% of the ER dose of acetaminophen remains in the ER layer between about 1 and 2 hours after administration. In one embodiment, not more than 50% of the ER dose of acetaminophen is released within about the first hour. In a further embodiment, not more than 45% or not more than 40% of the ER dose of acetaminophen is released within about the first hour. In another embodiment, not more than 85% of the ER dose of acetaminophen is released within about 4 hours. In yet another embodiment, not less than 50% is released after about 6 hours. In yet another embodiment, not less than 60% is released after about 6 hours. In one embodiment, the ER dose of acetaminophen is released over a time period of about 6 to 12, about 8 to 10, or about 9 to 10 hours in vitro. In another embodiment, the ER dose of acetaminophen is released over a time period of about 7 hours, 8 hours, 9 hours, 10 hours, 11 hours or 12 hours in vitro. In another embodiment, at least 90% or 95% of the ER dose of acetaminophen is released over a time period of about 7 hours, 8 hours, 9 hours, 10 hours, 11 hours or 12 hours in vitro.

In one embodiment, the pharmaceutical compositions disclosed herein rapidly achieve therapeutic plasma drug levels of hydrocodone and acetaminophen similar to an immediate release product, which provides an early onset of action within about the first 5 minutes, 10 minutes, 15 minutes, 20 minutes, 25 minutes, 30 minutes, 35 minutes, 40 minutes, 45 minutes, 50 minutes, 55 minutes or 60 minutes after administration of the composition, but unlike an immediate release product, the pharmaceutical composition is able to maintain those therapeutic plasma drug levels of hydrocodone and acetaminophen over an extended period of time (e.g., up to 12 hours). Currently, there is no pharmaceutical composition available comprising hydrocodone and acetaminophen which is able to provide a patient with quick onset of analgesia and maintenance of analgesia for an extended period of time.

In yet another embodiment, upon average, within one hour of administration to a subject, the pharmaceutical composition achieves a Cmax for acetaminophen. The Cmax achieved by the pharmaceutical composition disclosed herein is comparable to the Cmax obtained from a commercially-available immediate release product containing acetaminophen formulated at half the strength of the commercially-available immediate release product. The acetaminophen continues to be released from the pharmaceutical composition at a rate less than the clearance rate for the acetaminophen, so that the acetaminophen levels fall smoothly until all of the acetaminophen is absorbed. Stated another way, the acetaminophen released by the pharmaceutical composition is eliminated by the body faster than it is being absorbed. The absorption of the acetaminophen released from the pharmaceutical composition is complete in about 8 to about 10 hours so that for one half life of acetaminophen the blood supply reaching the subject's liver via the portal vein contains no additional amounts of acetaminophen beyond the amounts present in the subject's general circulation.

These additional amounts of acetaminophen delivered to the liver from the subject's portal vein are frequently caused by the absorption of acetaminophen in the subject's gastrointestinal tract. Indeed, blood from the subject's intestines passes through the liver and then on to the general circulation. When acetaminophen is undergoing absorption, blood containing acetaminophen from the absorption process passes through the subject's liver prior to entering the general circulation where the acetaminophen is diluted by the distribution and clearance processes. The metabolism of these higher acetaminophen concentrations in blood coming into the subject's liver is termed the "first pass effect." Hence, the absorption process for acetaminophen taxes a subject's metabolic systems in the liver due to these higher "first pass" concentrations. Once the absorption process is complete, the concentration of acetaminophen in the blood reaching the subject's liver through the portal vein will be the same concentration of acetaminophen as found in blood throughout the rest of the subject's body. Thus, the pharmaceutical compositions disclosed herein provide a Cmax comparable to a commercially-available immediate-release acetaminophen product (dosed at half strength) while providing a less taxing burden on the subject's metabolic systems in the liver because the acetaminophen released by the pharmaceutical composition is eliminated by the subject's body faster than it is being absorbed. This results in decreased levels of acetaminophen in a subject's liver as compared to an immediate release dosage form of acetaminophen dosed every 6 hours.

(h) Exemplary Compositions

In one embodiment, the pharmaceutical composition for extended release of hydrocodone and acetaminophen comprises at least one extended release portion comprising acetaminophen, hydrocodone or a combination thereof, and at least one extended release component; and at least one immediate release portion comprising hydrocodone, acetaminophen or combinations thereof. In yet another embodiment, the pharmaceutical composition comprises an immediate release portion comprising hydrocodone and acetaminophen and an extended release portion comprising hydrocodone, acetaminophen and an extended release component. In still yet another embodiment, the composition comprises two extended release portions, each comprising an extended release component and one of the hydrocodone or the acetaminophen, and an immediate release portion comprising the hydrocodone and the acetaminophen. In another embodiment, the composition comprises two extended release portions, each comprising an extended release component and one of hydrocodone or acetaminophen, and two immediate release portions, each comprising one of hydrocodone or acetaminophen. In one embodiment, the extended release component comprises at least one extended release polymer. In another one embodiment, the extended release polymer comprises a polyethylene oxide. The molecular weight of the polyethylene oxide may be from about 500,000 Daltons to about 10,000,000 Daltons.

In another embodiment, the pharmaceutical composition may comprise from about 5 mg to about 30 mg of hydrocodone and from about 250 mg to about 1300 mg of acetaminophen. In one exemplary embodiment, the pharmaceutical composition may comprise about 15 mg of hydrocodone and about 650 mg of acetaminophen. In another exemplary embodiment, the composition may comprise about 15 mg of hydrocodone and about 500 mg of acetaminophen. In yet another exemplary embodiment, the composition may comprise about 15 mg of hydrocodone and about 325 mg of acetaminophen. In a further embodiment, the composition may comprise about 30 mg of hydrocodone and about 500 mg of acetaminophen. In yet another exemplary embodiment, the pharmaceutical composition may comprise about 7.5 mg of hydrocodone about 325 mg of acetaminophen. In still another exemplary embodiment, the pharmaceutical composition may comprise about 10 mg of hydrocodone about 325 mg of acetaminophen. In a further exemplary embodiment, the pharmaceutical composition may comprise about 20 mg of hydrocodone about 650 mg of acetaminophen. In another exemplary embodiment, the composition may comprise about 30 mg of hydrocodone and about 650 mg of acetaminophen. In yet another exemplary embodiment, the composition may comprise about 22.5 mg of hydrocodone and about 925 mg of acetaminophen.

In a further embodiment, a single dosage form of the pharmaceutical composition disclosed herein (e.g., one tablet) will provide a subject with approximately the same therapeutic benefit and pharmacokinetic profile as either two dosage forms (e.g., two tablets) of the composition formulated at half the strength, or three dosage forms (e.g., three tablets) of the composition formulated at a third of the strength. In yet another exemplary embodiment, the pharmaceutical composition comprising 15 mg of hydrocodone and 650 mg of acetaminophen in a single dosage form (e.g., one tablet) will provide a subject with approximately the same therapeutic benefit and pharmacokinetic profile as two dosage forms of the pharmaceutical composition formulated at half the strength (e.g., each tablet comprising 7.5 mg of hydrocodone and 325 mg of acetaminophen). In still another exemplary embodiment, the pharmaceutical composition comprising 15 mg of hydrocodone and 650 mg of acetaminophen in a single dosage form (e.g., one tablet) will provide a subject with approximately the same therapeutic benefit and pharmacokinetic profile as three dosage forms of the pharmaceutical composition formulated at a third of the strength (e.g., each tablet comprising 5 mg of hydrocodone and about 216.7 mg of acetaminophen). In yet another embodiment, the pharmaceutical composition comprising 15 mg of hydrocodone and 325 mg of acetaminophen in a single dosage form (e.g., one tablet) taken together with another tablet comprising 7.5 mg of hydrocodone and 325 mg of acetaminophen in a single dosage form will provide a subject with approximately the same therapeutic benefit and pharmacokinetic profile as a single tablet comprising 22.5 mg of hydrocodone and 650 mg of acetaminophen. In still another exemplary embodiment, the pharmaceutical composition comprising 15 mg of hydrocodone and 325 mg of acetaminophen in a single dosage form (e.g., one tablet) taken together with another tablet comprising 15 mg of hydrocodone and 325 mg of acetaminophen in a single dosage form will provide a subject with approximately the same therapeutic benefit and pharmacokinetic profile as a single tablet configuration totaling 30 mg of hydrocodone and 650 mg of acetaminophen. In yet a further exemplary embodiment, a pharmaceutical composition comprising 21 mg of hydrocodone and 650 mg of acetaminophen in a single dosage form (e.g., one tablet) will provide a subject with approximately the same therapeutic benefit and pharmacokinetic profile as two dosage forms of the pharmaceutical composition formulated at half the strength (e.g., each tablet comprising 10.5 mg of hydrocodone and 325 mg of acetaminophen).). In yet another exemplary embodiment, a pharmaceutical composition comprising 22.5 mg of hydrocodone and 925 mg of acetaminophen in a single dosage form (e.g., one tablet) will provide a subject with approximately the same therapeutic benefit and pharmacokinetic profile as three dosage forms of the pharmaceutical composition formulated at a third of the strength (e.g., each tablet comprising 7.5 mg of hydrocodone and 325 mg of acetaminophen).

In yet another embodiment, the at least one extended release portion of the composition may comprise from about 40% to about 60% (w/w) of the total amount of acetaminophen in the composition and from about 70% to about 80% (w/w) of the total amount of hydrocodone in the composition, whereas the at least one immediate release portion may comprise from about 40% to about 60% (w/w) of the total amount of acetaminophen in the composition and from about 20% to about 30% (w/w) of the total amount of hydrocodone in the composition. In still another embodiment, the at least one extended release portion may comprise about 50% (w/w) of the total amount of acetaminophen in the composition and about 75% (w/w) of the total amount of hydrocodone in the composition; and the at least one immediate release portion may comprise about 50% (w/w) of total amount of acetaminophen in the composition and about 25% (w/w) of the total amount of hydrocodone in the composition.

In another embodiment, an extended release portion of the composition may comprise, by weight of such extended release portion, from about 30% to about 50% of the extended release polymer, from about 20% to about 40% of acetaminophen, and from about 0.5% to about 2% of hydrocodone; and an immediate release portion may comprise, by weight of such immediate release portion, from about 70% to about 80% acetaminophen and from about 0.5% to about 1% of hydrocodone.

In yet another embodiment, the pharmaceutical composition may comprise from about 7.5 mg to about 30 mg of hydrocodone and from about 325 mg to about 650 mg of acetaminophen, wherein the at least one immediate release portion may comprise about 25% (w/w) of the total amount of hydrocodone in the composition and about 50% (w/w) of the total amount of acetaminophen in the composition, and the at least one extended release portion may comprise about 75% (w/w) of the total amount of hydrocodone in the composition, about 50% (w/w) of the total amount of acetaminophen in the composition, and about 35% to about 45%, by weight of the at least one extended release portion, of an extended release polymer comprising a polyethylene oxide.

Other exemplary formulations are set forth in Charts 1-2 below:

CHART 1

Representative Hydrocodone/Acetaminophen Formulations.

| | Formulation No. | | | | | | | | | |
|---|---|---|---|---|---|---|---|---|---|---|
| | 1 | 2 | 3 | 4 | 5 | 6 | 7 | 8 | 9 | 10 |
| Immediate Release Layer | | | | | | | | | | |
| APAP | 185.3 | 175.0 | 180.0 | 160.4 | 200.0 | 193.4 | 118.8 | 162.5 | 139.0 | 150.0 |
| Hydrocodone bitartrate | 1.100 | 1.75 | 2.00 | 2.50 | 1.25 | 1.00 | 2.75 | 1.875 | 1.75 | 1.875 |
| Microcrystalline cellulose | 23.0 | 17.0 | 19.0 | 27.0 | 16.0 | 18.0 | 18.0 | 14.0 | 21.0 | 24.0 |
| Pregelatinized starch | 0.05 | 0.15 | 0.25 | 0.10 | 0.05 | 0.30 | 0.20 | 0.25 | 0.15 | 0.20 |
| Citric Acid Anhydrous | 0.08 | 0.08 | 0.08 | 0.11 | 0.11 | 0.14 | 0.07 | 0.13 | 0.15 | 0.17 |
| EDTA disodium salt, dihydrate | 0.087 | 0.106 | 0.075 | 0.03 | 0.050 | 0.055 | 0.033 | 0.025 | 0.045 | 0.018 |
| Hydroxypropyl cellulose | 14.1 | 17.8 | — | — | 17.3 | — | 16.7 | 16.1 | 21.5 | — |
| Hypromellose | 2.5 | — | 3.2 | — | — | — | — | — | 8.9 | 19.5 |
| Hydroxypropyl methyl cellulose | — | — | 21.7 | 18.3 | — | 19.3 | — | — | — | 3.0 |
| Croscarmellose sodium | 10.0 | 11.0 | 11.5 | 11.5 | 13.0 | 14.5 | 14.5 | 12.5 | 14.0 | 12.5 |
| Silicon dioxide | 0.97 | 0.75 | 1.14 | 1.02 | 1.10 | 1.03 | 0.88 | 1.05 | 0.93 | 2.30 |
| Magnesium stearate | 1.5 | 1.0 | 1.0 | 0.5 | 0.5 | 2.0 | 2.0 | 0.5 | 1.5 | 2.5 |
| Extended Release Layer | | | | | | | | | | |
| APAP | 185.3 | 150.0 | 145.0 | 155.2 | 125.0 | 100.5 | 146.9 | 162.5 | 207.4 | 150.0 |
| Hydrocodone bitartrate | 6.900 | 5.75 | 5.50 | 5.00 | 6.25 | 6.50 | 7.25 | 5.625 | 4.75 | 6.625 |
| Microcrystalline cellulose | 175.4 | 180.0 | 302.2 | 275.0 | 214.8 | 250.0 | 245.7 | 203.6 | 288.3 | 200.5 |
| Pregelatinized starch | 0.60 | 0.60 | 0.70 | 0.70 | 0.70 | 0.75 | 0.75 | 0.75 | 0.85 | 0.85 |
| Citric Acid Anhydrous | 0.24 | 0.16 | 0.24 | 0.22 | 0.33 | 0.28 | 0.07 | 0.38 | 0.45 | 0.34 |
| EDTA disodium salt, dihydrate | 0.160 | 0.085 | 0.095 | 0.055 | 0.130 | 0.065 | 0.065 | 0.075 | 0.130 | 0.125 |
| Hydroxypropyl cellulose | 30.0 | 275.8 | 95.5 | 210.6 | 13.2 | 40.7 | 32.9 | 9.6 | — | — |
| Polyox N12K | 292.8 | — | — | — | 287.7 | — | — | 321.8 | 155.5 | — |
| Polyox 303 | — | — | 244.2 | — | — | — | 275.5 | — | — | 189.2 |
| Hydroxypropyl methyl cellulose | — | 103.2 | — | 134.2 | — | 182.2 | — | — | 155.5 | 210.2 |
| Silicon Dioxide | 1.8 | 1.3 | 1.5 | 2.3 | 2.4 | 3.0 | 3.5 | 3.6 | 2.0 | 2.5 |
| Magnesium Stearate | 7.5 | 8.0 | 7.4 | 8.1 | 7.5 | 10.2 | 9.9 | 7.2 | 10.3 | 10.3 |

CHART 1-continued

Representative Hydrocodone/Acetaminophen Formulations.

| | Formulation No. | | | | | | | | | |
|---|---|---|---|---|---|---|---|---|---|---|
| | 11 | 12 | 13 | 14 | 15 | 16 | 17 | 18 | 19 | 20 |
| Immediate Release Layer | | | | | | | | | | |
| APAP | 300.0 | 150.0 | 200.0 | 150.0 | 100.0 | 160.0 | 190.0 | 75.0 | 90.0 | 125.0 |
| Hydrocodone bitartrate | 2.00 | 1.00 | 1.50 | 3.50 | 2.75 | 1.25 | 1.25 | 2.50 | 1.75 | 3.00 |
| Microcrystalline cellulose | 21.5 | 18.5 | 25.3 | 35.0 | 15.7 | 27.1 | 9.9 | 13.9 | 24.2 | 16.9 |
| Pregelatinized starch | 0.03 | 0.30 | 0.25 | 0.27 | 0.08 | 0.35 | 0.75 | 0.09 | 0.15 | 0.26 |
| Citric Acid Anhydrous | 0.12 | 0.08 | 0.09 | 0.16 | 0.07 | 0.24 | 0.14 | 0.26 | 0.15 | 0.20 |
| EDTA disodium salt, dihydrate | 0.04 | 0.175 | 0.1 | 0.06 | 0.1 | 0.09 | 0.06 | 0.08 | 0.063 | 0.09 |
| Hydroxypropyl cellulose | — | 21.5 | 1.8 | 9.8 | 14.8 | — | 20.8 | 19.2 | 25.4 | — |
| Hypromellose | 2.5 | — | — | — | — | — | — | — | 10.3 | 22.5 |
| Hydroxypropyl methyl cellulose | 16.3 | 11.4 | 17.5 | 8.7 | — | 29.3 | — | — | — | 4.4 |
| Croscarmellose sodium | 6.8 | 11.0 | 12.8 | 7.9 | 19.0 | 9.6 | 13.3 | 15.6 | 15.1 | 14.7 |
| Silicon dioxide | 0.86 | 0.80 | 2.25 | 1.24 | .95 | 1.34 | 0.80 | 1.66 | 0.79 | 2.37 |
| Magnesium stearate | 1.75 | 1.0 | 0.75 | 0.6 | 0.5 | 2.5 | 1.9 | 0.8 | 1.2 | 2.8 |
| Extended Release Layer | | | | | | | | | | |
| APAP | 150.0 | 150.0 | 125.0 | 75.0 | 100.0 | 165.0 | 135.0 | 225.0 | 210.0 | 150.0 |
| Hydrocodone bitartrate | 8.00 | 6.50 | 6.00 | 6.50 | 3.25 | 6.25 | 6.25 | 5.00 | 6.25 | 5.50 |
| Microcrystalline cellulose | 182.2 | 197.6 | 300.4 | 269.6 | 210.0 | 275.5 | 283.2 | 310.2 | 240.8 | 210.0 |
| Pregelatinized starch | 0.75 | 0.73 | 0.46 | 0.89 | 0.55 | 0.78 | 0.55 | 0.65 | 0.67 | 0.64 |
| Citric Acid Anhydrous | 0.25 | 0.36 | 0.38 | 0.34 | 0.37 | 0.23 | 0.14 | 0.40 | 0.70 | 0.70 |
| EDTA disodium salt, dihydrate | 0.23 | 0.09 | 0.14 | 0.06 | 0.183 | 0.035 | 0.049 | 0.03 | 0.105 | 0.075 |
| Hydroxypropyl cellulose | 34.7 | 321.9 | 88.4 | 212.9 | 11.9 | 37.7 | 34.2 | 17.4 | — | — |
| Polyox N12K | — | — | 252.4 | — | 290.3 | — | 248.2 | 279.2 | 175.2 | — |
| Polyox 303 | 275.8 | — | — | — | — | — | — | — | — | 224.5 |
| Hydroxypropyl methyl cellulose | — | 101.1 | — | 110.5 | — | 192.1 | — | — | 140.9 | 185.6 |
| Silicon Dioxide | 1.3 | 1.3 | 1.2 | 2.4 | 2.1 | 3.2 | 4.0 | 4.0 | 2.0 | 3.8 |
| Magnesium Stearate | 5.7 | 9.4 | 6.6 | 5.5 | 7.7 | 9.4 | 6.4 | 5.2 | 9.9 | 7.2 |

| | Formulation No. | | | | | | | | | |
|---|---|---|---|---|---|---|---|---|---|---|
| | 21 | 22 | 23 | 24 | 25 | 26 | 27 | 28 | 29 | 30 |
| Immediate Release Layer | | | | | | | | | | |
| APAP | 185.3 | 175.0 | 180.0 | 160.4 | 200.0 | 193.4 | 118.8 | 162.5 | 139.0 | 150.0 |
| Hydrocodone bitartrate | 1.100 | 1.75 | 2.00 | 2.50 | 1.25 | 1.00 | 2.75 | 1.875 | 1.75 | 1.875 |
| Microcrystalline cellulose | 23.0 | 17.0 | 19.0 | 27.0 | 16.0 | 18.0 | 18.0 | 14.0 | 21.0 | 24.0 |
| Pregelatinized starch | 0.05 | 0.15 | 0.25 | 0.10 | 0.05 | 0.30 | 0.20 | 0.25 | 0.15 | 0.20 |
| Citric Acid Anhydrous | 0.08 | 0.08 | 0.08 | 0.11 | 0.11 | 0.14 | 0.07 | 0.13 | 0.15 | 0.17 |
| EDTA disodium salt, dihydrate | 0.087 | 0.106 | 0.075 | 0.03 | 0.050 | 0.055 | 0.033 | 0.025 | 0.045 | 0.018 |
| Hydroxypropyl cellulose | 14.1 | 17.8 | — | — | 17.3 | — | 16.7 | 16.1 | 21.5 | — |
| Hypromellose | 2.5 | — | 3.2 | — | — | — | — | — | 8.9 | 19.5 |
| Hydroxypropyl methyl cellulose | — | — | 21.7 | 18.3 | — | 19.3 | — | — | — | 3.0 |
| Croscarmellose sodium | 10.0 | 11.0 | 11.5 | 11.5 | 13.0 | 14.5 | 14.5 | 12.5 | 14.0 | 12.5 |
| Silicon dioxide | 0.97 | 0.75 | 1.14 | 1.02 | 1.10 | 1.03 | 0.88 | 1.05 | 0.93 | 2.30 |
| Magnesium stearate | 1.5 | 1.0 | 1.0 | 0.5 | 0.5 | 2.0 | 2.0 | 0.5 | 1.5 | 2.5 |
| Extended Release Layer | | | | | | | | | | |
| APAP | 185.3 | 150.0 | 145.0 | 155.2 | 125.0 | 100.5 | 146.9 | 162.5 | 207.4 | 150.0 |
| Hydrocodone bitartrate | 6.900 | 5.75 | 5.50 | 5.00 | 6.25 | 6.50 | 7.25 | 5.625 | 4.75 | 6.625 |
| Microcrystalline cellulose | 175.4 | 180.0 | 302.2 | 275.0 | 214.8 | 250.0 | 245.7 | 203.6 | 288.3 | 200.5 |
| Pregelatinized starch | 0.60 | 0.60 | 0.70 | 0.70 | 0.70 | 0.75 | 0.75 | 0.75 | 0.85 | 0.85 |
| Citric Acid Anhydrous | 0.24 | 0.16 | 0.24 | 0.22 | 0.33 | 0.28 | 0.07 | 0.38 | 0.45 | 0.34 |
| EDTA disodium salt, dihydrate | 0.160 | 0.085 | 0.095 | 0.055 | 0.130 | 0.065 | 0.065 | 0.075 | 0.130 | 0.125 |
| Hydroxypropyl cellulose | 30.0 | 275.8 | 95.5 | 210.6 | 13.2 | 40.7 | 32.9 | 9.6 | — | — |
| Polyox N60K | 292.8 | — | — | — | 287.7 | — | — | 321.8 | 155.5 | — |
| Polyox 205 | — | — | 244.2 | — | — | — | 275.5 | — | — | 189.2 |
| Hydroxypropyl methyl cellulose | — | 103.2 | — | 134.2 | — | 182.2 | — | — | 155.5 | 210.2 |
| Silicon Dioxide | 1.8 | 1.3 | 1.5 | 2.3 | 2.4 | 3.0 | 3.5 | 3.6 | 2.0 | 2.5 |
| Magnesium Stearate | 7.5 | 8.0 | 7.4 | 8.1 | 7.5 | 10.2 | 9.9 | 7.2 | 10.3 | 10.3 |

CHART 1-continued

Representative Hydrocodone/Acetaminophen Formulations.

| | Formulation No. | | | | | | | | | |
|---|---|---|---|---|---|---|---|---|---|---|
| | 31 | 32 | 33 | 34 | 35 | 36 | 37 | 38 | 39 | 40 |
| Immediate Release Layer | | | | | | | | | | |
| APAP | 300.0 | 150.0 | 200.0 | 150.0 | 100.0 | 160.0 | 190.0 | 75.0 | 90.0 | 125.0 |
| Hydrocodone bitartrate | 2.00 | 1.00 | 1.50 | 3.50 | 2.75 | 1.25 | 1.25 | 2.50 | 1.75 | 3.00 |
| Microcrystalline cellulose | 21.5 | 18.5 | 25.3 | 35.0 | 15.7 | 27.1 | 9.9 | 13.9 | 24.2 | 16.9 |
| Pregelatinized starch | 0.03 | 0.30 | 0.25 | 0.27 | 0.08 | 0.35 | 0.75 | 0.09 | 0.15 | 0.26 |
| Citric Acid Anhydrous | 0.12 | 0.08 | 0.09 | 0.16 | 0.07 | 0.24 | 0.14 | 0.26 | 0.15 | 0.20 |
| EDTA disodium salt, dihydrate | 0.04 | 0.175 | 0.1 | 0.06 | 0.1 | 0.09 | 0.06 | 0.08 | 0.063 | 0.09 |
| Hydroxypropyl cellulose | — | 21.5 | 1.8 | 9.8 | 14.8 | — | 20.8 | 19.2 | 25.4 | — |
| Hypromellose | 2.5 | — | — | — | — | — | — | — | 10.3 | 22.5 |
| Hydroxypropyl methyl cellulose | 16.3 | 11.4 | 17.5 | 8.7 | — | 29.3 | — | — | — | 4.4 |
| Croscarmellose sodium | 6.8 | 11.0 | 12.8 | 7.9 | 19.0 | 9.6 | 13.3 | 15.6 | 15.1 | 14.7 |
| Silicon dioxide | 0.86 | 0.80 | 2.25 | 1.24 | .95 | 1.34 | 0.80 | 1.66 | 0.79 | 2.37 |
| Magnesium stearate | 1.75 | 1.0 | 0.75 | 0.6 | 0.5 | 2.5 | 1.9 | 0.8 | 1.2 | 2.8 |
| Extended Release Layer | | | | | | | | | | |
| APAP | 150.0 | 150.0 | 125.0 | 75.0 | 100.0 | 165.0 | 135.0 | 225.0 | 210.0 | 150.0 |
| Hydrocodone bitartrate | 8.00 | 6.50 | 6.00 | 6.50 | 3.25 | 6.25 | 6.25 | 5.00 | 6.25 | 5.50 |
| Microcrystalline cellulose | 182.2 | 197.6 | 300.4 | 269.6 | 210.0 | 275.5 | 283.2 | 310.2 | 240.8 | 210.0 |
| Pregelatinized starch | 0.75 | 0.73 | 0.46 | 0.89 | 0.55 | 0.78 | 0.55 | 0.65 | 0.67 | 0.64 |
| Citric Acid Anhydrous | 0.25 | 0.36 | 0.38 | 0.34 | 0.37 | 0.23 | 0.14 | 0.40 | 0.70 | 0.70 |
| EDTA disodium salt, dihydrate | 0.23 | 0.09 | 0.14 | 0.06 | 0.183 | 0.035 | 0.049 | 0.03 | 0.105 | 0.075 |
| Hydroxypropyl cellulose | 34.7 | 321.9 | 88.4 | 212.9 | 11.9 | 37.7 | 34.2 | 17.4 | — | — |
| Polyox N60K | — | — | 252.4 | — | 290.3 | — | 248.2 | 279.2 | 175.2 | — |
| Polyox 205 | 275.8 | — | — | — | — | — | — | — | — | 224.5 |
| Hydroxypropyl methyl cellulose | — | 101.1 | — | 110.5 | — | 192.1 | — | — | 140.9 | 185.6 |
| Silicon Dioxide | 1.3 | 1.3 | 1.2 | 2.4 | 2.1 | 3.2 | 4.0 | 4.0 | 2.0 | 3.8 |
| Magnesium Stearate | 5.7 | 9.4 | 6.6 | 5.5 | 7.7 | 9.4 | 6.4 | 5.2 | 9.9 | 7.2 |

| | Formulation No. | | | | | | | | | |
|---|---|---|---|---|---|---|---|---|---|---|
| | 41 | 42 | 43 | 44 | 45 | 46 | 47 | 48 | 49 | 50 |
| Immediate Release Layer | | | | | | | | | | |
| APAP | 185.3 | 175.0 | 180.0 | 160.4 | 200.0 | 193.4 | 118.8 | 162.5 | 139.0 | 150.0 |
| Hydrocodone bitartrate | 1.100 | 1.75 | 2.00 | 2.50 | 1.25 | 1.00 | 2.75 | 1.875 | 1.75 | 1.875 |
| Microcrystalline cellulose | 23.0 | 17.0 | 19.0 | 27.0 | 16.0 | 18.0 | 18.0 | 14.0 | 21.0 | 24.0 |
| Pregelatinized starch | 0.05 | 0.15 | 0.25 | 0.10 | 0.05 | 0.30 | 0.20 | 0.25 | 0.15 | 0.20 |
| Citric Acid Anhydrous | 0.08 | 0.08 | 0.08 | 0.11 | 0.11 | 0.14 | 0.07 | 0.13 | 0.15 | 0.17 |
| EDTA disodium salt, dihydrate | 0.087 | 0.106 | 0.075 | 0.03 | 0.050 | 0.055 | 0.033 | 0.025 | 0.045 | 0.018 |
| Hydroxypropyl cellulose | 14.1 | 17.8 | — | — | 17.3 | — | 16.7 | 16.1 | 21.5 | — |
| Hypromellose | 2.5 | — | 3.2 | — | — | — | — | — | 8.9 | 19.5 |
| Hydroxypropyl methyl cellulose | — | — | 21.7 | 18.3 | — | 19.3 | — | — | — | 3.0 |
| Croscarmellose sodium | 10.0 | 11.0 | 11.5 | 11.5 | 13.0 | 14.5 | 14.5 | 12.5 | 14.0 | 12.5 |
| Silicon dioxide | 0.97 | 0.75 | 1.14 | 1.02 | 1.10 | 1.03 | 0.88 | 1.05 | 0.93 | 2.30 |
| Magnesium stearate | 1.5 | 1.0 | 1.0 | 0.5 | 0.5 | 2.0 | 2.0 | 0.5 | 1.5 | 2.5 |
| Extended Release Layer | | | | | | | | | | |
| APAP | 185.3 | 150.0 | 145.0 | 155.2 | 125.0 | 100.5 | 146.9 | 162.5 | 207.4 | 150.0 |
| Hydrocodone bitartrate | 6.900 | 5.75 | 5.50 | 5.00 | 6.25 | 6.50 | 7.25 | 5.625 | 4.75 | 6.625 |
| Microcrystalline cellulose | 175.4 | 180.0 | 302.2 | 275.0 | 214.8 | 250.0 | 245.7 | 203.6 | 288.3 | 200.5 |
| Pregelatinized starch | 0.60 | 0.60 | 0.70 | 0.70 | 0.70 | 0.75 | 0.75 | 0.75 | 0.85 | 0.85 |
| Citric Acid Anhydrous | 0.24 | 0.16 | 0.24 | 0.22 | 0.33 | 0.28 | 0.07 | 0.38 | 0.45 | 0.34 |
| EDTA disodium salt, dihydrate | 0.160 | 0.085 | 0.095 | 0.055 | 0.130 | 0.065 | 0.065 | 0.075 | 0.130 | 0.125 |
| Hydroxypropyl cellulose | 30.0 | 275.8 | 95.5 | 210.6 | 13.2 | 40.7 | 32.9 | 9.6 | — | — |
| Polyox 1105 | 262.2 | — | — | — | 301.6 | — | — | 250.3 | 188.3 | — |
| Polyox N-750 | — | — | 244.2 | — | — | — | 275.5 | — | — | 189.2 |
| Hydroxypropyl methyl cellulose | — | 103.2 | — | 134.2 | — | 182.2 | — | — | 155.5 | 210.2 |
| Silicon Dioxide | 1.8 | 1.3 | 1.5 | 2.3 | 2.4 | 3.0 | 3.5 | 3.6 | 2.0 | 2.5 |
| Magnesium Stearate | 7.5 | 8.0 | 7.4 | 8.1 | 7.5 | 10.2 | 9.9 | 7.2 | 10.3 | 10.3 |

CHART 1-continued

Representative Hydrocodone/Acetaminophen Formulations.

| | Formulation No. | | | | | | | | | |
|---|---|---|---|---|---|---|---|---|---|---|
| | 51 | 52 | 53 | 54 | 55 | 56 | 57 | 58 | 59 | 60 |
| Immediate Release Layer | | | | | | | | | | |
| APAP | 300.0 | 150.0 | 200.0 | 150.0 | 100.0 | 160.0 | 190.0 | 75.0 | 90.0 | 125.0 |
| Hydrocodone bitartrate | 2.00 | 1.00 | 1.50 | 3.50 | 2.75 | 1.25 | 1.25 | 2.50 | 1.75 | 3.00 |
| Microcrystalline cellulose | 21.5 | 18.5 | 25.3 | 35.0 | 15.7 | 27.1 | 9.9 | 13.9 | 24.2 | 16.9 |
| Pregelatinized starch | 0.03 | 0.30 | 0.25 | 0.27 | 0.08 | 0.35 | 0.75 | 0.09 | 0.15 | 0.26 |
| Citric Acid Anhydrous | 0.12 | 0.08 | 0.09 | 0.16 | 0.07 | 0.24 | 0.14 | 0.26 | 0.15 | 0.20 |
| EDTA disodium salt, dihydrate | 0.04 | 0.175 | 0.1 | 0.06 | 0.1 | 0.09 | 0.06 | 0.08 | 0.063 | 0.09 |
| Hydroxypropyl cellulose | — | 21.5 | 1.8 | 9.8 | 14.8 | — | 20.8 | 19.2 | 25.4 | — |
| Hypromellose | 2.5 | — | — | — | — | — | — | — | 10.3 | 22.5 |
| Hydroxypropyl methyl cellulose | 16.3 | 11.4 | 17.5 | 8.7 | — | 29.3 | — | — | — | 4.4 |
| Croscarmellose sodium | 6.8 | 11.0 | 12.8 | 7.9 | 19.0 | 9.6 | 13.3 | 15.6 | 15.1 | 14.7 |
| Silicon dioxide | 0.86 | 0.80 | 2.25 | 1.24 | .95 | 1.34 | 0.80 | 1.66 | 0.79 | 2.37 |
| Magnesium stearate | 1.75 | 1.0 | 0.75 | 0.6 | 0.5 | 2.5 | 1.9 | 0.8 | 1.2 | 2.8 |
| Extended Release Layer | | | | | | | | | | |
| APAP | 150.0 | 150.0 | 125.0 | 75.0 | 100.0 | 165.0 | 135.0 | 225.0 | 210.0 | 150.0 |
| Hydrocodone bitartrate | 8.00 | 6.50 | 6.00 | 6.50 | 3.25 | 6.25 | 6.25 | 5.00 | 6.25 | 5.50 |
| Microcrystalline cellulose | 182.2 | 197.6 | 300.4 | 269.6 | 210.0 | 275.5 | 283.2 | 310.2 | 240.8 | 210.0 |
| Pregelatinized starch | 0.75 | 0.73 | 0.46 | 0.89 | 0.55 | 0.78 | 0.55 | 0.65 | 0.67 | 0.64 |
| Citric Acid Anhydrous | 0.25 | 0.36 | 0.38 | 0.34 | 0.37 | 0.23 | 0.14 | 0.40 | 0.70 | 0.70 |
| EDTA disodium salt, dihydrate | 0.23 | 0.09 | 0.14 | 0.06 | 0.183 | 0.035 | 0.049 | 0.03 | 0.105 | 0.075 |
| Hydroxypropyl cellulose | 34.7 | 321.9 | 88.4 | 212.9 | 11.9 | 37.7 | 34.2 | 17.4 | — | — |
| Polyox 1105 | — | — | 252.4 | — | 290.3 | — | 248.2 | 279.2 | 175.2 | — |
| Polyox N-750 | 275.8 | — | — | — | — | — | — | — | — | 224.5 |
| Hydroxypropyl methyl cellulose | — | 101.1 | — | 110.5 | — | 192.1 | — | — | 140.9 | 185.6 |
| Silicon Dioxide | 1.3 | 1.3 | 1.2 | 2.4 | 2.1 | 3.2 | 4.0 | 4.0 | 2.0 | 3.8 |
| Magnesium Stearate | 5.7 | 9.4 | 6.6 | 5.5 | 7.7 | 9.4 | 6.4 | 5.2 | 9.9 | 7.2 |

| | Formulation No. | | | | | | | | | |
|---|---|---|---|---|---|---|---|---|---|---|
| | 61 | 62 | 63 | 64 | 65 | 66 | 67 | 68 | 69 | 70 |
| Immediate Release Layer | | | | | | | | | | |
| APAP | 185.3 | 175.0 | 180.0 | 160.4 | 200.0 | 193.4 | 118.8 | 162.5 | 139.0 | 150.0 |
| Hydrocodone bitartrate | 1.100 | 1.75 | 2.00 | 2.50 | 1.25 | 1.00 | 2.75 | 1.875 | 1.75 | 1.875 |
| Microcrystalline cellulose | 23.0 | 17.0 | 19.0 | 27.0 | 16.0 | 18.0 | 18.0 | 14.0 | 21.0 | 24.0 |
| Pregelatinized starch | 0.05 | 0.15 | 0.25 | 0.10 | 0.05 | 0.30 | 0.20 | 0.25 | 0.15 | 0.20 |
| Citric Acid Anhydrous | 0.08 | 0.08 | 0.08 | 0.11 | 0.11 | 0.14 | 0.07 | 0.13 | 0.15 | 0.17 |
| EDTA disodium salt, dihydrate | 0.087 | 0.106 | 0.075 | 0.03 | 0.050 | 0.055 | 0.033 | 0.025 | 0.045 | 0.018 |
| Hydroxypropyl cellulose | 14.1 | 17.8 | — | — | 17.3 | — | 16.7 | 16.1 | 21.5 | — |
| Hypromellose | 2.5 | — | 3.2 | — | — | — | — | — | 8.9 | 19.5 |
| Hydroxypropyl methyl cellulose | — | — | 21.7 | 18.3 | — | 19.3 | — | — | — | 3.0 |
| Croscarmellose sodium | 10.0 | 11.0 | 11.5 | 11.5 | 13.0 | 14.5 | 14.5 | 12.5 | 14.0 | 12.5 |
| Silicon dioxide | 0.97 | 0.75 | 1.14 | 1.02 | 1.10 | 1.03 | 0.88 | 1.05 | 0.93 | 2.30 |
| Magnesium stearate | 1.5 | 1.0 | 1.0 | 0.5 | 0.5 | 2.0 | 2.0 | 0.5 | 1.5 | 2.5 |
| Extended Release Layer | | | | | | | | | | |
| APAP | 185.3 | 150.0 | 145.0 | 155.2 | 125.0 | 100.5 | 146.9 | 162.5 | 207.4 | 150.0 |
| Hydrocodone bitartrate | 6.900 | 5.75 | 5.50 | 5.00 | 6.25 | 6.50 | 7.25 | 5.625 | 4.75 | 6.625 |
| Microcrystalline cellulose | 175.4 | 180.0 | 302.2 | 275.0 | 214.8 | 250.0 | 245.7 | 203.6 | 288.3 | 200.5 |
| Pregelatinized starch | 0.60 | 0.60 | 0.70 | 0.70 | 0.70 | 0.75 | 0.75 | 0.75 | 0.85 | 0.85 |
| Citric Acid Anhydrous | 0.24 | 0.16 | 0.24 | 0.22 | 0.33 | 0.28 | 0.07 | 0.38 | 0.45 | 0.34 |
| EDTA disodium salt, dihydrate | 0.160 | 0.085 | 0.095 | 0.055 | 0.130 | 0.065 | 0.065 | 0.075 | 0.130 | 0.125 |
| Hydroxypropyl cellulose | 30.0 | 275.8 | 95.5 | 210.6 | 13.2 | 40.7 | 32.9 | 9.6 | — | — |
| Polyox 301 | 292.8 | — | — | — | 287.7 | — | — | 321.8 | 155.5 | — |
| Polyox N-80 | — | — | 244.2 | — | — | — | 275.5 | — | — | 189.2 |
| Hydroxypropyl methyl cellulose | — | 103.2 | — | 134.2 | — | 182.2 | — | — | 155.5 | 210.2 |
| Silicon Dioxide | 1.8 | 1.3 | 1.5 | 2.3 | 2.4 | 3.0 | 3.5 | 3.6 | 2.0 | 2.5 |
| Magnesium Stearate | 7.5 | 8.0 | 7.4 | 8.1 | 7.5 | 10.2 | 9.9 | 7.2 | 10.3 | 10.3 |

CHART 1-continued

Representative Hydrocodone/Acetaminophen Formulations.

| | Formulation No. | | | | | | | | | |
|---|---|---|---|---|---|---|---|---|---|---|
| | 71 | 72 | 73 | 74 | 75 | 76 | 77 | 78 | 79 | 80 |
| Immediate Release Layer | | | | | | | | | | |
| APAP | 300.0 | 150.0 | 200.0 | 150.0 | 100.0 | 160.0 | 190.0 | 75.0 | 90.0 | 125.0 |
| Hydrocodone bitartrate | 2.00 | 1.00 | 1.50 | 3.50 | 2.75 | 1.25 | 1.25 | 2.50 | 1.75 | 3.00 |
| Microcrystalline cellulose | 21.5 | 18.5 | 25.3 | 35.0 | 15.7 | 27.1 | 9.9 | 13.9 | 24.2 | 16.9 |
| Pregelatinized starch | 0.03 | 0.30 | 0.25 | 0.27 | 0.08 | 0.35 | 0.75 | 0.09 | 0.15 | 0.26 |
| Citric Acid Anhydrous | 0.12 | 0.08 | 0.09 | 0.16 | 0.07 | 0.24 | 0.14 | 0.26 | 0.15 | 0.20 |
| EDTA disodium salt, dihydrate | 0.04 | 0.175 | 0.1 | 0.06 | 0.1 | 0.09 | 0.06 | 0.08 | 0.063 | 0.09 |
| Hydroxypropyl cellulose | — | 21.5 | 1.8 | 9.8 | 14.8 | — | 20.8 | 19.2 | 25.4 | — |
| Hypromellose | 2.5 | — | — | — | — | — | — | — | 10.3 | 22.5 |
| Hydroxypropyl methyl cellulose | 16.3 | 11.4 | 17.5 | 8.7 | — | 29.3 | — | — | — | 4.4 |
| Croscarmellose sodium | 6.8 | 11.0 | 12.8 | 7.9 | 19.0 | 9.6 | 13.3 | 15.6 | 15.1 | 14.7 |
| Silicon dioxide | 0.86 | 0.80 | 2.25 | 1.24 | .95 | 1.34 | 0.80 | 1.66 | 0.79 | 2.37 |
| Magnesium stearate | 1.75 | 1.0 | 0.75 | 0.6 | 0.5 | 2.5 | 1.9 | 0.8 | 1.2 | 2.8 |
| Extended Release Layer | | | | | | | | | | |
| APAP | 150.0 | 150.0 | 125.0 | 75.0 | 100.0 | 165.0 | 135.0 | 225.0 | 210.0 | 150.0 |
| Hydrocodone bitartrate | 8.00 | 6.50 | 6.00 | 6.50 | 3.25 | 6.25 | 6.25 | 5.00 | 6.25 | 5.50 |
| Microcrystalline cellulose | 182.2 | 197.6 | 300.4 | 269.6 | 210.0 | 275.5 | 283.2 | 310.2 | 240.8 | 210.0 |
| Pregelatinized starch | 0.75 | 0.73 | 0.46 | 0.89 | 0.55 | 0.78 | 0.55 | 0.65 | 0.67 | 0.64 |
| Citric Acid Anhydrous | 0.25 | 0.36 | 0.38 | 0.34 | 0.37 | 0.23 | 0.14 | 0.40 | 0.70 | 0.70 |
| EDTA disodium salt, dihydrate | 0.23 | 0.09 | 0.14 | 0.06 | 0.183 | 0.035 | 0.049 | 0.03 | 0.105 | 0.075 |
| Hydroxypropyl cellulose | 34.7 | 321.9 | 88.4 | 212.9 | 11.9 | 37.7 | 34.2 | 17.4 | — | — |
| Polyox 301 | — | — | 252.4 | — | 290.3 | — | 248.2 | 279.2 | 175.2 | — |
| Polyox N-80 | 275.8 | — | — | — | — | — | — | — | — | 224.5 |
| Hydroxypropyl methyl cellulose | — | 101.1 | — | 110.5 | — | 192.1 | — | — | 140.9 | 185.6 |
| Silicon Dioxide | 1.3 | 1.3 | 1.2 | 2.4 | 2.1 | 3.2 | 4.0 | 4.0 | 2.0 | 3.8 |
| Magnesium Stearate | 5.7 | 9.4 | 6.6 | 5.5 | 7.7 | 9.4 | 6.4 | 5.2 | 9.9 | 7.2 |

*All weights in mg.

CHART 2

Additional Hydrocodone/Acetaminophen Formulations.

| | 81 | 82 | 83 | 84 | 85 | 86 | 87 | 88 | 89 | 90 |
|---|---|---|---|---|---|---|---|---|---|---|
| Immediate Release Layer | | | | | | | | | | |
| APAP | 325.0 | 325 | 325 | 325 | 325.0 | 325.0 | 325.0 | 325.0 | 325.0 | 325.0 |
| Hydrocodone bitartrate | 3.75 | 3.75 | 3.75 | 3.75 | 3.75 | 3.75 | 3.75 | 3.75 | 3.75 | 3.75 |
| Microcrystalline cellulose | 28.10 | 28.10 | 28.10 | 28.10 | 28.1 | 28.1 | 28.1 | 28.1 | 28.1 | 28.1 |
| Pregelatinized starch | 0.50 | 0.50 | 0.50 | 0.50 | 0.50 | 0.50 | 0.50 | 0.50 | 0.50 | 0.50 |
| Citric Acid Anhydrous | 0.25 | 0.25 | 0.25 | 0.25 | 0.25 | 0.25 | 0.25 | 0.25 | 0.25 | 0.25 |
| EDTA disodium salt, dihydrate | 0.05 | 0.05 | 0.05 | 0.05 | 0.05 | 0.05 | 0.05 | 0.05 | 0.05 | 0.05 |
| Hydroxypropyl cellulose | 32.23 | 32.24 | 32.24 | 32.24 | 32.24 | 32.24 | 32.24 | 32.24 | 32.24 | 32.24 |
| Croscarmellose sodium | 25.087 | 25.09 | 25.09 | 25.09 | 25.09 | 25.09 | 25.09 | 25.09 | 25.09 | 25.09 |
| Silicon dioxide | 2.09 | 2.09 | 2.09 | 2.09 | 2.09 | 2.09 | 2.09 | 2.09 | 2.09 | 2.09 |
| Magnesium stearate | 1.045 | 1.05 | 1.05 | 1.05 | 1.045 | 1.045 | 1.045 | 1.045 | 1.045 | 1.045 |
| Extended Release Layer | | | | | | | | | | |
| APAP | 325.0 | 325 | 325 | 325 | 325.0 | 325.0 | 325.0 | 325.0 | 325.0 | 325.0 |
| Hydrocodone bitartrate | 11.25 | 11.25 | 11.25 | 11.25 | 11.25 | 11.25 | 11.25 | 11.25 | 11.25 | 11.25 |
| Microcrystalline cellulose | 23.85 | 95.19 | 23.85 | 23.85 | 23.85 | 95.19 | 23.85 | 23.85 | 23.85 | 95.19 |
| Pregelatinized starch | 1.50 | 1.50 | 1.50 | 1.50 | 1.5 | 1.5 | 1.5 | 1.5 | 1.5 | 1.5 |
| Citric Acid Anhydrous | 0.75 | 0.75 | 0.75 | 0.75 | 0.75 | 0.75 | 0.75 | 0.75 | 0.75 | 0.75 |
| EDTA disodium salt, dihydrate | 0.15 | 0.15 | 0.15 | 0.15 | 0.15 | 0.15 | 0.15 | 0.15 | 0.15 | 0.15 |
| Hydroxypropyl cellulose | 19.16 | 19.16 | 19.16 | 19.16 | 19.16 | 19.16 | 19.16 | 19.16 | 19.16 | 19.16 |
| Polyox 1105 | 321.02 | 249.68 | — | 321.02 | — | 249.68 | 321.02 | — | — | — |
| Polyox N12K | — | — | 321.02 | — | — | — | — | 321.02 | — | — |
| Polyox N6OK | — | — | — | — | 321.02 | — | — | — | 321.02 | 249.68 |
| Silicon Dioxide | — | — | — | — | — | 3.57 | 3.57 | 3.57 | 3.57 | 3.57 |
| Magnesium Stearate | 3.57 | 3.57 | 3.57 | 3.57 | 3.57 | 7.13 | 7.13 | 7.13 | 7.13 | 7.13 |

*All weights in mg.

III. Methods for Preparing Solid Dosage Forms of the Pharmaceutical Composition

Another aspect of the disclosure provides methods for preparing solid dosage forms of the pharmaceutical composition that provide extended release of hydrocodone and acetaminophen. Solid dosage compositions in the form of tablets may be produced using any suitable method known in the art including but not limited to wet granulation, dry granulation, direct compression, and combinations thereof.

Granulation is a manufacturing process which increases the size and homogeneity of active pharmaceutical ingredients and excipients that comprise a solid dose composition. The granulation process, which is often referred to as agglomeration, changes important physical characteristics of the dry composition, with the aim of improving manufacturability and, thereby, product quality, as well as providing desired release kinetics. Wet granulation is by far the more prevalent agglomeration process utilized within the pharmaceutical industry. Most wet granulation procedures follow some basic steps; the active agent(s) and excipients are mixed together, and a binder solution is prepared and added to the powder mixture to form a wet mass. The moist particles are then dried and sized by milling or by screening through a sieve. In some cases, the wet granulation is "wet milled" or sized through screens before the drying step. The wet granulation process may be a high shear granulation process or a fluid bed granulation process. Several methods of granulation are described in co-pending application U.S. application Ser. No. 13/166,770, filed Jun. 22, 2011, which is incorporated herein by reference in its entirety.

After granulation and drying of the resultant particles, batches are characterized with respect to properties such as final Loss on Drying (LOD), bulk density, tap density, and particle size. Loss on Drying (LOD) typically is determined after each granulation using the Moisture Analyzer. Several 1 g samples may be taken and loaded into the moisture analyzer. The samples may be run for 5 minutes at a temperature of 105° C. In another embodiment, the samples may be run at 105° C. until there is no weight fluctuation in order to determine the LOD.

Bulk and tap densities may be determined as follows. A graduated cylinder is filled with a certain amount of material (e.g., 30-40 g or 82-88 g), and the volume recorded to determine the material bulk density. Tap density can be determined with a help of a Tap Density Tester by exposing the material to 100 taps per test and recording the new volume.

Particle size determination generally is performed immediately after granulation, after sieving through 20 mesh screen to remove agglomerates. Particle diameter may be determined with a sieve-type particle diameter distribution gauge using sieves with openings of 30, 40, 60, 80, 120, and 325 mesh. Fractions may be weighed on a Mettler balance to estimate size distribution. This provides determination of the quantitative ratio by particle diameter of composition comprising extended release particles. Sieve analysis according to standard United States Pharmacopoeia methods (e.g., USP-23 NF 18), may be done such as by using a Meinzer II Sieve Shaker.

In one embodiment, the method for preparing dosage forms of the pharmaceutical composition may comprise wet granulating a first mixture comprising hydrocodone, acetaminophen, and a binder to produce a first granulation mixture. The wet granulation process may be a fluid bed granulation process. In additional embodiments, the first mixture may further comprise at least one additional excipient selected from the group consisting of fillers, lubricants, antioxidants, chelating agents, and color agents. The first granulation mixture may be blended with an extended release polymer and one or more excipients, as listed above, to form at least one extended release portion of a dosage form. In certain embodiments, the extended release polymer may be a polyethylene oxide.

In another embodiment, the method further comprises wet granulating a second mixture comprising hydrocodone, acetaminophen, and a binder to form a second granulation mixture. The wet granulation process may be a fluid bed granulation process. In some embodiments, the second mixture may further comprise at least one additional excipient selected from the group consisting of fillers, lubricants, disintegrants, antioxidants, chelating agents, and color agents. The second granulation mixture may be blended with one or more excipients, as listed above, to form an immediate release portion of a dosage form.

In an additional embodiment, the method may further comprise compressing the at least one extended release portion and the at least one immediate release portion into a tablet. The tablet may be a bilayer tablet. The tablet may be coated with a tablet coating.

In another embodiment, the method may comprise granulating via a high shear wet granulation process a mixture comprising hydrocodone and at least one excipient to form hydrocodone particles. The hydrocodone particles may be dried at a suitable temperature. The hydrocodone particles comprising hydrocodone may be granulated via a fluid bed granulation process with acetaminophen, a binder, and an optional excipient to form the granulation mixture. The granulation mixture may be blended with an extended release polymer and at least one excipient to form an extended release portion of a solid dosage form.

In a further embodiment, the method may further comprise granulating via a fluid bed granulation process hydrocodone particles comprising hydrocodone with acetaminophen, a binder, and an optional excipient to form another granulation mixture. This granulation mixture may be blended with one or more excipients to form an immediate release portion of a solid dosage form.

In an additional embodiment, the method may further comprise compressing the at least one extended release portion comprising hydrocodone particles and the at least one immediate release portion comprising hydrocodone particles into a tablet. In one embodiment, the method comprises compressing one extended release portion comprising the hydrocodone particles and one immediate release portion comprising the hydrocodone particles into a bilayer tablet. The tablet may be coated with a tablet coating.

In another embodiment, wet granulation of either mixture may produce particles with a bulk density ranging from about 0.30 to 0.40 grams/milliliter (g/mL). In other aspects, the wet granulation may produce particles with a tap density ranging from about 0.35 g/mL to about 0.45 g/mL. In other embodiments, the wet granulation may produce particles, wherein at least about 50% of the particles have a size greater than 125 microns. In still other embodiments, the wet granulation may produce particles wherein about 20% to about 65% of the particles have a size greater than about 125 microns and less than about 250 microns.

Tablets generally are characterized with respect to disintegration and dissolution release profiles as well as tablet hardness, friability, and content uniformity.

In vitro dissolution profiles for the tablets may be determined using a USP Type II apparatus, with a paddle speed of either about 100 rpm or 150 rpm, in 0.1 N HCl, at 37° C. Samples of 5 ml at each time-point may be taken without media replacement at 0.08, 0.25, 0.5, 1, 2, 4, 6, 8 and 12 hours, for example. In some embodiments, the dissolution profiles may be determined at varying pH values, such as at a pH of about 3.0, 3.5, 4.0, 4.5, 5.0, 5.5, 6.0 or 6.5. The fluid used may be, for example, HCl, phosphate buffer, or simulated gastric fluid. The resulting cumulative dissolution profiles for the tablets are based upon a theoretical percent active added to the compositions.

A tablet preferably disintegrates before it dissolves. A disintegration tester measures the time it takes a tablet to break apart in solution. The tester suspends tablets in a solution bath for visual monitoring of the disintegration rate. Both the time to disintegration and the disintegration consistency of all tablets may be measured. The disintegration profile may be determined in a USP Disintegration Tester in 0.1 N HCl of pH 1.2. The fluid used may be, for example, HCl, phosphate buffer, or simulated gastric fluid. Samples, 1-5 ml at each time-point, may be taken, for example, without media replacement at 0.5, 1, 2, 3, 4, 5, 6, 7 and 8 hours. The resulting cumulative disintegration profiles are based upon a theoretical percent active added to the pharmaceutical compositions.

After tablets are formed by compression, it is desired that the tablets have a strength of at least 9-25 Kiloponds (kp), or at least about 12-20 kp. A hardness tester generally is used to determine the load required to diametrically break the tablets (crushing strength) into two equal halves. The fracture force may be measured using a Venkel Tablet Hardness Tester, using standard USP protocols.

Friability is a well-known measure of a tablet's resistance to surface abrasion that measures weight loss in percentage after subjecting the tablets to a standardized agitation procedure. Friability properties are especially important during any transport of the dosage form as any fracturing of the final dosage form may result in a subject receiving less than the prescribed medication. Friability may be determined using a Roche Friability Drum according to standard USP guidelines which specifies the number of samples, the total number of drum revolutions, and the drum rpm to be used. Friability values of from 0.8 to 1.0% generally are regarded as constituting the upper limit of acceptability.

The prepared tablets generally are tested for content uniformity to determine if they meet the pharmaceutical requirement of an acceptance value of 15 or less. Each tablet may be placed in a solution of 60% methanol/40% isopropanol and stirred at room temperature until the tablet disintegrates. The solution containing the dissolved tablet may be further diluted in 90% water/10% isopropanol/0.1% heptafluorobutyric acid and generally is analyzed by HPLC.

IV. Method for Reducing the Risk Of Acetaminophen-Induced Hepatic Damage

The present disclosure also provides methods for reducing the risk of acetaminophen-induced hepatic damage in a subject being treated for pain with a dosage regimen that comprises administering to the subject at least two consecutive doses of a pharmaceutical composition comprising hydrocodone and acetaminophen. The method comprises administering a first dose of a pharmaceutical composition comprising at least one extended release portion comprising the acetaminophen, the hydrocodone or a combination thereof, and an extended release component to the subject, wherein the composition maintains a therapeutic blood plasma concentration of hydrocodone of at least 5 ng/mL from about 0.75 hours to about 10 hours after administration of the composition, and wherein at least about 90% of the acetaminophen is released from the composition by about 8 hours after administration of the composition such that, by about 10 hours after administration of the composition, acetaminophen has a blood plasma concentration that is less than about 30% of acetaminophen's maximum plasma concentration. The method further comprises administering a second dose of the pharmaceutical composition to the subject at about 12 hours after administration of the first dose.

Avoiding toxic intermediate formation is an important strategy in addressing product safety. Indeed, acetaminophen is absorbed from the stomach and small intestine and primarily metabolized by conjugation in the liver to non-toxic, water-soluble compounds that are eliminated in the urine. When the maximum daily dose ("MDD") is exceeded over a prolonged period, metabolism by conjugation becomes saturated, and excess acetaminophen is oxidatively metabolized by the CYP enzymes (CYP2E1, 1A2, 2A6, 3A4) to a reactive metabolite, N-acetyl-p-benzoquinone-imine (NAPQI). NAPQI has an extremely short half-life, and rapidly conjugates with available glutathione, which acts as a sulfhydryl donor. The reduced NAPQI is then renally excreted. The liver plays a central role in the turnover of glutathione in the body. Given that toxicity due to NAPQI formation occurs via necrosis of the liver following the formation of toxic adducts, minimizing glutathione depletion and enhancing glutathione regeneration in the liver is an important concern.

Human erythrocyte data resulting from hepatic turnover demonstrate a time-delayed response to redox and free radical insults via glutathione depletion and regeneration. The hepatic dynamics of glutathione formation and depletion in animal data using hepatic models can also be reviewed. In Swiss mice, the dynamics of glutathione depletion was investigated in detail for acetaminophen doses ranging from (100 mg/kg to 600 mg/kg) in work done by Brzeznicka and Piotrowski (1989). Under one embodiment of the present invention, the intended dosage for patients with acute pain is 1.3 g/day of acetaminophen. Assuming a subject's weight of 70 kg, this is $1.229 \times 10^{-4}$ moles/kg/day in human subjects. In Swiss mice, 400 mg/kg and 600 mg/kg are $2.65 \times 10^{-3}$ moles/kg/day and $3.97 \times 10^{-3}$ moles/kg/day, respectively, resulting in a 22-fold and a 32-fold safety exposure ratio, as compared with human levels. The bioequivalence level is 95%. Brzeiznicka and Piotrowski report that circulating hepatic GSH changes in mice began within 15 min after acetaminophen administration, and depletion followed a pattern that was strictly dose dependent, reaching a minimum GSH level 2 hrs after injection for the all dose groups, rebounding to initial levels between hours 8 and 12. Taken together, these results support the hypothesis that exposing subjects to the lower end of the therapeutic window of acetaminophen may provide benefit in terms of the patient's ability to regenerate physiologically protective levels of glutathione. Thus, the pharmaceutical formulations disclosed herein, which are designed to allow for a two hour break in acetaminophen exposure in each twelve hour exposure window allows for restorative hepatic regeneration of the subject's glutathione levels during that period when the acetaminophen concentrations are at their lowest or absent, while still preserving the considerable benefits of the potentiating effects of combination analgesia.

As mentioned above, acetaminophen is primarily metabolized via conjugation reactions, e.g., glucuronidation and sulfation, in the liver to nontoxic, water-soluble compounds that are rapidly eliminated from the body. A small proportion of acetaminophen is metabolized by the cytochrome P450 system to the reactive metabolite, NAPQI. Generally, this toxic metabolite is rapidly detoxified by conjugation to glutathione to form a non-toxic metabolite that is renally excreted. However, if the conjugation pathways become saturated and more acetaminophen is metabolized via the cytochrome P450 pathway, the pool of available glutathione may become depleted. With insufficient glutathione to bind to and inactivate NAPQI, this toxic metabolite is able to react with the sulfhydryl groups of cellular proteins initiating a cascade of cellular damage, which may lead to liver necrosis, and, ultimately, liver failure.

The method disclosed herein addresses the problem of depleted stores of glutathione by providing a period of time during the later part of the dosing interval during which the release of acetaminophen is low because most of the acetaminophen has already been released from the composition. The period of time during which the release of acetaminophen is low is called the acetaminophen "time-off" period. As a consequence of this acetaminophen time-off period, the plasma levels of acetaminophen fall to sufficiently low levels such that the metabolic burden on the liver is reduced, thereby allowing the depleted stores of glutathione to be replenished via the continuous glutathione manufacturing pathway comprising the glutathione synthase pathway. Because the levels of glutathione are able to be restored before the next dose, the risk of acetaminophen-induced hepatic damage is significantly reduced.

Additionally, the acetaminophen time-off period provided by the compositions disclosed herein may provide an added and beneficial precaution for any subject undergoing acetaminophen therapy to avoid an inadvertent reduction in glutathione stores and any potential acetaminophen-induced hepatic damage. In particular, the acetaminophen time-off period provided by the compositions disclosed herein may be especially useful during chronic administration of analgesic compositions comprising acetaminophen. The subject may be at increased risk for developing acetaminophen-induced hepatic damage because of frequent and regular user of alcohol (i.e., ethanol), concurrent administration of acetaminophen from another source (e.g., an over-the-counter medication), poor diet, and/or compromised liver function.

In general, the compositions disclosed herein are formulated such that the rate of release of acetaminophen is high during the first several hours of the dosing interval and the rate of release of acetaminophen is low during the last several hours of the dosing interval. More specifically, the compositions are formulated to release from about 40% to about 65% of the acetaminophen in about 30 minutes, from about 55% to about 80% of the acetaminophen in about 2 hours, from about 65% to about 92% of the acetaminophen in about 4 hours, and from about 67% to about 95% of the acetaminophen in about 8 hours, wherein the dosing interval is about 12 hours. In another, the compositions are formulated to release from about 45% to about 60% of the acetaminophen in about 30 minutes, from about 57% to about 75% of the acetaminophen in about 2 hours, from about 67% to about 90% of the acetaminophen in about 4 hours, and from about 70% to about 95% of the acetaminophen in about 8 hours, wherein the dosing interval is about 12 hours. In yet another embodiment, during the final 4 hours of a 12 hour dosing interval, only about 5% of the acetaminophen remains to be released from the composition.

The subject may be a mammal, and in certain embodiments, the subject may be a human. In various embodiments, the at least two consecutive doses of the analgesic composition may be administered to the subject at 8 hour intervals, 10 hour intervals, 12 hour intervals, 18 hour intervals, or 24 hour intervals.

The method for reducing the risk of acetaminophen-induced hepatic damage disclosed herein may further comprise administering additional doses of the pharmaceutical composition at regular dosing intervals, such as e.g., at 12 hour intervals. During the latter part of each dosing interval, therefore, the acetaminophen time-off period allows depleted stores of glutathione to be replenished, thereby reducing the risk of acetaminophen-induced hepatic damage in subjects being treated for pain with a composition comprising acetaminophen.

V. Method for Treating Pain

Also provided is a method for treating pain in a subject in need of such treatment with a pharmaceutical composition that comprises hydrocodone and acetaminophen, wherein the method comprises administering an effective amount of any of the pharmaceutical compositions disclosed herein. The method comprises orally administering to the subject an effective amount of a pharmaceutical composition comprising at least one extended release portion comprising hydrocodone, acetaminophen and combination thereof, and an extended release component, wherein the composition maintains a therapeutic plasma concentration of hydrocodone of at least about 5 ng/mL from about 0.75 hour to about 10 hours after administration of the composition, and wherein at least about 90% of the acetaminophen is released from the composition by about 8 hours after administration of the composition such that, by about 10 hours after administration of the composition, acetaminophen has a blood plasma concentration that is less than about 30% of acetaminophen's maximum plasma concentration.

In some embodiments, the subject may be suffering from or diagnosed with chronic pain. In yet another embodiment, the subject may be suffering from or diagnosed with acute pain. In still another embodiment, the subject may be suffering from or diagnosed with moderate to severe acute pain. In yet other embodiments, the subject may be suffering from or diagnosed with both chronic and acute pain. The subject may be a mammal, and in certain embodiments, the subject may be a human.

In one embodiment, the effective amount of a pharmaceutical composition may be 15 mg of hydrocodone and 650 mg of acetaminophen. For example, one solid dosage form comprising 15 mg of hydrocodone and 650 mg of acetaminophen may be administered. Alternatively, two solid dosage forms with each comprising 7.5 mg of hydrocodone and 325 mg of acetaminophen may be administered. In another embodiment, the effective amount of a pharmaceutical composition may be 7.5 mg of hydrocodone and 325 mg of acetaminophen, wherein one solid dosage form comprising 7.5 mg of hydrocodone and 325 mg of acetaminophen may be administered. In yet another embodiment, the effective amount of a pharmaceutical composition may be 20 mg of hydrocodone and 650 mg of acetaminophen. For example, one solid dosage form comprising 20 mg of hydrocodone and 650 mg of acetaminophen may be administered. Alternatively, two solid dosage forms with each comprising 10 mg of hydrocodone and 325 mg of acetaminophen may be administered. In another embodiment, the effective amount of a pharmaceutical composition may be 10 mg of hydrocodone and 325 mg of acetaminophen, wherein one solid dosage form comprising 10 mg of hydrocodone and 325 mg of acetaminophen may be administered. In still yet another embodiment, the effective amount of a pharmaceutical composition may be 30 mg of hydrocodone and 650 mg of acetaminophen. For example, one solid dosage form comprising 30 mg of hydrocodone and 650 mg of acetaminophen may be administered. Alternatively, two solid dosage forms with each comprising 15 mg of hydrocodone and 325 mg of acetaminophen may be administered. In another embodiment, the effective amount of a pharmaceutical composition may be 15 mg of hydrocodone and 325 mg of acetaminophen, wherein one solid dosage form comprising 15 mg of hydrocodone and 325 mg of acetaminophen may be administered.

The dosing intervals of the effective amount of the pharmaceutical composition can and will vary. For example, an effective amount of the pharmaceutical composition may be administered once a day, twice a day, or three times a day. In another embodiment, an effective amount of the pharmaceutical composition may be administered twice a day.

In general, therapeutic plasma concentrations of hydrocodone and acetaminophen are attained within about 5 minutes, 10 minutes, 15 minutes, 20 minutes, 25 minutes, 30 minutes, 35 minutes, 40 minutes, 45 minutes, 50 minutes, 55 minutes, or 60 minutes after administration of the first dose of the pharmaceutical composition. Accordingly, depending upon the severity of the pain, onset on analgesia may be attained within about 5 minutes, 10 minutes, 15 minutes, 20 minutes, 25 minutes, 30 minutes, 35 minutes, 40 minutes, 45 minutes, 50 minutes, 55 minutes, or 60 minutes after administration of the composition. Onset of analgesia may be measured by the double stopwatch method or other pain assessments measures such as duration of the pain and pain intensity. Generally, analgesia or pain relief will be maintained throughout the duration of the dosing interval. For example, in one embodiment, analgesia or pain relief will be maintained for 12 hours. Upon administration of the next dose of the pharmaceutical composition, therefore, analgesia or pain relief may be maintained. Accordingly, analgesia or pain relief will be maintained as long as therapeutic amounts of the pharmaceutical composition are administered at regular dosing intervals. Moreover, pain relief may be managed such that no break-through episodes of pain occur.

In some embodiments, an effective amount of the pharmaceutical composition may be administered to a subject in a fed state. In general, a fed state is defined as having consumed food within about 30 min prior to administration of the pharmaceutical composition. The food may be a high fat meal, a low fat meal, a high calorie meal, or a low calorie meal. In other embodiments, an effective amount of the pharmaceutical composition may be administered to a subject in a fasted state. In general, a fasted state is defined as not having ingested food for at least 10 hours prior to administration of the pharmaceutical composition. In some embodiments, the pharmaceutical composition may be administered to a subject who has fasted for at least 10 hours prior to the first dose and who fasts for at least one hour prior to administration of subsequent doses. In other embodiments, the pharmaceutical composition may be administered to a subject who has fasted for at least 1 hour, 2 hours, 3 hours, 4 hours, 5 hours, 6 hours, 7 hours, 8 hours, 9 hours, or 10 hours prior to administration of each dose.

The method of the present invention is useful for treating numerous pain states that are currently being treated with conventional immediate release compositions comprising acetaminophen and hydrocodone. These and additional pain states include, by way of illustration and not limitation, headache pain, pain associated with migraine, neuropathic pain selected from the group consisting of diabetic neuropathy, HIV sensory neuropathy, post-herpetic neuralgia, post-thoracotomy pain, trigeminal neuralgia, radiculopathy, neuropathic pain associated with chemotherapy, reflex sympathetic dystrophy, back pain, peripheral neuropathy, entrapment neuropathy, phantom limb pain, and complex regional pain syndrome, dental pain, pain associated with a surgical procedure and or other medical intervention, bone cancer pain, joint pain associated with psoriatic arthritis, osteoarthritic pain, rheumatoid arthritic pain, juvenile chronic arthritis associated pain, juvenile idiopathic arthritis associated pain, Spondyloarthropathies (such as ankylosing spondylitis (Mb Bechterew) and reactive arthritis (Reiter's syndrome) associated pain), pain associated with psoriatic arthritis, gout pain, pain associated with pseudogout (pyrophosphate arthritis), pain associated with systemic lupus erythematosus (SLE), pain associated with systemic sclerosis (scleroderma), pain associated with Behcet's disease, pain associated with relapsing polychondritis, pain associated with adult Still's disease, pain associated with transient regional osteoporosis, pain associated with neuropathic arthropathy, pain associated with sarcoidosis, arthritic pain, rheumatic pain, joint pain, osteoarthritic joint pain, rheumatoid arthritic joint pain, juvenile chronic arthritis associated joint pain, juvenile idiopathic arthritis associated joint pain, Spondyloarthropathies (such as ankylosing spondylitis (Mb Bechterew) and reactive arthritis (Reiter's syndrome) associated joint pain), gout joint pain, joint pain associated with pseudogout (pyrophosphate arthritis), joint pain associated with systemic lupus erythematosus (SLE), joint pain associated with systemic sclerosis (scleroderma), joint pain associated with Behcet's disease, joint pain associated with relapsing polychondritis, joint pain associated with adult Still's disease, joint pain associated with transient regional osteoporosis, joint pain associated with neuropathic arthropathy, joint pain associated with sarcoidosis, arthritic joint pain, rheumatic joint pain, acute pain, acute joint pain, chronic pain, chronic joint pain, inflammatory pain, inflammatory joint pain, mechanical pain, mechanical joint pain, pain associated with the fibromyalgia syndrome (FMS), pain associated with polymyalgia rheumatica, monarticular joint pain, polyarticular joint pain, nociceptive pain, psychogenous pain, pain of unknown etiology, pain mediated by IL-6, IL-6 soluble receptor, or IL-6 receptor, pain associated with a surgical procedure in a patient with a clinical diagnosis of OA, pain like static allodynia, pain like dynamic allodynia, and/or pain associated with Crohn's disease.

Having described the invention in detail, it will be apparent that modifications and variations are possible without departing from the scope of the invention defined in the appended claims.

EXAMPLES

The following examples are included to demonstrate certain embodiments of the invention. Those of skill in the art should, however, in light of the present disclosure, appreciate that modifications can be made in the specific embodiments that are disclosed and still obtain a like or similar result without departing from the spirit and scope of the invention, therefore all matter set forth is to be interpreted as illustrative and not in a limiting sense.

Example 1

Pharmacokinetic Study Involving Hydrocodone and Acetaminophen

A four-way crossover pharmacokinetic study was conducted. In a first trial (Treatment A), thirty-five subjects in a fasted state were administered a single, two-tablet dose of hydrocodone/acetaminophen, each tablet containing 7.5 mg hydrocodone, 325 mg acetaminophen, and having slow release properties as compared to an immediate release formulation. (See selected examples from Chart No. 1). In a second trial (Treatment B), thirty-five subjects in a fasted state were administered a single, two-tablet dose of hydrocodone/acetaminophen, each tablet containing 7.5 mg hydrocodone, 325 mg acetaminophen, and having medium release properties as compared to an immediate release formulation. (See selected examples from Chart No. 1). In a third trial (Treatment C), thirty-five subjects in a fed state were administered a single, two-tablet medium-release dose of hydrocodone/acetaminophen, each tablet containing 7.5 mg hydrocodone, 325 mg acetaminophen, and having medium release properties as compared to an immediate release formulation. (See selected examples from Chart Nos. 1 and 3). In a fourth trial (Treatment D), thirty-five subjects were administered a single, two-tablet dose of an immediate release tablet containing 7.5 mg hydrocodone and 325 mg acetaminophen.

The pharmacokinetic profiles from time 0 to 36 hours for hydrocodone and acetaminophen in each of these trials are shown in FIGS. 1 and 2, respectively. The pharmacokinetic profiles from time 0 to 12 hours for hydrocodone and acetaminophen in each of these trials are shown in FIGS. 3 and 4, respectively. The pharmacokinetic parameters of hydrocodone and acetaminophen are summarized in Tables 1 and 2, respectively. The simulated pharmacokinetic profiles from time 0 to 144 hours for hydrocodone and acetaminophen in each of these trials are shown in FIGS. 5 and 6, respectively.

These results indicate that the subjects exhibited an initial rapid rise in hydrocodone concentrations to provide early onset of action with the concentrations falling slowly over a period of twelve hours. The median $T_{lag}$ was unaffected by the formulations in comparison to an immediate release tablet containing 7.5 mg hydrocodone and 325 mg acetaminophen. Subjects also exhibited an initial rapid rise in acetaminophen concentrations to provide the desired early onset of action with the concentrations reaching levels that were lower than an immediate release tablet containing 7.5 mg hydrocodone and 325 mg acetaminophen at around twelve hours. Accordingly, the pharmaceutical compositions administered in Treatments A-C exhibited the desired APAP "time-off" feature in their pharmacokinetic profiles.

Administration of the pharmaceutical formulations with food had no effect on Cmax and AUC of hydrocodone, although the $T_{max}$ was delayed by two hours. $T_{lag}$ was unaffected. The Cmax of APAP decreased by about 31% when administered with food, but there was no change in AUC. $T_{max}$ of APAP was delayed by a little more than one hour. No dose dumping was observed from any of the formulations.

The pharmacokinetic profiles of both the pharmaceutical formulations having slow and medium release properties as compared to an immediate release formulation satisfy the desired pharmacokinetic parameters for both hydrocodone and acetaminophen. The observed Cmax and AUC values were suitable for hydrocodone/acetaminophen formulations containing an immediate release and extended release portion.

TABLE 1

Pharmacokinetic parameters for hydrocodone

| Parameter | Treatment A, Mean (SD) (N = 35) | Treatment B, Mean (SD) (N = 35) | Treatment C, Mean (SD) (N = 35) | Treatment D, Mean (SD) (N = 35) |
|---|---|---|---|---|
| $AUC_{0-t}$ (ng · h/mL) | 254.12 (71.48) | 243.88 (67.86) | 265.08 (73.62) | 261.60 (72.55) |
| $AUC_{0-inf}$ (ng · h/mL) | 264.47 (72.66) | 251.04 (69.72) | 268.73 (75.25) | 264.79 (73.55) |
| $C_{max}$ (ng/mL) | 18.62 (5.38) | 18.93 (5.58) | 19.73 (4.06) | 22.84 (6.51) |
| $T_{max}$ (h)[a] | 4.05 (2.00-7.00) | 4.00 (1.00-7.00) | 5.92 (2.00-12.08) | 8.00 (0.67-10.02) |
| $t_{lag}$ (h)[a] | 0.17 (0.00-0.37) | 0.17 (0.00-0.48) | 0.17 (0.00-0.67) | 0.17 (0.00-0.33) |
| $t_{1/2}$ (h) | 7.14 (2.55) | 6.70 (1.56) | 4.91 (0.59) | 4.87 (0.57) |
| $K_{el}$ (h$^{-1}$) | 0.1087 (0.0351) | 0.1087 (0.0238) | 0.1431 (0.0174) | 0.1442 (0.0171) |

[a]Median (minimum-maximum).

TABLE 2

Pharmacokinetic parameters for acetaminophen

| Parameter | Treatment A, Mean (SD) (N = 35) | Treatment B, Mean (SD) (N = 35) | Treatment C, Mean (SD) (N = 35) | Treatment D Mean (SD) (N = 35) |
|---|---|---|---|---|
| $AUC_{0-t}$ (ng · h/mL) | 30578 (9205) | 28939 (8364) | 29900 (8544) | 30771 (9518) |
| $AUC_{0-inf}$ (ng · h/mL) | 33417 (9306) | 31073 (8688) | 31512 (8943) | 31833 (9831) |
| $C_{max}$ (ng/mL) | 5030 (1678) | 4950 (1586) | 3343 (847) | 4755 (1673) |
| $T_{max}$ (h)[a] | 0.67 (0.33-2.00) | 0.67 (0.22-1.03) | 2.00 (0.33-5.92) | 0.67 (0.33-7.00) |
| $t_{lag}$ (h)[a] | 0.00 (0.00-0.33) | 0.00 (0.00-0.17) | 0.17 (0.00-0.50) | 0.00 (0.00-0.33) |
| $t_{1/2}$ (h) | 8.05 (3.33) | 6.57 (2.11) | 5.10 (2.24) | 4.36 (1.32) |
| $K_{el}$ (h$^{-1}$) | 0.1030 (0.0478) | 0.1196 (0.0504) | 0.1529 (0.0498) | 0.1718 (0.0509) |

[a]Median (minimum-maximum).

Example 2

Clinical Pharmacokinetic Analysis of an Extended Release Formulation of Hydrocodone/Acetaminophen Administered Under Fed and Fasted Conditions An open-label, randomized, three-period crossover study was conducted to evaluate the pharmacokinetics (PK), bioavailability, and safety of two tablets of a multi-layer extended-release formulation (7.5 mg hydrocodone bitartrate (HB)/325 mg acetaminophen (APAP)), administered as a single dose in normal, healthy subjects under fed (high-fat or and low-fat meal) and fasted conditions (i.e., 10 hr fast).

This single center, open-label, randomized, 3-period, 6-sequence crossover study in normal, healthy subjects was designed to evaluate the effect of a high-fat and low-fat meal on the PK, bioavailability, and safety of a multilayer ER tablet formulation of 7.5 mg HB/325 mg APAP (see selected example from Chart No. 1). The formulation was orally administered as 2 tablets (15 mg HB/650 mg APAP total dose) under 2 types of fed (high-fat and low-fat) and fasted conditions. Forty-eight subjects were enrolled and 40 subjects completed the study. Only subjects that completed all 3 study periods have been included in the PK evaluation.

Following a 10 hour overnight fast, subjects randomized to Treatment A consumed an entire standardized FDA high-fat breakfast (approximately 1,000±100 calories and approximately 50% from fat); those receiving Treatment B consumed an entire low-fat breakfast (approximately 800±80 calories and approximately 25% to 30% from fat). Breakfasts were consumed within 30 minutes prior to Hour 0 study drug administration. Subjects who could not consume the entire breakfast in the allotted time were dropped from the study. Subjects randomized to Treatment C were administered study drug under fasted conditions following an overnight fast of at least 10 hours. No food was allowed for the first 4 hours postdose. Blood samples were collected pre-dose (up to 60 minutes prior to dose), and at 15 min, 30 min, 45 min and 1, 2, 3, 4, 5, 6, 7, 8, 9, 10, 11, 12, 16, 18, 20, 24, 36 and 48 hours post-dose, and the resulting plasma samples were analyzed for Hydrocodone (HC) and APAP using a validated liquid chromatography-tandem mass spectrometry assay with a linear range of 0.100 to 50 ng/mL for HC and 100 to 15,000 ng/mL for APAP. The following PK parameters were calculated for hydrocodone and acetaminophen using standard non-compartmental methods:

- area under the plasma concentration curve to last quantifiable concentration $AUC_{(0-t)}$
- area under the plasma concentration curve to infinite time $AUC_{0-inf}$
- maximum observed plasma concentration ($C_{max}$)
- time observed maximum plasma concentration ($t_{max}$)
- lag time ($t_{lag}$)
- apparent first-order terminal elimination rate constant ($k_{el}$)
- apparent plasma terminal elimination half-life ($t_{1/2}$)

Tables 3 and 4 presents PK parameters for HO under the three treatment conditions, and FIG. 7 presents plasma HO concentration-time profiles for the treatments. Mean plasma concentration profiles of HO revealed that HO was rapidly absorbed under both fed (high and low fat meal) and fasted conditions. There was a slight lag (median 0.25 hours) when the formulation was administered after a low fat meal. The median of the time of observed maximum plasma concentrations ($T_{max}$) was 4 hours after administration under both the low fat and fasted conditions. Median $T_{max}$ for HO under high fat conditions was significantly delayed, as compared to fasted conditions (6 hr vs. 4 hr; P<0.05). Average maximum plasma HO concentrations ($C_{max}$) were 23.09 ng/mL after a low fat breakfast, 21.66 ng/mL after a high fat breakfast, and 20.33 ng/mL under fasted conditions.

TABLE 3

Hydrocodone Pharmacokinetic Estimates (2 tablets of 7.5/325)

| Parameter | Treatment A Fed (High Fat) Mean (SD) (N = 31) | Treatment B Fed (Low Fat) Mean (SD) (N = 31) | Treatment C Fasted Mean (SD) (N = 31) |
|---|---|---|---|
| $AUC_{0-t}$ (ng · hr/mL) | 301.50 (52.81) | 299.72 (57.01) | 280.10 (58.80) |
| $AUC_{0-inf}$ (ng · hr/mL) | 303.66 (53.13) | 301.95 (57.83) | 282.94 (59.86) |
| $C_{max}$ (ng/mL) | 21.66 (4.88) | 23.09 (3.79) | 20.33 (4.33) |
| $T_{max}$ (hr)[a] | 6 (2-11) | 4 (2-7) | 4 (2-7) |
| $K_{el}$ (1/hr) | 0.1273 (0.0207) | 0.1218 (0.0202) | 0.1110 (0.0194) |
| $t_{lag}$ (hr)[a] | 0 (0-1.07) | 0.25 (0-0.75) | 0 (0-0.50) |
| $t_{1/2}$ (hr) | 5.58 (0.85) | 5.85 (1.00) | 6.43 (1.11) |

[a]Median (minimum-maximum).

A comparison of $C_{max}$ showed that HC concentrations were 6% and 14% higher when the formulation was given under high fat (Treatment A) and low fat (Treatment B) conditions, compared to fasted conditions (Treatment C; see Table 3). The $C_{max}$ for Treatment A was bioequivalent to both Treatments B (88%-99%) and C (101%-113%) as the 90% CIs for the geometric ratios were contained within 80% to 125% (see Table 4). The $C_{max}$ observed for Treatment B was also bioequivalent to Treatment C (108%-122%). AUCs were approximately 7% higher when the formulation was administered under fed conditions (high and low fat), as compared to fasted conditions (Table 3). AUC for both Treatments A and B (high fat and low fat) were bioequivalent to Treatment C (fasted; 104%-112% and 103%-111% for AUC0-t and 104%-112% and 103%-111% for $AUC_{0-inf}$) (Table 4). The apparent plasma terminal elimination half-life ($t_{1/2}$) for HC was similar when the formulation was administered under fed (5.58 hours) and fasted conditions (6.43 hours).

TABLE 4

Hydrocodone Geometric LSMEANS Ratio (%) (90% CI)

| Parameter | Treatment A/C Fed (High Fat)/Fasted | Treatment B/C Fed (Low Fat)/Fasted | Treatment A/B Fed (High Fat)/ Fed (Low Fat) |
|---|---|---|---|
| $AUC_{0-t}$ (ng · hr/mL)[a] | 108.40 (104.44-112.51) | 107.45 (103.53-111.52) | 100.89 (97.22-104.69) |
| $AUC_{0-inf}$ (ng · hr/mL)[a] | 108.11 (104.14-112.24) | 107.17 (103.23-111.26) | 100.88 (97.19-104.72) |
| $C_{max}$ (ng/mL)[a] | 106.66 (100.54-113.15) | 114.75 (108.16-121.73) | 92.95 (87.64-98.59) |

[a]N = 40.

PK parameters for APAP are presented in Tables 5 and 6 and the plasma APAP concentration-time profiles are presented in FIG. 8. APAP was rapidly absorbed following administration under fed (high and low fat meals) and fasted conditions. There was a slight lag when the formulation was administered after a low fat breakfast (median lag time [$t_{lag}$] 0.25 hours). There was no lag in the absorption of APAP when administered following a high fast breakfast or after fasting. The time to $C_{max}$ was significantly (P<0.05) longer when administered after a meal (high and low fat; median $T_{max}$=2 hours) than when administered under fasted conditions (median $T_{max}$=0.75 hour). Average $C_{max}$ values for APAP were lower after a high (4.317 ng/mL) and low fat (4,122 ng/mL) meal than when administered under fasted conditions (5307 ng/mL). Geometric mean ratios for $C_{max}$ following Treatments A and B were 20% to 22% lower than for Treatment C (Table 6). The 90% CIs for $C_{max}$ following Treatment A (75%-88%) and Treatment B (73%-83%) with reference to fasted state were outside the bioequivalent range of 80%-125%. The AUCs for APAP were almost identical when the formulation was administered under high fat, low fat, or fasting conditions. Comparison of geometric mean ratios of $AUC_{0-t}$ and $AUC_{0\ inf}$ for Treatments A (90% CI 100%-105% and 98%-103%) and B (90% CI 96%-101% and 97% to 103%) with those for Treatment C showed that treatments were bioequivalent. The $t_{1/2}$ for APAP after the formulation was administered after a high or low fat meal (5 hours) was slightly shorter than when administered under fasted conditions (7 hours).

TABLE 5

APAP Pharmacokinetic Estimates (2 tablets of 7.5/325)

| Parameter | Treatment A Fed (High Fat) Mean (SD) (N = 31) | Treatment B Fed (Low Fat) Mean (SD) (N = 31) | Treatment C Fasted Mean (SD) (N = 31) |
|---|---|---|---|
| $AUC_{0-t}$ (ng · hr/mL) | 33210.39 (10402.75) | 32415.11 (9586.52) | 32149.34 (9431.97) |
| $AUC_{0-inf}$ (ng · hr/mL) | 34689.91 (10672.37) | 34092.21 (9949.21) | 34803.59 (9635.34) |
| $C_{max}$ (ng/mL) | 4317.00 (1185.08) | 4122.25 (877.19) | 5307.00 (1419.43) |
| $T_{max}$ (hr)$^a$ | 2 (0.25-6.05) | 2 (0.75-7.00) | 0.75 (0.25-5.00) |
| $K_{el}$ (1/hr) | 0.1444 (0.0470) | 0.1317 (0.0356) | 0.1072 (0.0402) |
| $t_{lag}$ (hr)$^a$ | 0 (0-0.63) | 0.25 (0-0.50) | 0.00 (0-0.25) |
| $t_{1/2}$ (hr) | 5.37 (2.02) | 5.68 (1.68) | 7.37 (2.77) |

$^a$Median (minimum-maximum).

TABLE 6

APAP Geometric LSMEANS Ratio (%) (90% CI)

| Parameter | Treatment A/C Fed (High Fat)/Fasted | Treatment B/C Fed (Low Fat)/Fasted | Treatment A/B Fed (High Fat)/Fed (Low Fat) |
|---|---|---|---|
| $AUC_{0-t}$ (ng · hr/mL)$^a$ | 102.70 (100.05-105.42) | 100.74 (98.15-103.41) | 101.94 (99.32-104.63) |
| $AUC_{0-inf}$ (ng · hr/mL)$^a$ | 100.32 (97.71-103.01) | 98.66 (96.09-101.30) | 101.69 (99.04-104.40) |
| $C_{max}$ (ng/mL)$^a$ | 80.49 (75.44-85.88) | 78.10 (73.20-83.33) | 103.06 (96.62-109.93) |

$^a$N = 40.

In summary, total exposure (AUC) for HC was slightly increased (by about 7%) when the formulation was administered with food (after high- or low-fat meal); however, AUCs for HC were equivalent between all treatments (high fat vs. fasted, low fat vs. fasted and high fat vs. low fat). Peak exposure ($C_{max}$) for HC was 6% and 14% higher under high fat and low-fat conditions, respectively, compared to fasted conditions. The $C_{max}$ for HC after a high-fat meal and low fat meal were bioequivalent to fasted conditions. The AUCs for APAP were equivalent between all treatments (high fat vs. fasted, low fat vs. fasted, and high fat vs. low fat). The peak exposure ($C_{max}$) for APAP was decreased by about 20% in fed (high- and low-fat) states as compared to the fasted state.

Example 3

Clinical Pharmacokinetic Analysis of an Extended Release Formulation of 7.5 mg Hydrocodone/325 mg Acetaminophen—Single and Multiple Doses An open-label, randomized, 3-period crossover study was performed to evaluate single and multiple dose pharmacokinetics, bioavailability, and safety of an extended release formulation containing 7.5 mg hydrocodone/325 mg acetaminophen under fasted conditions in normal, healthy subjects. (See example in Chart 1). The pharmacokinetics (PK) and bioavailability following administration of a 7.5 mg hydrocodone/325 mg acetaminophen tablet disclosed herein administered as either 1 or 2 tablets every 12 hours was compared to 1 immediate release tablet containing 7.5 mg hydrocodone/325 mg acetaminophen and administered every 6 hours (Q6 h). The study also assessed the PK proportionality between the 1 tablet and 2 tablet dosing configurations of the 7.5 mg hydrocodone/325 mg acetaminophen tablet disclosed herein. In addition, the study evaluated the safety of the 1 tablet and 2 tablet dosing configurations of the 7.5 mg hydrocodone/325 mg acetaminophen tablet disclosed herein compared with immediate release tablet containing 7.5 mg hydrocodone/325 mg acetaminophen.

The subjects were randomly divided into three treatment options:

Treatment A: One tablet of the 7.5 mg hydrocodone/325 mg acetaminophen tablet disclosed herein administered orally under fasted conditions on Day 1 followed by 1 tablet given Q12 h (beginning on Day 3 for a total of 9 doses).

Treatment B: Two tablets of the 7.5 mg hydrocodone/325 mg acetaminophen tablet disclosed herein administered orally under fasted conditions on Day 1 followed by 2 tablets given Q12 h (beginning on Day 3 for a total of 9 doses).

Treatment C: One tablet of an immediate release tablet containing 7.5 mg hydrocodone/325 mg acetaminophen administered orally Q6 h for 2 doses under fasted conditions on Day 1 followed by 1 tablet given Q6 h (beginning on Day 3 for a total of 18 doses).

The pharmacokinetic (PK) parameters of a single dose of hydrocodone and acetaminophen are presented below in Tables 7 and 8 respectively. The plasma concentrations of hydrocodone and acetaminophen are presented in FIGS. 9 and 10, respectively. The pharmacokinetic parameters demonstrate that the formulations disclosed herein containing 7.5 mg hydrocodone/325 mg acetaminophen are dose proportional for both hydrocodone and acetaminophen. The pharmacokinetic profiles for hydrocodone showed an initial rapid rise in the concentrations of hydrocodone to provide a subject with the desired early onset of action (the median $t_{lag}$ for the formulation disclosed herein is 0.08 hour and for the immediate release tablet it is 0.04 hour). The hydrocodone concentrations in the subjects that took the formulations disclosed herein containing 7.5 mg hydrocodone/325 mg acetaminophen also fell slowly over a period of 12 hours.

Similarly, the pharmacokinetic profiles for acetaminophen showed an initial rapid rise in the concentrations of acetaminophen to provide the desired early onset of action (the median $t_{lag}$=0 hr for the formulation disclosed herein containing 7.5 mg hydrocodone/325 mg acetaminophen, which is the same as the immediate release tablet containing 7.5 mg hydrocodone/325 mg acetaminophen). The acetaminophen concentrations achieved by the formulation disclosed herein containing 7.5 mg hydrocodone/325 mg acetaminophen fell slowly, reaching levels that were lower than the immediate release tablet at around 12 hours, showing the desired "time off" from acetaminophen.

TABLE 7

Single Dose PK Parameters for Hydrocodone (Mean ± SD)

| PK Parameters | One Tablet (7.5 HC/ 325 APAP) Treatment A | Two Tablets (7.5 HC/325 APAP) Treatment B | Commercially-available immediate release product (7.5 HC/325 APAP) Treatment C |
|---|---|---|---|
| $C_{max}$ (ng/mL) | 8.98 (2.02) | 17.53 (3.69) | 24.48 (5.69) |
| $AUC_t$ (ng · hr/mL) | 122.43 (30.53) | 248.48 (63.22) | 254.39 (63.21) |
| $AUC_{inf}$ (ng · hr/mL) | 124.24 (30.63) | 251.20 (63.57) | 256.24 (63.71) |
| $t_{lag}$ (hr) | 0.12 (0.14) | 0.08 (0.13) | 0.04 (0.09) |
| $T_{max}$* (hr) | 8.00 (0.25-6.00) | 3.00 (0.25-2.00) | 3.00 (0.25-8.00) |
| $T_{1/2}$ (hr) | 6.26 (1.41) | 6.41 (1.09) | 5.37 (0.83) |

*Tmax values: median (range)

TABLE 8

Single Dose PK Parameters for Acetaminophen (Mean ± SD)

| PK Parameters | One Tablet (7.5 HC/ 325 APAP) Treatment A | Two Tablets (7.5 HC/ 325 APAP) Treatment B | Commercially-available immediate release product (7.5 HC/325 APAP) Treatment C |
|---|---|---|---|
| $C_{max}$ (ng/mL) | 2604.55 (925.57) | 5432.05 (1793.44) | 4912.05 (1647.69) |
| $AUC_t$ (ng · hr/mL) | 13248.82 (3889.65) | 28593.91 (8400.40) | 27928.74 (9086.86) |
| $AUC_{inf}$ (ng · hr/mL) | 15124.65 (4179.45) | 31049.83 (8899.91) | 28993.63 (9243.85) |
| $t_{lag}$ (hr) | 0.06 (0.11) | 0.02 (0.07) | 0.01 (0.04) |
| $T_{max}$* (hr) | 0.50 (0.25-6.00) | 0.50 (0.25-2.00) | 0.50 (0.25-8.00) |
| $T_{1/2}$ (hr) | 7.73 (2.88) | 8.32 (4.34) | 4.29 (1.40) |

*Tmax values: median (range)

As shown below in Table 9, the 90% Confidence Intervals for all the pharmacokinetic parameters for hydrocodone dosed as a single dose of either one tablet or two tablets of the formulations disclosed herein containing 7.5 mg hydrocodone/325 mg acetaminophen were contained within the 80-125% bioequivalence range for the immediate release tablet containing 7.5 mg hydrocodone/325 mg acetaminophen. Similarly, as shown below in Table 10, the 90% Confidence Intervals for all the pharmacokinetic parameters for acetaminophen dosed as a single dose of either one tablet or two tablets of the formulations disclosed herein containing 7.5 mg hydrocodone/325 mg acetaminophen were contained within the 80-125% bioequivalence range for the immediate release tablet containing 7.5 mg hydrocodone/325 mg acetaminophen. However, the cmax values for both dosing configurations for the formulations disclosed herein were lower as compared to the immediate release product.

TABLE 9

Single Dose Bioequivalence Parameters for Hydrocodone

| | | Immediate Release Tablet | | |
|---|---|---|---|---|
| Test | PK Parameter | LSM | 90% CI Lower | Upper |
| One Tablet | $C_{max}$ | 73.53 | 70.46 | 76.74 |
| | $AUC_t$ | 96.2 | 92.33 | 100.23 |
| | $AUC_{inf}$ | 96.97 | 93.10 | 100.99 |
| Two Tablets | $C_{max}$ | 71.86 | 68.85 | 74.99 |
| | $AUC_t$ | 97.59 | 93.66 | 101.68 |
| | $AUC_{inf}$ | 97.96 | 94.06 | 102.03 |
| | Reference: Two tablets of the 7.5 mg HC/325 mg APAP | | | |
| One Tablet | $C_{max}$ | 102.33 | 98.05 | 106.80 |
| | $AUC_t$ | 98.58 | 94.61 | 102.71 |
| | $AUC_{inf}$ | 98.98 | 95.04 | 103.09 |

TABLE 10

Single Dose Bioequivalence Parameters for Acetaminophen

| | | Immediate Release Tablet | | |
|---|---|---|---|---|
| Test | PK Parameter | LSM | 90% CI Lower | Upper |
| One Tablet | $C_{max}$ | 105.34 | 97.98 | 113.25 |
| | $AUC_t$ | 95.16 | 91.89 | 98.55 |
| | $AUC_{inf}$ | 104.99 | 101.17 | 108.95 |
| Two Tablets | $C_{max}$ | 110.78 | 103.04 | 119.10 |
| | $AUC_t$ | 102.62 | 99.10 | 106.28 |
| | $AUC_{inf}$ | 107.42 | 103.52 | 111.48 |
| | Reference: Two tablets of the 7.5 mg HC/325 mg APAP | | | |
| One Tablet | $C_{max}$ | 95.09 | 88.45 | 102.24 |
| | $AUC_t$ | 92.73 | 89.54 | 96.03 |
| | $AUC_{inf}$ | 97.73 | 94.18 | 101.42 |

The pharmacokinetic (PK) parameters of multiple doses of hydrocodone and acetaminophen are presented below in Tables 11 and 12, respectively. The plasma concentrations of hydrocodone and acetaminophen are presented in FIGS. 11 and 12, respectively. The pharmacokinetic parameters demonstrate that the formulations disclosed herein containing 7.5 mg hydrocodone/325 mg acetaminophen are dose proportional for both hydrocodone and acetaminophen. No differences were observed in dose-normalized $C_{max}^{ss}$, $C_{min}^{ss}$, $AUC_{0-12}^{ss}$hr, $C_{av}^{ss}$, and fluctuation of hydrocodone and acetaminophen following administration of the formulation disclosed herein containing 7.5 mg hydrocodone/325 mg acetaminophen as either 1-tablet or 2-tablet dosing configurations, or the immediate release tablet containing 7.5 mg hydrocodone/325 mg acetaminophen. For acetaminophen, the 1-tablet, 2-tablet and immediate release tablet had the same (0.5 hr) median $T_{max}^{ss}$. For hydrocodone, the median $T_{max}$ss of the formulation disclosed herein containing 7.5 mg hydrocodone/325 mg acetaminophen (dosed as either 1 and 2 tablets) was 2 hours while the median $T_{max}$ss for the immediate release tablet containing 7.5 mg hydrocodone/325 mg acetaminophen was 1 hour. No difference was observed in the swing of hydrocodone for the formulation disclosed herein containing 7.5 mg hydrocodone/325 mg acetaminophen dosed as either 1 and 2-tablet and the immediate release tablet containing 7.5 mg hydrocodone/325 mg acetaminophen. In the case of acetaminophen, the swing was partially out of the range to demonstrate no difference (107.33-132.50).

TABLE 11

Multiple Dose PK Parameters for Hydrocodone (Mean ± SD)

| PK Parameters | One Tablet (7.5 HC/ 325 APAP) Treatment A | Two Tablets (7.5 HC/ 325 APAP) Treatment B | Commercially-available immediate release product (7.5 HC/325 APAP) Treatment C |
|---|---|---|---|
| $C_{max}$ (ss) (ng/mL) | 15.57 (3.85) | 30.54 (6.87) | 33.80 (8.74) |
| $C_{min}$ (ss) (ng/mL) | 6.49 (2.41) | 13.38 (4.12) | 14.13 (4.67) |
| $C_{avg}$ (ss) (ng/mL) | 11.20 (3.16) | 22.54 (5.36) | 22.38 (5.82) |
| $AUC_{0-12}$ (ss) (ng · hr/mL) | 134.36 (37.91) | 270.52 (64.29) | 268.57 (69.87) |
| $T_{max}$ (SS) (hr) | 146.00 (144.50-150.00) | 146.00 (144.50-150.00) | 145.00 (144.50-142.00) |
| Swing | 1.53 (1.00) | 1.37 (1.42) | 1.53 (3.16) |
| Fluctuation (%) | 83.76 (19.00) | 77.54 (16.70) | 90.60 (3054) |
| Accumulation Index | 1.43 (0.20) | 1.43 (0.20) | 1.23 (0.29) |

* Tmax values: median (range)

TABLE 12

Multiple Dose PK Parameters for Acetaminophen (Mean ± SD)

| PK Parameters | One Tablet (7.5 HC/ 325 APAP) Treatment A | Two Tablets (7.5 HC/ 325 APAP) Treatment B | Commercially-available immediate release product (7.5 HC/325 APAP) Treatment C |
|---|---|---|---|
| $C_{min}$ (ss) (ng/mL) | 464.89 (166.72) | 844.68 (293.41) | 893.86 (310.09) |
| $C_{avg}$ (ss) (ng/mL) | 1169.43 (316.86) | 2238.75 (577.32) | 2267.63 (592.95) |
| $AUC_{0-12}$ (ss) (ng · hr/mL) | 14033.21 (3802.32) | 26864.94 (6927.89) | 27211.55 (7115.37) |
| $T_{max}$ (SS) (hr) | 144.5 (144.25-148.00) | 144.5 (144.25-146.00) | 144.5 (144.25-152.00) |
| Swing | 6.43 (0.96) | 6.78 (0.44) | 5.76 (2.80) |
| Fluctuation (%) | 237.58 (85.70) | 237.66 (74.05) | 211.43 (76.05) |
| Accumulation Index | 1.28 (0.21) | 1.21 (0.17) | 1.05 (0.06) |

* Tmax values: median (range)

As shown below in Table 13, the 90% Confidence Intervals for all the pharmacokinetic parameters for hydrocodone dosed as multiple doses of either one tablet or two tablets of the formulations disclosed herein containing 7.5 mg hydrocodone/325 mg acetaminophen were contained within the 80-125% bioequivalence range for the immediate release tablet containing 7.5 mg hydrocodone/325 mg acetaminophen. Similarly, as shown below in Table 14, the 90% Confidence Intervals for all the pharmacokinetic parameters (except the swing) for acetaminophen dosed as multiple doses of either one tablet or two tablets of the formulations disclosed herein containing 7.5 mg hydrocodone/325 mg acetaminophen were contained within the 80-125% bioequivalence range for the immediate release tablet containing 7.5 mg hydrocodone/325 mg acetaminophen.

TABLE 13

Multiple Dose Bioequivalence Parameters for Hydrocodone

| | | Immediate Release Tablet | | |
|---|---|---|---|---|
| | | | 90% CI | |
| Test | PK Parameter | LSM | Lower | Upper |
| One Tablet | $C_{max}$ (ss) | 92.46 | 89.07 | 95.98 |
| | $C_{min}$ (ss) | 91.22 | 87.61 | 94.98 |
| | $C_{avg}$ (ss) | 99.7 | 96.85 | 102.64 |
| | $AUC_{0-12}$ (ss) | 99.71 | 96.85 | 102.65 |
| | Swing | 103.98 | 97.05 | 111.4 |
| | Fluctuation | 95.13 | 90.54 | 99.94 |
| Two Tablets | $C_{max}$ (ss) | 90.91 | 87.58 | 94.38 |
| | $C_{min}$ (ss) | 95.33 | 91.56 | 99.26 |
| | $C_{avg}$ (ss) | 101.15 | 98.25 | 104.14 |
| | $AUC_{0-12}$ (ss) | 101.15 | 98.26 | 104.14 |
| | Swing | 93.88 | 87.62 | 100.58 |
| | Fluctuation | 88.47 | 84.21 | 92.95 |
| | Reference: Two tablets of the 7.5 mg HC/325 mg APAP | | | |
| One Tablet | $C_{max}$ (ss) | 101.7 | 97.97 | 105.57 |
| | $C_{min}$ (ss) | 95.69 | 91.9 | 99.64 |
| | $C_{avg}$ (ss) | 98.57 | 95.74 | 101.48 |
| | $AUC_{0-12}$ (ss) | 98.57 | 95.75 | 101.48 |
| | Swing | 110.76 | 103.38 | 118.66 |
| | Fluctuation | 107.52 | 102.34 | 112.96 |

TABLE 14

Multiple Dose Bioequivalence Parameters for Acetaminophen

| | | Immediate Release Tablet | | |
|---|---|---|---|---|
| | | | 90% CI | |
| Test | PK Parameter | LSM | Lower | Upper |
| One Tablet | $C_{max}$ (ss) | 113.39 | 105.69 | 121.66 |
| | $C_{min}$ (ss) | 102.92 | 98.12 | 107.95 |
| | $C_{avg}$ (ss) | 102.81 | 100.19 | 105.49 |
| | $AUC_{0-12}$ (ss) | 102.81 | 100.19 | 105.49 |
| | Swing | 112.44 | 101.2 | 124.93 |
| | Fluctuation | 112.56 | 103.72 | 122.17 |
| Two Tablets | $C_{max}$ (ss) | 109.25 | 101.83 | 117.21 |
| | $C_{min}$ (ss) | 94.27 | 89.87 | 98.88 |
| | $C_{avg}$ (ss) | 98.76 | 96.25 | 101.33 |
| | $AUC_{0-12}$ (ss) | 98.76 | 96.25 | 101.33 |
| | Swing | 119.25 | 107.33 | 132.5 |
| | Fluctuation | 113.83 | 104.88 | 123.54 |
| | Reference: Two tablets of the 7.5 mg HC/325 mg APAP | | | |
| One Tablet | $C_{max}$ (ss) | 103.79 | 96.74 | 111.36 |
| | $C_{min}$ (ss) | 109.17 | 104.08 | 114.51 |
| | $C_{avg}$ (ss) | 104.1 | 101.45 | 106.82 |
| | $AUC_{0-12}$ (ss) | 104.1 | 101.45 | 106.82 |
| | Swing | 94.29 | 84.86 | 104.76 |
| | Fluctuation | 98.89 | 91.11 | 107.32 |

Example 4

Partial Areas Under the Curve for Hydrocodone and Acetaminophen

A cross-study comparison of the partial AUCs for acetaminophen following oral administration of the pharmaceutical compositions described in Treatment A of Example 1, and Treatment C of Example 2 was performed. These results are summarized in Tables 15 and 16. Additionally, the partial AUCs for hydrocodone were determined and are summarized in Tables 17.

TABLE 15

Mean (SD) Parameter Estimates for Partial AUCs for Acetaminophen.

| Study | $AUC_{0-1\ h}$ | $AUC_{1-12\ h}$ | $AUC_{12-36\ h}$ | $AUC_{0-1.27\ h}$ | $AUC_{1.27-36\ h}$ | $AUC_{0-t}$ |
|---|---|---|---|---|---|---|
| Treatment A (Ex. 16) | 3276.62 | 20624.53 | 7774.64 | 3816.89 | 27858.88 | 30618.62 |
| Treatment C (Ex. 17) | 3264.68 | 22299.56 | 8284.15 | 4428.19 | 20420.21 | 32441.45 |

TABLE 16

Percent of the partial AUC compared to $AUC_{0-t}$.

| Study | $AUC_{1-12\ h}$ | $AUC_{12-36\ h}$ |
|---|---|---|
| Treatment A (Ex. 16) | 67% | 25% |
| Treatment C (Ex. 17) | 69% | 26% |

TABLE 17

Mean (SD) Parameter Estimates for Partial AUCs for Hydrocodone.

| Study | $AUC_{0-t}$ (ng · h/mL) | $AUC_{0-2.44\ h}$ (ng · h/mL) | $AUC_{2.44-36\ h}$ (ng · h/mL) |
|---|---|---|---|
| Treatment A (Ex. 16) | 254.16 (71.57) | 26.33 (8.70) | 227.93 (65.32) |
| Treatment C (Ex. 17) | 280.08 (59.58) | 27.41 (9.34) | 246.25 (52.99) |

Further, it was determined that Tmax for an immediate release tablet containing 7.5 mg hydrocodone and 325 mg acetaminophen plus two standard deviations was about 3 hr. Some of the partial AUCs of the pharmaceutical formulation described herein were determined in accordance with this time interval.

The bioequivalence determinations between two tablets of a pharmaceutical composition described herein, each containing 7.5 mg hydrocodone and 325 mg acetaminophen (in fed and fasted states) and an immediate release tablet containing 7.5 mg hydrocodone and 325 mg acetaminophen can be found in Tables 18 and 19.

TABLE 18

Bioequivalence Determination for Acetaminophen

| Parameter | LSM Ratio | 90% CI Lower | 90% CI Upper |
|---|---|---|---|
| Ln ($AUC_{0-1.27\ h}$) | 103.62 | 87.18 | 123.16 |
| Ln ($AUC_{1.27-36\ h}$) | 93.32 | 83.11 | 104.78 |
| Ln ($AUC_{0-t}$) | 94.52 | 84.34 | 105.93 |

TABLE 19

Bioequivalence Determination for Hydrocodone

| Parameter | LSM Ratio | 90% CI Lower | 90% CI Upper |
|---|---|---|---|
| Ln ($AUC_{0-2.44\ h}$) | 91.49 | 82.77 | 101.13 |
| Ln ($AUC_{2.44-36\ h}$) | 96.78 | 83.19 | 112.61 |
| Ln ($AUC_{0-t}$) | 89.71 | 81.51 | 98.74 |

Example 5

In vitro Dissolution of Controlled-Release Bilayer Tablets Comprising 7.5 mg Hydrocodone and 325 mg Acetaminophen Performed at a 100 rpm Paddle Speed Three batches of bilayer formulations described herein were prepared, each containing a total of 7.5 mg of hydrocodone bitartrate and a total of 325 mg of acetaminophen. 50% of the acetaminophen was contained in the immediate release portion, and the other 50% was contained in the ER layer. 25% of the hydrocodone bitartrate was contained in the immediate release portion of the formulation, and the other 75% was contained in the ER layer. POLYOX® N-60K was employed as the extended release component in an amount of 45% by weight of the ER portion.

Dissolution profiles for the formulations of each batch were determined in a USP Type II apparatus. Six tablets from each batch were weighed, placed in a sinker, and dropped into an equilibrated dissolution bath vessel containing 900 mL of (helium sparged) 0.1 N HCl heated to 37° C.±0.5° C. The mixture was stirred at 100±4 rpm, and the temperature was maintained at 37° C.±0.5° C. for 12 hr. The bath vessel was covered with a low evaporation vessel cover. Samples (5 mL) were removed at 0.25 hr, 0.5 hr, 1 hr, 2 hr, 4 hr, 6, hr, 8 hr, and 12 hr. Each sample was filtered through a 0.45 μm filter and analyzed by HPLC using standard procedures.

The cumulative percent release of acetaminophen and hydrocodone from each batch are described in Table 20.

TABLE 20

Release rate data of bilayer tablets
(7.5 mg hydrocodone bitartrate; 325 mg
acetaminophen) using a 100 rpm dissolution method.

| | Hydrocodone Bitartrate | | | | Acetaminophen | | | |
|---|---|---|---|---|---|---|---|---|
| Time (Hours) | Mean (%) | RSD | Min (%) | Max (%) | Mean (%) | RSD | Min (%) | Max (%) |
| Batch 1 | | | | | | | | |
| 0.25 | 31.4 | 6.3 | 27.1 | 33.6 | 52.7 | 5.1 | 46.7 | 54.6 |
| 0.5 | 36.5 | 3.6 | 34.1 | 38.6 | 55.5 | 2.5 | 52.2 | 56.8 |
| 1.0 | 43.7 | 2.1 | 42.2 | 45.2 | 59.1 | 1.4 | 57.3 | 60.1 |
| 2.0 | 54.5 | 1.7 | 53.0 | 56.6 | 64.7 | 0.9 | 63.8 | 65.8 |
| 4.0 | 70.9 | 1.3 | 69.4 | 72.9 | 74.0 | 0.8 | 73.1 | 75.2 |
| 6.0 | 83.0 | 1.5 | 81.1 | 85.3 | 81.8 | 0.9 | 80.6 | 83.3 |
| 8.0 | 91.9 | 1.5 | 89.7 | 93.8 | 88.4 | 0.9 | 87.4 | 89.9 |
| 12.0 | 100.5 | 1.4 | 98.1 | 102.5 | 96.1 | 0.8 | 94.9 | 97.2 |
| Batch 2 | | | | | | | | |
| 0.25 | 30.8 | 3.0 | 29.6 | 32.5 | 53.6 | 1.7 | 52.4 | 55.1 |
| 0.5 | 35.6 | 2.1 | 34.5 | 37.0 | 55.8 | 1.4 | 54.9 | 57.1 |
| 1.0 | 42.4 | 2.3 | 40.7 | 44.5 | 59.1 | 1.3 | 58.4 | 60.6 |
| 2.0 | 52.7 | 2.1 | 51.6 | 54.8 | 64.6 | 1.3 | 63.9 | 66.5 |
| 4.0 | 69.0 | 2.0 | 67.4 | 71.5 | 73.9 | 1.3 | 72.8 | 76.2 |
| 6.0 | 81.8 | 1.7 | 79.5 | 83.5 | 82.4 | 1.4 | 80.9 | 85.1 |
| 8.0 | 90.3 | 1.5 | 87.9 | 92.5 | 88.6 | 1.6 | 86.6 | 91.9 |
| 12.0 | 98.9 | 1.6 | 96.0 | 101.0 | 96.5 | 1.5 | 94.4 | 99.8 |
| Batch 3 | | | | | | | | |
| 0.25 | 31.7 | 3.2 | 29.7 | 33.6 | 52.7 | 2.5 | 49.9 | 54.9 |
| 0.5 | 36.4 | 2.8 | 34.7 | 38.2 | 55.1 | 2.0 | 53.1 | 56.9 |
| 1.0 | 43.5 | 2.3 | 42.1 | 45.1 | 58.7 | 1.8 | 57.5 | 60.7 |

TABLE 20-continued

Release rate data of bilayer tablets
(7.5 mg hydrocodone bitartrate; 325 mg
acetaminophen) using a 100 rpm dissolution method.

| | Hydrocodone Bitartrate | | | | Acetaminophen | | | |
|---|---|---|---|---|---|---|---|---|
| Time (Hours) | Mean (%) | RSD | Min (%) | Max (%) | Mean (%) | RSD | Min (%) | Max (%) |
| 2.0 | 54.5 | 2.4 | 52.9 | 56.5 | 64.5 | 1.7 | 63.3 | 66.8 |
| 4.0 | 70.2 | 2.5 | 68.2 | 72.7 | 73.7 | 1.7 | 72.1 | 76.4 |
| 6.0 | 81.8 | 2.2 | 79.8 | 85.6 | 81.3 | 1.6 | 79.2 | 84.3 |
| 8.0 | 90.5 | 2.3 | 88.0 | 95.1 | 87.8 | 1.6 | 85.5 | 91.0 |
| 12.0 | 98.9 | 1.9 | 97.1 | 103.0 | 95.2 | 1.4 | 92.9 | 98.2 |

Example 6

In vitro Dissolution of Controlled-Release Bilayer Tablets Comprising 7.5 mg Hydrocodone and 325 mg Acetaminophen Performed at a 150 rpm Paddle Speed Dissolution studies were performed on fast-release, medium-release, and slow-release pharmaceutical formulations described herein containing 7.5 mg hydrocodone and 325 mg acetaminophen.

Dissolution profiles for the three above-described compositions were determined in USP Type II apparatus. Six tablets of each composition were weighed, placed in a sinker, and dropped into an equilibrated dissolution bath vessel that contained 900 mL of (helium sparged) 0.1 N HCl that was heated to 37° C.±0.5° C. The mixture was stirred at 150±6 rpm and the temperature was maintained at 37° C.±0.5° C. for 12 hr. The bath vessel was covered with a low evaporation vessel cover. Samples (5 mL) were removed at 0.25, 0.5, 1, 2, 4, 6, 8, and 12 hours. Each sample was filtered through a 0.45 μm filter and analyzed by HPLC using standard procedures.

The results of these dissolution studies are summarized in Table 21 and FIGS. 13 and 14.

TABLE 21

Mean acetaminophen and hydrocodone dissolution data.

| | Fast (%) (RSD) | | Medium (%) (RSD) | | Slow (%) (RSD) | |
|---|---|---|---|---|---|---|
| Time (hr) | APAP | Hydrocodone | APAP | Hydrocodone | APAP | Hydrocodone |
| 0.08 | 52.6 (2.2) | 26.3 (4.1) | 52.4 (2.7) | 28.4 (4.3) | 52.2 (2.1) | 28.8 (4.0) |
| 0.25 | 55.8 (2.0) | 34.3 (2.1) | 54.4 (2.7) | 33.4 (2.9) | 54.2 (1.7) | 33.8 (2.8) |
| 0.5 | 58.9 (1.9) | 41.2 (1.4) | 56.9 (2.5) | 38.6 (2.4) | 56.2 (1.5) | 38.2 (3.3) |
| 1.0 | 64.0 (1.8) | 51.1 (1.4) | 60.9 (2.3) | 46.8 (1.9) | 59.5 (1.5) | 45.2 (3.5) |
| 2.0 | 72.8 (1.6) | 65.9 (2.0) | 67.9 (2.0) | 59.7 (2.1) | 65.0 (1.4) | 56.3 (3.5) |
| 4.0 | 87.0 (1.8) | 86.7 (2.6) | 79.8 (1.6) | 79.6 (2.1) | 74.6 (1.4) | 74.0 (2.6) |
| 8.0 | 98.5 (1.1) | 100.7 (1.2) | 93.9 (1.0) | 99.7 (1.9) | 88.2 (1.4) | 94.9 (2.4) |
| 12.0 | 97.9 (1.2) | 100.5 (1.5) | 96.9 (0.8) | 102.9 (1.6) | 95.6 (1.7) | 103.0 (2.4) |
| 18.0 | 96.8 (1.2) | 100.3 (1.6) | 96.1 (0.8) | 102.8 (1.7) | 97.0 (1.5) | 104.6 (2.1) |

Example 7

Varying Polyox Grades Comprising 25% by Weight of the Extended Release Portion of Bilayer Formulations Containing Hydrocodone Bilayer formulations described herein were prepared, each containing a total of 15 mg of hydrocodone bitartrate and a total of 500 mg of acetaminophen. 50% of the acetaminophen was contained in the immediate release portion, and the other 50% was contained in the ER layer. 25% of the hydrocodone bitartrate was contained in the immediate release portion of the formulation, and the other 75% was contained in the ER layer. In a first formulation, POLYOX® 205 was employed as the extended release component in an amount of 25% by weight of the ER portion. In a second formulation, POLYOX® 1105 was employed as the extended release component in an amount of 25% by weight of the ER portion. In a third formulation, POLYOX® N-12K was employed as the extended release component in an amount of 25% by weight of the ER portion. In a fourth formulation, POLYOX® N-60K was employed as the extended release component in an amount of 25% by weight of the ER portion. In a fifth formulation, POLYOX® 301 was employed as the extended release component in an amount of 25% by weight of the ER portion. The other excipients in the extended release portion were microcrystalline cellulose, spress B825, citric acid anhydrous, EDTA, hydroxypropyl cellulose, silicon dioxide, and magnesium stearate.

Dissolution profiles for the five above-described compositions were determined in a USP Type II apparatus. Five tablets of each composition were weighed, placed in a sinker, and dropped into an equilibrated dissolution bath vessel containing 900 mL of (helium sparged) 0.1 N HCl heated to 37° C.±0.5° C. The mixture was stirred at 150±6 rpm, and the temperature was maintained at 37° C.±0.5° C. for 12 hr. The bath vessel was covered with a low evaporation vessel cover. Samples (5 mL) were removed at 0.25 hr, 0.5 hr, 1 hr, 2 hr, 4 hr, 6, hr, 8 hr, 12 hr, and 18 hr. Each sample was filtered through a 0.45 μm filter and analyzed by HPLC using standard procedures.

The cumulative release profiles of acetaminophen and hydrocodone from these compositions are shown in FIGS. 15 and 16, respectively. These figures demonstrate that as the average molecular weight of the POLYOX® extended release component increases, the rate of dissolution at each time point decreases. For example, the formulations containing POLYOX® 205, 1105, N-12K, N-60K, and 301 had released about 59%, about 58%, about 56%, about 55%, and about 52% acetaminophen after 15 minutes, respectively; about 62%, about 61%, about 58%, about 57%, and about 56% acetaminophen after 30 minutes, respectively; about 68%, about 66%, about 63%, about 61%, and about 60% acetaminophen after 1 hr, respectively; about 78%, about 76%, about 71%, about 67%, and about 65% acetaminophen after 2 hr, respectively; about 92%, about 90%, about 83%, about 76%, and about 73% acetaminophen after 4 hr, respectively; about 98%, about 97%, about 92%, about 84%, and about 79% acetaminophen after 6 hr, respectively; about 99%, about 98%, about 96%, about 90%, and about 85% acetaminophen after 8 hr, respectively; about 98%, about 97%, about 96%, about 97%, and about 92% acetaminophen after 12 hr, respectively; and about 98%, about 97%, about 96%, about 97%, and about 97% acetaminophen after 18 hr, respectively.

A decreased release rate with a higher molecular weight POLYOX® grade was observed for the hydrocodone bitratrate. For example, the formulations containing POLYOX® 205, 1105, N-12K, N-60K, and 301 had released about 38%, about 39%, about 39%, about 34%, and about 32% hydrocodone bitratrate after 15 minutes, respectively; about 48%, about 47%, about 46%, about 41%, and about 39% hydrocodone bitratrate after 30 minutes, respectively; about 60%, about 57%, about 55%, about 49%, and about 47% hydrocodone bitratrate after 1 hr, respectively; about 76%, about 72%, about 68%, about 60%, and about 58% hydrocodone bitratrate after 2 hr, respectively; about 96%, about 93%, about 87%, about 77%, and about 73% hydrocodone bitratrate after 4 hr, respectively; about 105%, about 102%, about 99%, about 89%, and about 83% hydrocodone bitratrate after 6 hr, respectively; about 105%, about 102%, about 103%, about 97%, and about 91% hydrocodone bitratrate after 8 hr, respectively; about 105%, about 102%, 103%, about 104%, and about 100% hydrocodone bitratrate after 12 hr, respectively; and about 106%, about 103%, about 104%, about 104%, and about 104% hydrocodone bitratrate after 18 hr, respectively.

Example 8

Varying Polyox Grades Comprising 45% by Weight of the Extended Release Portion of Bilayer Formulations Containing Hydrocodone The release rate studies described in Example 7 were repeated, except that the five bilayer formulations were prepared such that they included POLYOX® 205, 1105, N-12K, N-60K, and 301 in an amount of 45% by weight of the ER portion.

The cumulative release profiles of acetaminophen and hydrocodone from these compositions are shown in FIGS. 17 and 18, respectively. Consistent with the results of Example 7, the rate of dissolution at each time point generally decreases as the average molecular weight of POLYOX® increases. For example, the formulations containing POLYOX® 205, 1105, N-12K, N-60K, and 301 had released about 55%, about 53%, about 55%, about 54%, and about 54% acetaminophen after 15 minutes, respectively; about 57%, about 56%, about 57%, about 55%, and about 56% acetaminophen after 30 minutes, respectively; about 62%, about 60%, about 60%, about 58%, and about 59% acetaminophen after 1 hr, respectively; about 70%, about 68%, about 67%, about 64%, and about 63% acetaminophen after 2 hr, respectively; about 84%, about 81%, about 78%, about 72%, and about 70% acetaminophen after 4 hr, respectively; about 95%, about 91%, about 87%, about 80%, and about 77% acetaminophen after 6 hr, respectively; about 99%, about 96%, about 93%, about 86%, and about 82% acetaminophen after 8 hr, respectively; about 99%, about 98%, about 99%, about 95%, and about 90% acetaminophen after 12 hr, respectively; and about 98%, about 97%, about 98%, about 99%, and about 96% acetaminophen after 18 hr, respectively.

A decreased release rate with a higher molecular weight POLYOX® grade was observed for the hydrocodone bitratrate. For example, the formulations containing POLYOX® 205, 1105, N-12K, N-60K, and 301 had released about 33%, about 33%, about 32%, about 31%, and about 32% hydrocodone bitratrate after 15 minutes, respectively; about 39%, about 39%, about 38%, about 36%, and about 37% hydrocodone bitratrate after 30 minutes, respectively; about 48%, about 48%, about 46%, about 43%, and about 43% hydrocodone bitratrate after 1 hr, respectively; about 63%, about 63%, about 59%, about 54%, and about 53% hydrocodone bitratrate after 2 hr, respectively; about 85%, about 84%, about 79%, about 71%, and about 68% hydrocodone bitratrate after 4 hr, respectively; about 99%, about 97%, about 92%, about 84%, and about 79% hydrocodone bitratrate after 6 hr, respectively; about 102%, about 103%, about 100%, about 93%, and about 88% hydrocodone bitratrate after 8 hr, respectively; about 103%, about 104%, about 104%, about 102%, and about 98% hydrocodone bitratrate after 12 hr, respectively; and about 104%, about 103%, about 104%, about 105%, and about 103% hydrocodone bitratrate after 18 hr, respectively.

Example 9

Varying the Concentrations of a Specific Polyox Grade in the Extended Release Portion of Bilayer Formulations Containing Hydrocodone The data from Examples 7 and 8 indicate that an increase in the amount of POLYOX® in the pharmaceutical composition also retards release of the actives from the pharmaceutical composition. To confirm this observation, bilayer formulations described herein were prepared, each containing a total of 15 mg of hydrocodone bitartrate and a total of 500 mg of acetaminophen. 50% of the acetaminophen was contained in the immediate release portion, and the other 50% was contained in the ER layer. 25% of the hydrocodone bitartrate was contained in the immediate release portion of the formulation, and the other 75% was contained in the ER layer. In a first formulation, POLYOX® 1105 was employed as the extended release component in an amount of 25% by weight of the ER portion. In a second formulation, POLYOX™ 1105 was employed as the extended release component in an amount of 35% by weight of the ER portion. In a third formulation, POLYOX™ 1105 was employed as the extended release component in an amount of 45% by weight of the ER portion.

The cumulative release profiles of acetaminophen and hydrocodone bitartrate from these compositions are shown in FIGS. 19 and 20, respectively. These profiles confirm that as the amount of POLYOX® 1105 used in the pharmaceutical formulations increase, the release rate of the actives generally decreases. For example, the formulations containing 25%, 35%, and 45% POLYOX® 1105 had released about 58%, about 54%, and about 53% acetaminophen after 15 minutes, respectively; about 61%, about 56%, and about 56% acetaminophen after 30 minutes, respectively; about 66%, about 61%, and about 60% acetaminophen after 1 hr, respectively; about 76%, about 70%, and about 68% acetaminophen after 2 hr, respectively; about 90%, about 85%, and about 81% acetaminophen after 4 hr, respectively; about 97%, about 94%, and about 91% acetaminophen after 6 hr, respectively; about 98%, about 97%, and about 96% acetaminophen after 8 hr, respectively; about 97%, about 97%, and about 98% acetaminophen after 12 hr, respectively; and about 97%, about 96%, and about 97% acetaminophen after 18 hr, respectively.

Similar trends were observed for the cumulative release of hydrocodone bitartrate. For example, the formulations containing 25%, 35%, and 45% POLYOX® 1105 had released about 39%, about 34%, and about 33% hydrocodone bitartrate after 15 minutes, respectively; about 47%, about 39%, and about 39% hydrocodone bitartrate after 30 minutes, respectively; about 57%, about 49%, and about 48% hydrocodone bitartrate after 1 hr, respectively; about 72%, about 65%, and about 63% hydrocodone bitartrate after 2 hr, respectively; about 93%, about 88%, and about 84% hydrocodone bitartrate after 4 hr, respectively; about 102%, about 100%, about 97% hydrocodone bitartrate after 6 hr, respectively; about 102%, about 103%, and about 103% hydrocodone bitartrate after 8 hr, respectively; about 102%, about 104%, and about 104% hydrocodone bitartrate after 12 hr, respectively; and about 103%, about 103%, and about 103% hydrocodone bitartrate after 18 hr, respectively.

Example 10

Varying the Concentrations of a Specific Polyox Grade in the Extended Release Portion of Bilayer Formulations Containing Hydrocodone The release rate studies described in Example 9 were repeated, except that the three bilayer formulations were prepared such that they included POLYOX® N-60K instead of 1105.

The cumulative release profiles of acetaminophen and hydrocodone bitartrate from these compositions are shown in FIGS. 21 and 22, respectively. These profiles confirm that as the amount of POLYOX® N-60K used in the pharmaceutical formulations increase, the release rate of the actives generally decreases. For example, the formulations containing 25%, 35%, and 45% POLYOX® N-60K had released about 55%, about 54%, and about 54% acetaminophen after 15 minutes, respectively; about 57%, about 56%, and about 55% acetaminophen after 30 minutes, respectively; about 61%, about 60%, and about 58% acetaminophen after 1 hr, respectively; about 67%, about 65%, and about 64% acetaminophen after 2 hr, respectively; about 76%, about 74%, and about 72% acetaminophen after 4 hr, respectively; about 84%, about 82%, and about 80% acetaminophen after 6 hr, respectively; about 90%, about 88%, and about 86% acetaminophen after 8 hr, respectively; about 97%, about 96%, and about 95% acetaminophen after 12 hr, respectively; and about 97%, about 98%, and about 99% acetaminophen after 18 hr, respectively.

Similar trends were observed for the cumulative release of hydrocodone bitartrate. For example, the formulations containing 25%, 35%, and 45% POLYOX® N-60K had released about 34%, about 32%, and about 31% hydrocodone bitartrate after 15 minutes, respectively; about 41%, about 37%, and about 36% hydrocodone bitartrate after 30 minutes, respectively; about 49%, about 44%, and about 43% hydrocodone bitartrate after 1 hr, respectively; about 60%, about 55%, and about 54% hydrocodone bitartrate after 2 hr, respectively; about 77%, about 72%, and about 71% hydrocodone bitartrate after 4 hr, respectively; about 89%, about 85%, about 84% hydrocodone bitartrate after 6 hr, respectively; about 97%, about 93%, and about 93% hydrocodone bitartrate after 8 hr, respectively; about 104%, about 100%, and about 102% hydrocodone bitartrate after 12 hr, respectively; and about 104%, about 102%, and about 105% hydrocodone bitartrate after 18 hr, respectively.

While the cumulative release profiles of the formulations generally decrease as the amount of the extended release component is increased, this trend is more pronounced for POLYOX® 1105 than for POLYOX® N-60K.

Example 11

In vitro Dissolution of Controlled-Release Bilayer Tablets Containing 15 mg Hydrocodone and 650 mg Acetaminophen Performed at a 150 rpm Paddle Speed Bilayer formulations described herein were prepared, each containing a total of 15 mg of hydrocodone bitartrate and a total of 650 mg of acetaminophen. 50% of the acetaminophen was contained in the immediate release portion, and the other 50% was contained in the ER layer. 25% of the hydrocodone bitartrate was contained in the immediate release portion of the formulation, and the other 75% was contained in the ER layer. POLYOX® N60k was employed as the extended release component in an amount of 45% by weight of the ER portion.

Dissolution profiles for the formulations were determined in a USP Type II apparatus. Six tablets were weighed, placed in a sinker, and dropped into an equilibrated dissolution bath vessel containing 900 mL of (helium sparged) 0.1 N HCl heated to 37° C.±0.5° C. The mixture was stirred at 150±6 rpm, and the temperature was maintained at 37° C.±0.5° C. for 12 hr. The bath vessel was covered with a low evaporation vessel cover. Samples (5 mL) were removed at 0.25 hr, 0.5 hr, 1 hr, 2 hr, 4 hr, 6, hr, 8 hr, 12 hr, and 18 hr. Each sample was filtered through a 0.45 μm filter and analyzed by HPLC using standard procedures.

The cumulative percent release of acetaminophen and hydrocodone bitartrate from each batch are described in Table 22.

TABLE 22

Release rate data of bilayer tablets (15 mg hydrocodone bitartrate; 325 mg acetaminophen) using a 150 rpm dissolution method.

| Time | Hydrocodone Bitartrate | | Acetaminophen | |
|---|---|---|---|---|
| (hr) | Mean (%) | RSD (%) | Mean (%) | RSD (%) |
| 0.25 | 32.6 | 1.5 | 53.4 | 0.9 |
| 0.50 | 37.1 | 2.1 | 55.3 | 1.0 |
| 1 | 44.2 | 2.2 | 58.4 | 0.9 |
| 2 | 55.0 | 1.3 | 63.4 | 1.0 |
| 4 | 71.8 | 0.8 | 72.3 | 1.2 |
| 6 | 83.9 | 1.3 | 79.6 | 1.1 |
| 8 | 92.2 | 0.6 | 85.7 | 1.1 |
| 12 | 99.5 | 0.7 | 93.7 | 1.1 |
| 18 | 101.0 | 0.7 | 97.2 | 1.0 |

All references cited herein are hereby incorporated by reference. The foregoing is offered primarily for purposes of illustration. It will be readily apparent to those skilled in the art that further drugs can be included, and that the shapes, components, additives, proportions, methods of formulation, and other parameters described herein can be modified further or substituted in various ways without departing from the spirit and scope of the invention.

What is claimed is:

1. An extended release pharmaceutical composition, comprising:
    an immediate release portion comprising hydrocodone or a pharmaceutically acceptable salt of hydrocodone, acetaminophen, or a combination thereof; and an extended release portion comprising hydrocodone or a pharmaceutically acceptable salt of hydrocodone, acetaminophen, or a combination thereof;
    wherein the total amount of acetaminophen in the composition is from about 325 mg to about 650 mg and the total amount of hydrocodone or a pharmaceutically acceptable salt thereof in the composition is from about 7.5 mg to about 15 mg;
    wherein when the composition is orally administered to a subject in need thereof the composition delivers the hydrocodone or the pharmaceutically acceptable salt thereof and the acetaminophen to the subject's upper gastrointestinal tract for at least about 4 hours to about 12 hours; and
    wherein there is substantially no effect on $AUC_{0\text{-}inf}$ for hydrocodone and acetaminophen when the pharmaceutical composition is administered in a fed versus fasted state.

2. The extended release pharmaceutical composition of claim 1, wherein the extended release component comprises at least one extended release polymer.

3. The extended release pharmaceutical composition of claim 2, wherein the at least one extended release polymer is a polyethylene oxide.

4. The extended release pharmaceutical composition of claim 3, wherein the polyethylene oxide has a molecular weight from about 500,000 Daltons to about 10,000,000 Daltons.

5. The extended release pharmaceutical composition of claim 1, wherein the total amount of the acetaminophen in the composition is about 325 mg; and the total amount of the hydrocodone or a pharmaceutically acceptable salt thereof in the composition is about 7.5 mg.

6. The extended release pharmaceutical composition of claim 1, wherein the composition is administered to a subject in need thereof at least twice a day.

7. The extended release pharmaceutical composition of claim 1, wherein the composition delivers the hydrocodone or the pharmaceutically acceptable salt thereof and the acetaminophen to the subject's upper gastrointestinal tract for at least about 6 hours.

8. A method of treating pain in a patient in need thereof, comprising administering to the patient the pharmaceutical composition of claim 1.

9. The method of claim 8, wherein the subject in need thereof is suffering from pain or diagnosed with a condition associated with pain, the pain being acute pain or chronic pain.

10. The method of claim 9, wherein the subject in need thereof is suffering from moderate to severe acute pain.

11. An extended release pharmaceutical composition comprising:
    at least one immediate release portion comprising hydrocodone or a pharmaceutically acceptable salt thereof and acetaminophen and at least one extended release portion comprising an extended release component, hydrocodone or a pharmaceutically acceptable salt thereof, and acetaminophen;
    wherein the at least one immediate release portion comprises from about 20% to about 30% (w/w) of the total amount of the hydrocodone or a pharmaceutically acceptable salt thereof, and about 40% to about 60% (w/w) of the total amount of the acetaminophen in the composition;
    wherein the sum of the amounts of the acetaminophen in the immediate release and the extended release portions is about 325 mg;
    wherein the sum of the amounts of the hydrocodone or pharmaceutically acceptable salt thereof in the immediate release and extended release portions is about 7.5 mg; and
    wherein the composition can be administered to a subject in need thereof without regard to food.

12. The extended release composition of claim 11, wherein the AUC of hydrocodone when a subject is in a fasted state is bioequivalent to the AUC of hydrocodone when the subject is in a fed state.

13. The extended release composition of claim 11, wherein the AUC of acetaminophen when a subject is in a fasted state is bioequivalent to the AUC of acetaminophen when the subject is in a fed state.

14. The extended release composition of claim 11, wherein the $C_{max}$ of hydrocodone when a subject is in a fasted state is bioequivalent to the $C_{max}$ of hydrocodone when the subject is in a fed state.

15. The extended release composition of claim 11, wherein there is substantially no effect on $AUC_{0\text{-}inf}$ for hydrocodone and acetaminophen when the composition is administered in a fed versus fasted state.

16. A pharmaceutical composition comprising an immediate release portion and an extended release portion, wherein:
    the immediate release portion comprises acetaminophen and hydrocodone or a pharmaceutically acceptable salt thereof,
    the extended release comprises acetaminophen, hydrocodone or a pharmaceutically acceptable salt thereof, and an extended release component, and the total amount of acetaminophen in the pharmaceutical composition is from about 325 mg to about 650 mg and the total amount of hydrocodone or a pharmaceutically acceptable salt thereof in the pharmaceutical composition is from about 7.5 mg to about 15 mg, wherein the pharmaceutical composition provides an $AUC_{(0-3hr)}$ for hydrocodone after a single dose from about 1.0 ng·hr/mL/mg to about 5.0 ng·hr/mL/mg.

17. The pharmaceutical composition of claim 16, wherein upon oral administration, the pharmaceutical composition provides an $AUC_{(0-3hr)}$ for hydrocodone from about 1.50 ng·hr/mL/mg to about 4.25 ng·hr/mL/mg.

18. The pharmaceutical composition of claim 16, wherein upon oral administration, the pharmaceutical composition provides an $AUC_{(0-3hr)}$ for hydrocodone from about 2.0 ng·hr/mL/mg to about 3.0 ng·hr/mL/mg.

19. The pharmaceutical composition of claim 16, wherein upon oral administration, the pharmaceutical composition provides an $AUC_{0-12hr}$ for hydrocodone from about 5 ng·hr/mL/mg to about 25 ng·hr/mL/mg.

20. The pharmaceutical composition of claim 16, wherein upon oral administration, the pharmaceutical composition provides an $AUC_{0-12hr}$ for hydrocodone from about 7.5 ng·hr/mL/mg to about 15.5 ng·hr/mL/mg.

21. The pharmaceutical composition of claim 16, wherein upon oral administration, the pharmaceutical composition provides an $AUC_{0-12hr}$ for hydrocodone from about 8.5 ng·hr/mL/mg to about 12.5 ng·hr/mL/mg.

22. The pharmaceutical composition of claim 16, wherein upon oral administration, the pharmaceutical composition provides an $AUC_{1-12hr}$ for hydrocodone from about 3 ng·hr/mL/mg to about 20 ng·hr/mL/mg.

23. The pharmaceutical composition of claim 16, wherein upon oral administration, the pharmaceutical composition provides an $AUC_{1-12hr}$ for hydrocodone from about 7.5 ng·hr/mL/mg to about 15.0 ng·hr/mL/mg.

24. The pharmaceutical composition of claim 16, wherein upon oral administration, the pharmaceutical composition provides an $AUC_{1-12hr}$ for hydrocodone from about 8 ng·hr/mL/mg to about 12.5 ng·hr/mL/mg.

25. The pharmaceutical composition of claim 16, wherein upon oral administration, the pharmaceutical composition provides an $AUC_{8-12hr}$ for hydrocodone from about 1 ng·hr/mL/mg to about 6 ng·hr/mL/mg.

26. The pharmaceutical composition of claim 16, wherein upon oral administration, the pharmaceutical composition provides an $AUC_{8-12hr}$ for hydrocodone from about 2 ng·hr/mL/mg to about 5 ng·hr/mL/mg.

27. The pharmaceutical composition of claim 16, wherein upon oral administration, the pharmaceutical composition provides an $AUC_{8-12hr}$ for hydrocodone from about 3 ng·hr/mL/mg to about 4 ng·hr/mL/mg.

* * * * *